US 9,101,653 B2

(12) United States Patent
Kawaoka et al.

(10) Patent No.: US 9,101,653 B2
(45) Date of Patent: Aug. 11, 2015

(54) INFLUENZA VIRUSES WITH MUTANT PB2 GENE SEGMENT AS LIVE ATTENUATED VACCINES

(75) Inventors: Yoshihiro Kawaoka, Middleton, WI (US); Gabriele Neumann, Madison, WI (US); Makoto Ozawa, Kagoshima (JP)

(73) Assignee: Wisconsin Alumni Research Foundation, Madison, WI (US)

( * ) Notice: Subject to any disclaimer, the term of this patent is extended or adjusted under 35 U.S.C. 154(b) by 49 days.

(21) Appl. No.: 13/594,611

(22) Filed: Aug. 24, 2012

(65) Prior Publication Data

US 2013/0230552 A1  Sep. 5, 2013

Related U.S. Application Data

(60) Provisional application No. 61/527,935, filed on Aug. 26, 2011.

(51) Int. Cl.

| | |
|---|---|
| *A61K 39/12* | (2006.01) |
| *A61K 39/145* | (2006.01) |
| *C12N 7/01* | (2006.01) |
| *A61K 35/76* | (2015.01) |
| *C12N 7/00* | (2006.01) |
| *G01N 33/569* | (2006.01) |
| *A61K 39/00* | (2006.01) |

(52) U.S. Cl.
CPC ............... *A61K 35/76* (2013.01); *A61K 39/145* (2013.01); *C12N 7/00* (2013.01); *G01N 33/56983* (2013.01); *A61K 2039/5254* (2013.01); *A61K 2039/5256* (2013.01); *C12N 2760/16121* (2013.01); *C12N 2760/16134* (2013.01); *C12N 2760/16143* (2013.01); *C12N 2760/16171* (2013.01); *G01N 2333/11* (2013.01)

(58) Field of Classification Search
CPC ................... A61K 2039/5254; A61K 39/145; C12N 2760/16121; C12N 2760/16134; C12N 2760/16143; C12N 7/00
See application file for complete search history.

(56) References Cited

U.S. PATENT DOCUMENTS

| | | | |
|---|---|---|---|
| 5,166,057 A | 11/1992 | Palese et al. | |
| 5,786,199 A | 7/1998 | Palese | |
| 5,854,037 A | 12/1998 | Palese et al. | |
| 6,001,634 A | 12/1999 | Palese et al. | |
| 6,271,011 B1 | 8/2001 | Lee et al. | |
| 6,843,996 B1 | 1/2005 | Parkin et al. | |
| 7,176,021 B2 | 2/2007 | Kawaoka | |
| 7,226,774 B2 | 6/2007 | Kawaoka | |
| 7,585,657 B2 | 9/2009 | Kawaoka | |
| 8,298,805 B2 * | 10/2012 | Kawaoka | 435/235.1 |
| 8,597,661 B2 | 12/2013 | Kawaoka et al. | |
| 2004/0002061 A1 | 1/2004 | Kawaoka | |
| 2004/0132164 A1 | 7/2004 | Doyle et al. | |
| 2004/0241139 A1 | 12/2004 | Hobom et al. | |
| 2007/0141699 A1 | 6/2007 | Kawaoka | |
| 2007/0231348 A1 | 10/2007 | Kawaoka et al. | |
| 2008/0009031 A1 | 1/2008 | Kawaoka | |
| 2008/0292658 A1 * | 11/2008 | De Wit et al. | 424/206.1 |
| 2009/0311669 A1 | 12/2009 | Kawaoka | |
| 2009/0324640 A1 | 12/2009 | Kawaoka et al. | |

FOREIGN PATENT DOCUMENTS

| | | |
|---|---|---|
| CA | 2379012 | 1/2001 |
| EP | 1201760 A1 | 5/2002 |
| JP | 07-203958 | 8/1995 |
| WO | WO-00/60050 A2 | 10/2000 |
| WO | WO-0179273 A2 | 10/2001 |
| WO | WO-03/068923 A2 | 8/2003 |
| WO | WO-2006/051069 A2 | 5/2006 |
| WO | WO-2008/147496 A2 | 12/2008 |
| WO | WO-2013/032942 A1 | 3/2013 |
| WO | WO-2013/032942 A9 | 3/2013 |

OTHER PUBLICATIONS

Hwang et al (Journal of Virology 74:4074-4084, 2000).*
Muramoto et al (Journal of Virology 80:2318-2325, 2006).*
Odagiri et al (Journal of Virology 71:2138-2145, 1997).*
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisconsin—Mad, (Feb. 1, 2012), 7.
U.S. Appl. No. 10/081,170, Advisory Action mailed Sep. 27, 2004, 3 pgs.
U.S. Appl. No. 10/081,170, Final Office Action mailed Apr. 12, 2006, 7 pgs.
U.S. Appl. No. 10/081,170, Final Office Action mailed Jul. 13, 2004, 8 pgs.
U.S. Appl. No. 10/081,170, Non Final Office Action mailed Jan. 15, 2004, 9 pgs.
U.S. Appl. No. 10/081,170, Non Final Office Action mailed Feb. 8, 2005, 9 pgs.
U.S. Appl. No. 10/081,170, Non Final Office Action mailed Aug. 24, 2005, 9 pgs.
U.S. Appl. No. 10/081,170, Notice of Allowance mailed Sep. 18, 2006, 8 pgs.
U.S. Appl. No. 10/081,170, Preliminary Amendment filed May 20, 2003, 2 pgs.
U.S. Appl. No. 10/081,170, Preliminary Amendment filed Jun. 6, 2002, 1 pg.
U.S. Appl. No. 10/081,170, Response filed Jan. 24, 2006 to Non Final Office Action mailed Aug. 24, 2005, 11 pgs.

(Continued)

*Primary Examiner* — Mary E Mosher
(74) *Attorney, Agent, or Firm* — Schwegman Lundberg & Woesnner, P.A.

(57) ABSTRACT

The invention provides a recombinant biologically contained influenza virus that is a PB2 knockout virus, e.g., one that is useful to generate a multivalent vaccine, and methods of making and using that virus.

17 Claims, 28 Drawing Sheets
(3 of 28 Drawing Sheet(s) Filed in Color)

(56) References Cited

OTHER PUBLICATIONS

U.S. Appl. No. 10/081,170, Response filed Apr. 12, 2004 to Non Final Office Action mailed Jan. 15, 2004, 12 pgs.
U.S. Appl. No. 10/081,170, Response filed Jun. 8, 2005 to Non Final Office Action mailed Feb. 8, 2005, 11 pgs.
U.S. Appl. No. 10/081,170, Response filed Aug. 17, 2006 to Final Office Action mailed Apr. 12, 2006, 9 pgs.
U.S. Appl. No. 10/081,170, Response filed Sep. 13, 2004 to Final Office Action mailed Jul. 13, 2004, 10 pgs.
U.S. Appl. No. 10/081,170 Response filed Oct. 10, 2003 to Restriction Requirement mailed Sep. 10, 2003, 3 pgs.
U.S. Appl. No. 10/081,170, Restriction Requirement mailed Sep. 10, 2003, 4 pgs.
U.S. Appl. No. 11/509,249, Final Office Action mailed Jun. 12, 2008, 5 pgs.
U.S. Appl. No. 11/509,249, Non Final Office Action with Restriction Requirement mailed Aug. 24, 2007, 8 pgs.
U.S. Appl. No. 11/509,249, Notice of Allowance mailed Apr. 9, 2009, 7 pgs.
U.S. Appl. No. 11/509,249, Notice of Allowance mailed Nov. 17, 2008, 4 pgs.
U.S. Appl. No. 11/509,249, Response filed Feb. 20, 2008 to Non Final Office Action mailed Aug. 24, 2007, 11 pgs.
U.S. Appl. No. 11/509,249, Response filed Oct. 6, 2008 to Office Action mailed Jun. 12, 2008, 11 pgs.
U.S. Appl. No. 11/644,179, Final Office Action mailed May 21, 2013, 11 pgs.
U.S. Appl. No. 11/644,179, Final Office Action mailed Jul. 2, 2010, 8 pgs.
U.S. Appl. No. 11/644,179, Non Final Office Action mailed Nov. 29, 2012, 19 pgs.
U.S. Appl. No. 11/644,179, Non Final Office Action mailed Dec. 8, 2009, 7 pgs.
U.S. Appl. No. 11/644,179, Preliminary Amendment filed Dec. 22, 2006, 5 pgs.
U.S. Appl. No. 11/644,179, Response filed Jan. 30, 2008 to Restriction Requirement mailed Oct. 30, 2007, 5 pgs.
U.S. Appl. No. 11/644,179, Response filed Apr. 8, 2010 to Non Final Office Action mailed Dec. 8, 2009, 8 pgs.
U.S. Appl. No. 11/644,179, Response filed Aug. 17, 2010 to Final Office Action mailed Jul. 2, 2010, 8 pgs.
U.S. Appl. No. 11/644,179, Restriction Requirement mailed Oct. 30, 2007, 7 pgs.
U.S. Appl. No. 11/644,179, Supplemental Preliminary Amendment filed Feb. 6, 2008, 6 pgs.
U.S. Appl. No. 11/644,179. Response filed Feb. 20, 2013 to Non Final Office Action mailed Nov. 29, 2012, 10 pgs.
U.S. Appl. No. 12/113,690, Final Office Action mailed Apr. 15, 2011, 10 pgs.
U.S. Appl. No. 12/113,690, Non-Final Office Action mailed Nov. 10, 2010, 11 pgs.
U.S. Appl. No. 12/113,690, Notice of Allowance mailed Jul. 18, 2013, 14 pgs.
U.S. Appl. No. 12/113,690, Preliminary Amendment filed Jul. 31, 2008, 14 pgs.
U.S. Appl. No. 12/113,690, Response filed Jun. 23, 2011 to Final Office Action mailed Apr. 15, 2011, 17 pgs.
U.S. Appl. No. 12/113,690, Response filed Aug. 5, 2010 to Restriction Requirement mailed Apr. 6, 2010, 14 pgs.
U.S. Appl. No. 12/113,690, Response filed Dec. 22, 2010 to Non Final Office Action mailed Nov. 10, 2010, 19 pgs.
U.S. Appl. No. 12/113,690, Restriction Requirement mailed Apr. 6, 2010, 10 pgs.
U.S. Appl. No. 12/470,287 , Response filed Jan. 23, 2012 to Non Final Office Action mailed Jul. 22, 2011, 13 pgs.
U.S. Appl. No. 12/470,287 , Response filed May 31, 2012 to Final Office Action mailed Apr. 3, 2012, 14 pgs.
U.S. Appl. No. 12/470,287, Corrected Notice of Allowability mailed Sep. 11, 2012, 2 pgs.
U.S. Appl. No. 12/470,287, Final Office Action mailed Apr. 3, 2012, 7 pgs.
U.S. Appl. No. 12/470,287, Non Final Office Action mailed Jul. 22, 2011, 9 pgs.
U.S. Appl. No. 12/470,287, Notice of Allowance mailed Jun. 19, 2012, 5 pgs.
U.S. Appl. No. 12/470,287, Response filed Apr. 28, 2011 to Restriction Requirement mailed Dec. 29, 2010, 8 pgs.
U.S. Appl. No. 12/470,287, Restriction Requirement mailed Dec. 29, 2010, 6 pgs.
Australian Application Serial No. 2003219745, Examiner's First Report mailed Feb. 14, 2007, 2 pgs.
Australian Application Serial No. 2003219745, Response filed Mar. 14, 2008 to Examiner's First Report mailed Feb. 14, 2007, 24 pgs.
Australian Application Serial No. 2008203186, First Examiner Report mailed Jan. 28, 2011, 2 pgs.
Australian Application Serial No. 2008203186, Office Action Received mailed Sep. 16, 2010, 1 page.
Australian Application Serial No. 2008203186, Response filed Mar. 28, 2011 to First Examiner Report mailed Jan. 28, 2011, 51 pgs.
Australian Application Serial No. 2008203186, Response filed Aug. 29, 2011 to Official Action dated Apr. 13, 2011, 20 pgs.
Australian Application Serial No. 2008203186, Subsequent Examiner Report mailed Apr. 13, 2011, 2 pgs.
Brazilian Application Serial No. PI 0307679-2, Office Action published in Patent Gazette No. 1871 of Nov. 14, 2006, 2 pgs.
Brazilian Application Serial No. PI 0307679-2, Petition filed Jan. 10, 2007 in response to publication dated Nov. 14, 2006, 6 pgs.
Canadian Application Serial No. 11/509,249, Response filed May 16, 2011 to Office Action mailed Nov. 18, 2010, 15 pgs.
Canadian Application Serial No. 2,492,097, Office Action mailed Jan. 10, 2012, 4 pgs.
Canadian Application Serial No. 2,492,097, Office Action mailed Apr. 24, 2008, 3 pgs.
Canadian Application Serial No. 2,492,097, Office Action mailed Jul. 31, 2009, 3 pgs.
Canadian Application Serial No. 2,492,097, Response filed Jan. 29, 2010 to Office Action mailed Jul. 31, 2009, 13 pgs.
Canadian Application Serial No. 2,492,097, Response filed May 2, 2012 to Office Action mailed Jan. 10, 2012, 12 pgs.
Canadian Application Serial No. 2,492,097, Response filed Oct. 23, 2008 to Office Action mailed Apr. 24, 2008, 14 pgs.
Canadian Application Serial No. 2492097, Office Action mailed Nov. 18, 2010, 4 pgs.
Chinese Application Serial No. 03808356.6, Office Action mailed Sep. 5, 2008, (English Translation), 6 pgs.
Chinese Application Serial No. 03808356.6, Office Action received Jul. 1, 2011, (w/ English Translation of Office Action), 8 pgs.
Chinese Application Serial No. 03808356.6, Reexamination Notice mailed Nov. 26, 2012, (w/ English Translation), 9 pgs.
Chinese Application Serial No. 03808356.6, Response filed Mar. 11, 2013 to Office Action mailed Nov. 26, 2012, (w/ English Translation of Amended Claims), 9 pgs.
Chinese Application Serial No. 03808356,6, Response filed Mar. 16, 2009 to Office Action mailed Sep. 5, 2008, (w/ English Translation of Claims), 8 pgs.
Chinese Application U.S. Appl. No. 03808356.6, Response filed Oct. 14, 2011 to Office Action mailed Jul. 1, 2011, (w/ English Translation of Amended Claims), 25 pgs.
European Application Serial No. 03716017.3, Office Action mailed Aug. 23, 2012, 4 pgs.
European Application Serial No. 02724994.5, Office Action mailed Mar. 27, 2009, 2 pgs.
European Application Serial No. 03716017.3, Communication and Supplementary European Search Report mailed Jan. 2, 2008, 8 pgs.
European Application Serial No. 03716017.3, Communication mailed May 23, 2006, 3 pgs.
European Application Serial No. 03716017.3, Communication mailed Jul. 26, 2006, 2 pgs.
European Application Serial No. 03716017.3, Communication mailed Oct. 20, 2008, 7 pgs.
European Application Serial No. 03716017.3, Office Action mailed Jul. 27, 2010, 4 pgs.

(56) References Cited

OTHER PUBLICATIONS

European Application Serial No. 03716017.3, Response filed Feb. 4, 2011 to Office Action mailed Jul. 27, 2010, 12 pgs.
European Application Serial No. 03716017.3, Response filed Mar. 4, 2013 to Examination Notification Art. 94(3) mailed Aug. 23, 2012, 19 pgs.
European Application Serial No. 03716017.3, Response filed Jul. 28, 2006 to Communication mailed May 23, 2006, 5 pgs.
European Application Serial No. 03716017.3, Response filed Aug. 19, 2009 to Communication mailed Oct. 20, 2008, 17 pgs.
International Application Serial No. PCT/US2003/004233, International Search Report mailed Dec. 16, 2005, 5 pgs.
International Application Serial No. PCT/US2008/005641, International Search Report mailed Feb. 4, 2009, 6 pgs.
International Application Serial No. PCT/US2008/005641, Written Opinion mailed Feb. 4, 2009, 8 pgs.
International Application Serial No. PCT/US2012/052368, International Search Report mailed Dec. 3, 2012, 4 pgs.
International Application Serial No. PCT/US2012/052368, Written Opinion mailed Dec. 3, 2012, 6 pgs.
Israel Application Serial No. 163,546, First Examination Report mailed Jul. 28, 2008, (English Translation), 2 pgs.
Israel Application Serial No. 163,546, Office Action mailed Nov. 12, 2009, (English Translation), 1 pg.
Israel Application Serial No. 163,546, Office Action mailed Dec. 12, 2007, (English Translation), 1 pg.
Israel Application Serial No. 163,546, Response filed May 9, 2008 to Office Action mailed Dec. 26, 2007, 2 pgs.
Israel Application Serial No. 163,546, Response filed Jun. 8, 2010 to Office Action mailed Nov. 12, 2009, 3 pgs.
Israeli Application Serial No. 163,546, Response filed Aug. 16, 2009 to Substantive Examination Report mailed Feb. 23, 2009, 4 pgs.
Israeli Application Serial No. 163,546, Response filed Oct. 20, 2010 to Office Action dated Jun. 8, 2010, 8 pgs.
Israeli Application Serial No. 163,546, Response filed Nov. 27, 2008 to First Examination Report mailed Jul. 28, 2008, 13 pgs.
Israeli Application Serial No. 163,546, Substantive Examination Report mailed Feb. 23, 2009, (English Translation), 3 pgs.
Israeli Application Serial No. 163546, Office Action mailed Jun. 8, 2010, 1 pg.
Japanese Application Serial No. 2003-315106, Amended Claims filed Oct. 15, 2009 in Response to Office Action mailed Jun. 24, 2009, (English Translation), 6 pgs.
Japanese Application Serial No. 2003-315106, Notice of Allowance mailed Jan. 5, 2010, 3 pgs.
Japanese Application Serial No. 2003-315106, Office Action mailed Jun. 24, 2009, (w/ English Translation), 10 pgs.
Japanese Application Serial No. 2003-568038, Amendment filed Aug. 19, 2005, (English Translation), 9 pgs.
Japanese Application Serial No. 2003-568038, Office Action mailed May 15, 2009, (w/ English Translation), 7 pgs.
Japanese Application Serial No. 2003-568038, Office Action mailed Jul. 10, 2008, (w/ English Translation), 11 pgs.
Japanese Application Serial No. 2003-568038, Request for Examination filed Aug. 19, 2005 (w/ English Translation), 8 pgs.
Japanese Application Serial No. 2003-568038, Response filed Sep. 14, 2009 to Office Action mailed May 15, 2009, (w/ English Translation of Amended Claims), 10 pgs.
Japanese Application Serial No. 2003-568038, Response filed Dec. 10, 2008 to Office Action mailed Jul. 10, 2008, (w/ English Translation of Amended Claims), 15 pgs.
Japanese Application Serial No. 2008-315106, Office Action mailed Jul. 13, 2009, (w/ English Translation), 10 pgs.
Japanese Application Serial No. 2008-315106, Response filed Oct. 15, 2009 to Office Action mailed Jun. 24, 2009, (w/ English Translation of Amended Claims), 103 pgs.
Japanese Application Serial No. 2008-315106, Response filed Dec. 3, 2009 to Office Action mailed Jun. 24, 2009, (w/ English Translation of Amended Claims), 9 pgs.
Japanese Application Serial No. 2009-238781, Office Action mailed Oct. 11, 2011, (w/ English Translation), 3 pgs.
Korean Application Serial No. 10-2004-7012647, Office Action mailed Feb. 26, 2010, (w/ English Translation), 7 pgs.
Korean Application Serial No. 10-2004-7012647, Response filed Jun. 10, 2010 to Office Action mailed Feb. 26, 2010, (w/ English Translation of Claims), 17 pgs.
Korean Application Serial No. 10-2010-7011520, Office Action mailed Jul. 20, 2010, (w/ English Translation), 6 pgs.
Korean Application Serial No. 10-2010-7011520, Response filed Oct. 20, 2010 to Office Action mailed Jul. 20, 2010, (w/ English Translation of Amended Claims), 30 pgs.
Korean Application Serial No. 10-2010-7011520, Amended Claims filed May 24, 2011 in Response to Office Action mailed Feb. 24, 2011, (English Translation of Amended Claims), 22 pgs.
Korean Application Serial No. 10-2010-7011520, Office Action mailed Feb. 24, 2011, (w/ English Translation), 5 pgs.
Mexican Application Serial No. PA/a/2004/007914, Office Action mailed Feb. 14, 2008, 3 pgs.
Mexican Application Serial No. PA/a/2004/007914, Office Action mailed Feb. 22, 2008, (English Translation), 3 pgs.
Mexican Application Serial No. PA/a/2004/007914, Response filed Jun. 11, 2008 to Office Action mailed Feb. 22, 2008, (w/ English Translation of Claims), 68 pgs.
"Nucleotide sequences of influenza virus segments 1 and 3 reveal mosaic structure of a small viral RNA segment", Database Uniprot, (Nov. 14, 2001), 2 pgs.
Bilsel, P., et al., "Mutations in the Cytoplasmic Tail of Influenza A Virus Neuraminidase Affect Incorporation into Virions", *Journal of Virology*, 67(11), (Nov. 1993), 6762-6767.
Brandli, A. W. et al., "A Polarized Epithelial Cell Mutant Deficient in Translocation of UDP-galactose into the Golgi Complex", *Journal of Biological Chemistry*, 263(31), (1988), 16283-16290.
Castrucci, M. R, et al., "Attenuation of Influenza A Virus by Insertion of a Foreign Epitope into the Neuraminidase", *Journal of Virology*, 66(8), (1992), 4647-4653.
Castrucci, M. R., et al., "Biologic Importance of Neuraminidase Stalk Length in Influenza A Virus", *Journal of Virology*, 67(2), (1993), 759-764.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", *Journal of Virology*, 68(6), (1994), 3486-3490.
Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", *Virology*, 265(2), (1999), 342-353.
Desselberger, Ulrich, et al., "The 3' and 5'-terminal sequences of influenza A, B and C virus RNA segments are highly conserved and show partial inverted complementarity", *Gene*, 8(3), (1980), 315-328.
Dollenmaier, G., et al., "Membrane-Associated Respiratory Syncytial Virus F Protein Expressed From a Human Rhinovirus Type 14 Vector Is Immunogenic", *Virology*, 281(2), (2001), 216-230.
Duhaut, S., et al., "Approximately 150 Nucleotides from the 5' End of an Influenza a Segment 1 Defective Virion RNA are needed for Genome Stability During Passage of Defective Virus in Infected Cells", *Virology*, 275(2), (2000), 278-285.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", *Virology*, 248(2), (1998), 241-253.
Durbin, A. P, et al., "Human Parainfluenza Virus Type 3 (PIV3) Expressing the Hemagglutinin Protein of Measles Virus Provides a Potential Method for Immunization Against Measles Virus and PIV3 in Early Infancy", *Journal of Virology*, 74(51), (Aug. 2000), 6821-6831.
Flandorfer, A., et al., "Chimeric Influenza A Viruses with a Functional Influenza B Virus Neuraminidase or Hemagglutinin", *Journal of Virology*, 77(17), (2003), 9116-9123.

(56) References Cited

OTHER PUBLICATIONS

Fuji, Y., et al., "Selective incorporation of influenza virus RNA segments into virions", *Proc. Natl. Acad. Sci. USA*, 100(4), (2003), 2002-2007.

Fujii, Y. et al., "The packaging of influenza viral genome", *Virus*, 52(1), Ulrusu (Japanese Journal Name), (Jun. 2002), 203-206.

Garcia-Sastre, A., et al., "Introduction of Foreign Sequences into the Genome of Influenza A Virus.", In: *Recombinant Vectors in Vaccine Development. Dev. Biol. Stand.*, 82, Fred Brown, Editor, (1994), 237-246.

Garcia-Sastre, A., et al., "Use of a mammalian internal ribosomal entry site element for expression of a foreign protein by a transfectant influenza virus.", *Journal of Virology*, 68(10), (1994), 6254-6261.

Ghate, A. A., et al., "Influenza Type B Neuraminidase Can Replace the Function of Type A Neuraminidase", *Virology*, 264 (2), (1999), 265-277.

Gilleland, H. E, et al., "Chimeric Influenza Virus Incorporating Epitopes of Outer Membrane Protein F as a Vaccine Against Pulmonary Infection with *Pseudomonas aeruginosa", Behring Inst. Mitt. 98*, (1997), 291-301.
Green, R. F., et al., "Glycosylation Does Not Determine Segregation of Viral Envelope Proteins in the Plasma Membrane of Epithelial Cells", *J. Cell Biol.*, 89(2), (1981), 230-239.
Hiti, A. L., et al., "P03470—Neuraminidase", Entrez Protein Database, [online]. [retrieved on Aug. 30, 2006], Retrieved from the Internet: <URL: http://www.ncbi.nlm.nih.gov/entrez/viewer.fcgi?db=protein&val=84028231>, (1982), 730-734 (8 pgs.).
Hughes, M. T., et al., "Adaptation of Influenza A Viruses to Cells Expressing Low Levels of Sialic Acid Leads to Loss of Neuraminidase Activity", *Journal of Virology*, 75(8), (2001), 3766-3770.
Hughes, M. T., et al., "Influenza A Viruses Lacking Sialidase Activity Can Undergo Multiple Cycles of Replication in Cell Culture, Eggs, or Mice", *Journal of Virology*, 74(11), (2000), 5206-5212.
Ito, T, et al., "Differences in Sialic Acid-Galactose Linkages in the Chicken Egg Amnion and Allantois Influence Human Influenza Virus Receptor Specificity and Variant Selection", *Journal of Virology*, 71(4), (Apr. 1997), 3357-3362.
Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", *Journal of Virology*, 78(2), (2004), 995-998.
Latham, T, et al., "Formation of Wild-Type and Chimeric Influenza Virus-Like Particles following Simultaneous Expression of Only Four Structural Proteins", *Journal of Virology 75* (13), (2001), 6154-6165.
Li, S., et al., "Influenza A Virus Transfectants with Chimeric Hemagglutinins Containing Epitopes from Different Subtypes", *Journal of Virology*, 66(1), (1992), 399-404.
Li, S., et al, "Recombinant Influenza A Virus Vaccines for the Pathogenic Human A/Hong Kong/97 (H5N1) Viruses", *J. Infect. Dis.*, 179(5), (1999), 1132-1138.
Liu, C., et al., "Influenza type A virus neuraminidase does not play a role in viral entry, replication, assembly, or budding.", *Journal of Virology*, 69(2), (1995), 1099-1106.
Liu, C., et al., "Selection and Characterization of a Neuraminidase-Minus Mutant of Influenza Virus and its Rescue by Cloned Neuraminidase Genes", *Virology*, 194(1), (1993), 403-407.
Luytjes, W., "Amplification, Expression, and Packaging of a Foreign Gene by Influenza Virus", *Cell*, 59(6), (1989), 1107-1113.
Martin, J., et al., "Studies of the Binding Properties of Influenza Hemagglutinin Receptor-Site Mutants", *Virology*, 241(1), (1998), 101-111.
Masuda, H., et al., "Substitution of Amino Acid Residue in Influenza A Virus Hemagglutinin Affects Recognition of Sialyl-Oligosaccharides Containing N-Glycolylneuraminic Acid", *FEBS Letters*, 464, (1999), 71-74.
Matta, M, et al., "Cell-surface sialoglycoconjugate structures in wild-type and mutant *Crithidia fasciculata", Parasitol. Res.*, 85(4), (1999), 293-299.
Mishin, V. P, et al., "Protection afforded by intranasal immunization with the neuraminidase-lacking mutant of influenza A virus in a ferret model", *Vaccine*, 23(22), (2005), 2922-2927.
Mitnaul, L. J., et al., "Balanced Hemagglutinin and Neuraminidase Activities are Critical for Efficient Replication of Influenza A Virus", *Journal of Virology*, 74 (13), (2000), 6015-6020.
Murphy, B, R. et al., "An influenza A live attenuated reassortant virus possessing three temperature-sensitive mutations in the PB2 polymerase gene rapidly loses temperature sensitivity following replication in hamsters", *Vaccine*, 15(12-13), (Aug.-Sep. 1997), 1372-1378.
Muster, T., et al., "An Influenza A Virus Containing Influenza B Virus 5' and 3' Noncoding Regions on the Neuraminidase Gene is Attenuated in Mice", *Proc. Natl. Acad. Sci. USA*, 88, (1991), 5177-5181.
Neumann, G., et al., "Generation of influenza A viruses entirely from cloned cDNAs", *Proc., Natl. Acad. Sci. USA.*, 96(16), (1999), 9345-9350.
Neumann, G., et al., "Influenza A virus NS2 protein mediates vRNP nuclear export through NES-independent interaction with hCRM1", *The EMBO Journal*, 19(24), (2000), 6751-6758.
Neumann, G., et al., "Mutational Analysis of Influenza Virus Promoter Elements In Vivo", *Journal of General Virology*, 76, (1995), 1709-1717.
Ozawa, M., et al., "Replication-incompetent influenza A viruses that stably express a foreign gene", *Journal of General Virology*, 92(Part 12), (2011), 2879-2888.
Pattnaik, A. K., et al., "The Termini of VSV DI Particle RNAs are Sufficient to Signal RNA Encapsidation, Replication, and Budding to Generate Infectious Particles", *Virology*, 206, (1995), 760-764.
Percy, N., et al., "Expression of a Foreign Protein by Influenza A Virus", *Journal of Virology*, 68(7), (1994), 4486-4492.
Piatti, G., "Identification of immunodominant epitopes in the filamentous Hemagglutinin of *Bordetella pertusis", FEMS Immunology and Medical Microbiology*, 23(3), (1999), 235-241.
Portela, A., et al., "Replication of orthomyxoviruses", *Advances in Virus Research*, 54, (1999), 319-348.
Ray, M. K., et al., "A Novel Glycosylation Phenotype Expressed by Lec23, a Chinese Hamster Ovary Mutant Deficient in α-Glucosidase I", *Journal of Biological Chemistry*, 266(34), (1991), 22818-22825.
Rayner, J., et al., "Alphavirus vectors and vaccination", *Reviews in Medical Virology*, 12, (2002), 279-296.
Restifo, N. P., et al., "Transfectant Influenza A Viruses are Effective Recombinant Immunogens in the Treatment of Experimental Cancer", *Virology*, 249(1), (1998), 89-97.
Rodrigues, M. et al., "Influenza and Vaccinia Viruses Expressing Malaria $CD8^+$ T and B Cell Epitopes. Comparison of Their Immunogenicity and Capacity to Induce Protective Immunity", *J. Immunol.*, 153(10), (1994), 4636-4648.
Schultz-Cherry, S., et al., "Influenza Virus NS1 Protein Induces Apoptosis in Cultured Cells", *Journal of Virology*, 75(17), (2001), 7875-7881.
Shinya, K., et al., "Characterization of a Neuraminidase-Deficient Influenza A Virus as a Potential Gene Delivery Vector and a Live Vaccine", *Journal of Virology*, 78(6), (2004), 3083-3088.
Stray, S. J., et al., "Influenza virus infection of desialylated cells", *Glycobiology*, 10(7), (2000), 649-658.
Strobel, I., et al., "Efficient Expression of the Tumor-Associated Antigen MAGE-3 in Human Dendritic Cells, Using an Avian Influenza Virus Vector", *Human Gene Therapy*, 11(16), (2000), 2207-2218.
Takeda, T., et al., "Expression of Podocalyxin Inhibits Cell-Cell Adhesion and Modifies Junctional Properties in Madin-Darby Canine Kidney Cells", *Molecular Biology of the Cell*, 11, (2000), 3219-3232.
Terry, G., et al., "The Contruction of Defective Interfering Rubella Virus Particles", *Archives of Virology*, 145(3), (2000), 625-633.
Walker, W. S, et al., "HEL-Flu: an influenza virus containing the hen egg lysozyme epitope recognized by $CD4^+$ T cells fom mice transgenic for an αβ TCR", *J. Immunol.*, 159(6), (Sep. 1997), 2563-2566.
Watanabe, S., et al., "Influenza A Virus Lacking M2 Protein as a Live Attenuated Vaccine", *Journal of Virology*, 83(11), (2009), 5947-5950.

(56) References Cited

OTHER PUBLICATIONS

Yang, P., et al., "Hemagglutinin Specificity and Neuraminidase Coding Capacity of Meuraminidase-Deficient Influenza Viruses", *Virology*, 229(1), (1997), 155-165.

Zhang, Xuming, et al., "Expression of Interferon-γ by a Coronavirus Defective-Interfering RNA Vector and its Effect on Viral Replication, Spread, and Pathogenicity", Medical Institute, University of Southern California School of Medicine, (May 1997), 327-338.

U.S. Appl. No. 12/113,690, Notice of Allowability mailed Aug. 19, 2013, 9 pgs.

Canadian Application Serial No. 2,816,242, Office Action mailed Jun. 16, 2014, 3 pgs.

International Application Serial No. PCT/US03/04233, International Search Report mailed Dec. 16, 2005, 7 pgs.

International Application Serial No. PCT/US2008/005641, International Preliminary Report on Patentability dated Nov. 10, 2009, 9 pgs.

International Application Serial No. PCT/US2012/052368, International Preliminary Report on Patentability mailed Mar. 13, 2014, 8 pgs.

Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.

Hossain, M. J., et al., "Establishment and Characterization of a Madin-Darby Canine Kidney Reporter Cell Line for Influenza A Virus Assays", J Clin Microbiol, 48(7), (2010), 2515-2523.

Li, F., et al., "Generation of Replication-Competent Recombinant Influenza A Viruses Carrying a Reporter Gene Harbored in the Neuraminidase Segment", J. Virol., 84(22), (2010), 12075-12081.

Manicassamy, B., et al., "Analysis of in vivo dynamics of influenza virus infection in mice using a GFP reporter virus", Proc Natl Acad Sci. USA, 107(25), (2010), 11531-11536.

Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.

Muramoto, Y., et al., "Hierarchy among Viral RNA (vRNA) Segments in Their Role in vRNA Incorporation into Influenza A Virions", J. Virol., 80(5), (2006), 2318-2325.

Rimmelzwaan, G. F., et al., "Use of GFP-expressing influenza viruses for the detection of influenza virus A/H5N1 neutralizing antibodies", Vaccine, 29(18), (2011), 3424-3430.

Chinese Application Serial No. 201310400039.8, Office Action mailed Aug. 21, 2014, (w/ English Translation), 13 pgs.

Israeli Application Serial No. 211324, Office Action mailed Sep. 18, 2014, (English Translation), 5 pgs.

"Nucleotides Sequences of Influenza Virus Segments 1 and 3 Reveal Mosaic Structrure of Small Viral RNA Segment", Database UniProt EBI / Accession No. NC 002023, (Jul. 10, 2008), 15 pgs.

Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", *J. Virol.*, 68(6), (Jun. 1994), 3486-3490.

Fields, S., et al., "Nucleotides Sequences of Influenza Virus Segments 1 and 3 Reveal Mosaic Structrure of Small Viral RNA Segment", *Cell*, 28, (1982), 303-313.

Garcia-Sastre, A., et al., "Introduction of Foreign Sequences into the Genome of Influenza A Virus", *Dev. Biol. Stand.* vol. 82, (1994), 237-246.

\* cited by examiner

| PB2 MUTANT vRNAs | | NUMBER OF VLPs (/ml) | NUMBER OF VLPs POSSESSING GFP vRNA (/ml) | EFFICIENCY OF VIRION INCORPORATION |
|---|---|---|---|---|
| PB2(300)GFP(300) | 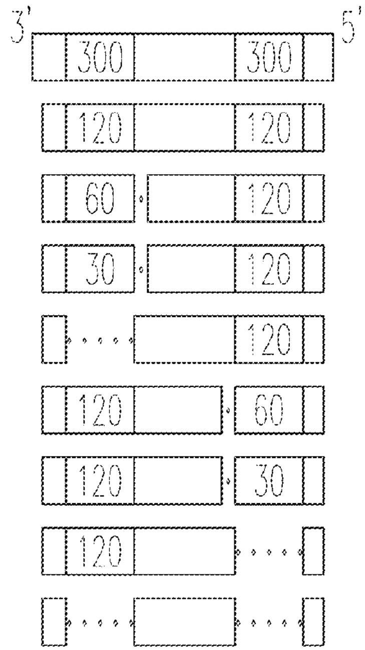  | 2,799,200 | 1,532,400 | 54.7% |
| PB2(120)GFP(120) | | 1,080,800 | 753,600 | 69.7% |
| PB2(60)GFP(120) | | 1,676,800 | 960,000 | 57.3% |
| PB2(30)GFP(120) | | 1,807,200 | 839,200 | 46.4% |
| PB2(0)GFP(120) | | 1,093,600 | 322,400 | 29.5% |
| PB2(120)GFP(60) | | 1,756,800 | 1,132,800 | 64.5% |
| PB2(120)GFP(30) | | 1,068,000 | 549,600 | 51.5% |
| PB2(120)GFP(0) | | 56,000 | 42,400 | 75.7% |
| PB2(0)GFP(0) | | 28,000 | 0 | 0.0% |
| PB2(−) | NONE | 19,600 | – | – |

FIGURE 1

SEQ ID NO: 1
agcgaaagca  ggtactgatc  caaaatggaa  gattttgtgc  gacaatgctt  caatccgatg    60
attgtcgagc  ttgggaaaa   aacaatgaaa  gagtatgggg  aggacctgaa  aatcgaaaca   120
aacaaatttg  cagcaatatg  cactcacttg  gaagtatgct  tcatgtattc  agattttcac   180
ttcatcaatg  agcaaggcga  gtcaataatc  gtagaacttg  gtgatccaaa  tgcactttg    240
aagcacagat  ttgaaataat  cgagggaaga  gatcgcacaa  tggcctggac  agtagtaaac   300
agtatttgca  acactacagg  ggctgagaaa  ccaaagtttc  taccagattt  gtatgattac   360
aaggagaata  gattcatcga  aattggagta  acaggagag   aagttcacat  atactatctg   420
gaaaaggcca  ataaaattaa  atctgagaaa  acacacatcc  acattttctc  gttcactggg   480
gaagaaatgg  ccacaaaggc  agactacact  ctcgatgaag  aaagcagggc  taggatcaaa   540
accagactat  tcaccataag  acaagaaatg  gccagcagag  cctctggaa   tccttttcgt   600
cagtccgaga  gaggagaaga  gacaattgaa  gaaaggtttg  aaatcacagg  aacaatgcgc   660
aagcttgccg  accaaagtct  ccgcgcgaac  ttctccagcc  ttgaaaattt  tagagcctat   720
gtggatggat  tcgaaccgaa  cggctacatt  gagggcaagc  tgtctcaaat  gtccaaagaa   780
gtaaatgcta  gaattgaacc  ttttttgaaa  acaaccaacc  gaccacttag  acttccgaat   840
gggcctcctg  gttctcagcg  gtccaaattc  ctgctgatgg  atgccttaaa  attaagcatt   900
gaggacccaa  gtcatgaagg  agagggaata  ccgctatatg  atgcaatcaa  atgcatgaga   960
acatttcttg  gatggaagga  accaatgtt   gttaaacac   acgaaaaggg  aataaatcca  1020
aactatctc   tgtcatggaa  gcaagtactg  gcagaactgc  aggacattga  gaatgaggag  1080
aaaattccaa  agactaaaaa  tatgaagaaa  acaagtcagc  taaagtgggc  acttggtgag  1140
aacatggcac  cagaaaaggt  agactttgac  gactgtaaag  atgtaggtga  tttgaagcaa  1200
tatgatagtg  atgaaccaga  attgaggtcg  cttgcaagct  ggattcagaa  tgagtttaac  1260
aaggcatgcg  aactgacaga  ttcaagctgg  atagagctcg  atgagattgg  agaagatgtg  1320
gctccaattg  aacacattgc  aagcatgaga  aggaattatt  tcacatcaga  ggtgtctcac  1380
tgcagagcca  cagaatacat  aatgaaggga  gtgtacatca  atactgcctt  gcttaatgca  1440
tcttgtgcag  caatggatga  tttccaatta  attccaatga  taagcaagtg  tagaactaag  1500
gagggaaggc  gaaagaccaa  cttgtatggt  tcatcataa   aaggaagatc  ccacttaagg  1560
aatgacaccg  acgtggtaaa  cttgtgagc   atggagtttt  ctctcactga  cccaagactt  1620
gaaccacata  aatgggagaa  gtactgtgtt  cttgagatag  gagatatgct  tataagaagt  1680
gccataggcc  aggtttcaag  gcccatgttc  ttgtatgtga  aacaaatgg   aacctcaaaa  1740
attaaaatga  aatgggaat   ggagatgagc  gttgcctcc   tccagtcact  tcaacaaatt  1800
gagagtatga  ttgaagctga  gtccctgtc   aaagagaaag  acatgaccaa  agagttcttt  1860
gagaacaaat  cagaaacatg  gcccattgga  gagtccccca  aaggagtgga  ggaaagttcc  1920
attgggaagg  tctgcaggac  tttattagca  agtcggtat   tcaacagctt  gtatgcatct  1980
ccacaactag  aaggatttc   agctgaatca  agaaaactgc  ttcttatcgt  tcaggctctt  2040
agggacaacc  tggaacctgg  gacctttgat  cttggggggc  tatataagc   aattgaggag  2100
tgcctgatta  atgatccctg  ggttttgctt  aatgcttctt  ggttcaactc  cttccttaca  2160
catgcattga  gttagttgtg  gcagtgctac  tatttgctat  ccatactgtc  caaaaagta   2220
ccttgttct   act                                                         2233

SEQ ID NO: 2
agcgaaagca  ggcaaaccat  ttgaatggat  gtcaatccga  ccttactttt  cttaaaagtg    60
ccagcacaaa  atgctataag  cacaactttc  cttatactg   gagaccctcc  ttacagccat    120
gggacaggaa  caggatacac  catggatact  gtcaacagga  cacatcagta  ctcagaaaag   180
ggaagatgga  caacaaacac  cgaaactgga  gcaccgcaac  tcaacccgat  tgatgggcca   240
ctgccagaag  acaatgaacc  aagtggttat  gccaaacag   attgtgtatt  ggaggcgatg   300
gctttcctg   aggaatcca   tcctggtatt  ttgaaaact   cgtgtattga  acgatggag    360
gttgttcagc  aaaacgagt   agacaagctg  acaaaggcc   gacagaccta  tgactggact   420
ctaaatagaa  accaacctgc  tgcaacagca  ttggccaaca  caatagaagt  ttcagatca   480
aatggcctca  cggccaatga  gtggaagg   ctcatagatt  tccttaagga  tgtaatggag   540
tcaatgaaca  aagaagaaat  gggatcaca   actcattc   agagaaagag  acgggtgaga   600
gacaatatga  ctaagaaaat  gataacacag  agaacaatgg  taaaaatgg   gcagagattg   660
aacaaaagga  gttatctaat  tagagcattg  accctgaaca  caatgaccaa  agatgctgtg   720
agagggaagc  taaacgagg   agcaatgca   acccaggga  tgcaaataag  ggggtttgta   780

```
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaacttc  tttcaccatc actggagata acaccaaatg gaacgaaaat    960
cagaatcctc ggatgttttt ggccatgatc acatatatga ccagaaatca gccgaatgg   1020
ttcagaaatg ttctaagtat tgctccaata atgttctcaa acaaaatggc gagactggga   1080
aaaggtata  tgtttgagag caagagtatg aaacttagaa ctcaaatacc tgcagaaatg   1140
ctagcaagca tcgatttgaa atatttcaat gattcaacaa gaaagaagat tgaaaaaatc   1200
cgaccgctct taatagaggg gactgcatca ttgagccctg aatgatgat  gggcatgttc   1260
aatatgttaa gcactgtatt aggctgtctcc atctgaatc ttggacaaaa gagatacacc   1320
aagactactt actggtggga tggtcttcaa tcctctgacg attttgctct gattgtgaat   1380
gcacccaatc atgaagggat tcaagccgga gtcgacaggt ttattgaac  ctgaagcta   1440
cttggaatca atatgagcaa gaaaaagtct tacataaaca gaacaggtac atttgaattc   1500
acaagttttt tctatcgtta tggttttgtt gccaattca  gcatggagct tccagtttt   1560
gtggtgtctg ggatcaacga gtcagcggac atgagtatty gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aaccgaaga    1740
tcatttgaaa taaagaaact gtgggagcaa accgttcca  aagctggact gctggtctcc   1800
gacggaggcc caaatttata caacattaga aatctccaca ttcctgaagt ctgcctaaaa   1860
tgggaattga tggatgaaga ttaacaggg  cgtttatgca accactgaa  cccattgtc    1920
agccataaag aaattgaatc aatgaacaat gcagtgatga tgcacagca  tggtccagcc   1980
aaaaacatgg agtatgatgc tgttgcaaca acactcct  cgatcccaa  aagaaatcga   2040
tccatcttga atacaagtca aagaggagta cttgaggatg aacaatgta  ccaaaggtgc   2100
tgcaatttat ttgaaaaatt cttccccagc agttcataca gaagaccagt cggatatcc    2160
agtatggtgg aggctatggt tccagagcc  cgaattgatg cacggattga tttcgaatct   2220
ggaaggataa agaaagaaga gttcactgag atcatgaaga tctgttccac cattgaagag   2280
ctcagacggg aaaaatagtg aatttagctt gtccttcatg aaaaaatgcc ttgtttctac   2340
t                                                                   2341

SEQ ID NO: 3
agcgaaagca gtcaattat  attcaatatg gaagaataa  aagaactacg aaatctaatg     60
tgcagtctc  gcaccgcga  gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gaycaaggac aaactttatg gagtaaaatg aatgatgccg gatcagaccg agtgatggta    300
tcacctctg  ctgtgacatg tggaatagg  aatggaccaa taacaaatac agttcattat    360
ccaaaaatct acaaaactta tttgaaaga  gtcgaaagca taaagcatgg aaccttggcc    420
ctgtccatt  ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcgaatcg  caactaacga taaccaaaga gaagaaagaa    600
gaactccagg attgcaaaat ttctcctttg atggttcat  acatgttgga gagaactg     660
gtccgcaaaa cgagattcct cccagtggct ggtggaacaa gcagtgtgta cattgaagtg    720
ttgcatttga ctcaaggaac atgctggaa  cagatgtata tcccaggagg gaagtgagg    780
aatgatgaty ttgatcaaag cttgattatt gctgctagga acatagtgag aagagctgca    840
gtatccgcag atccactagc atctttattg gagatgtgcc acagcacaca gattggtgga    900
attaggatgg tagacatcct taggcagaac ccaacagaag aagcagccgt ggatatatgc    960
aaggctgcaa tgggactgag aattagctca tccttcagtt ttggtggatt cacatttaag    1020
agaacaagcg gatcatcagt caagagagag gaagaggtgc ttacggcaa  tcttcaaaca    1080
ttgaagataa gagtgcatga gggatatgaa gagttcacaa tggttgggag aagagcaaca    1140
gccatactca gaaaagcaac caggagattg attcagctga tagtgagtgg agagacgaa    1200
cagtcgattg ccgaagcaat aattgtggcc atggtatttt cacaagagga ttgtatgata    1260
aagcagtca  gaggtgatct gaatttcgtc aatagggcga atcaacgat  gaatcctatg    1320
catcaaactt taagcatt  tcagaaggat gcaaagtgc  ttttcaaaa  ttggggagct    1380
gaacctatcg acaatgtgat gggaatgatt gggatattgc cgacatgac  tcaagcaatc    1440
```

FIGURE 2B

```
gagatgtcaa tgagaggagt gagaatcagc aaaatgggtg tagatgagta ctccagcacg
gagagggtag tggtgagcat tgaccgtttt ttgagaatcc gggaccaacg aggaaatgta
ctactgtctc ccgaggaggt cagtgaaaca cagggaacag agaaactgac aataacttac
tcatcgtcaa tgatgtggga gattaatggt cctgaatcag tgttggtcaa tacctatcaa
tggatcatca gaaactggaa aactgttaaa attcagtggt cccagaaccc tacaatgcta
tacaataaaa tggaattgaa accatttcag tctttagtac ctaagccat tagaggccaa
tacagtgggt ttgtaagaac tctgttccaa caaatgaggg atgtgcttgg gacatttgat
acgcaacaga taataaaact tcttccctte gcagccgctc caccaaagca aagtagaatg
cagttctcct cattactgt gaatgtgagg ggatcaggaa tgaaatact tgtaagggc
aattctcctg tattcaacta taacaaggcc acgaagagac tcacagttct cggaaaggat
gctggcactt taactgaaga cccagatgaa ggcacagctg gagtggagtc cgctgttctg
agggattcc tcattctggg caaagaagac aagagatatg ggccagcact aagcatcaat
gaactgagca accttgcaa aggagagaag gctaatgtgc taattgggca aggagacgtg
gtgttggtaa tgaaacgaa acgggactct agcatactta ctgacagcca gacagcgacc
aaagaattc ggatggccat caattagtgt cgaatagttt aaaaacgacc ttgtttctac
t SEQ ID NO: 4
agcaaaagca gggtagataa tcactcactg agtgacatca aaatcatggc gtctcaaggc
accaaacgat cttacgaaca gatggagact gatggagaac gccagaatgc cactgaaatc
agagcatccg tggaaaaat gattggtgga attggacgat tctacatcca aatgtgcacc
gaactcaaac tcagtgatta tgagggacgg ttgatccaaa acagcttaac aatagagaga
atggtgctct ctgcttttga cgaaaggaga aataaatacc ttgaagaaca tcccagtgcg
gggaaagatc ctaagaaaac tggaggacct atatacagga gagtaaacgg aagtgggatg
agagaactca cctttatga caaagaagaa ataaggcgaa tctggcgcca agctaataat
ggtgacgatg caacggctgg tctgactcac atgatgatct ggcattcca tttgaatgat
gcaacttatc agaggacaag agctcttgtt cgcacggaa tggatccaag gatgtgctct
ctgatgcaag gttcaactct ccctaggagg tctgagccg caggtgctgc agtcaaagga
gttggaacaa tggtgatga attggtcaga atgatcaaac gtgggatca tgatcggaac
ttctggaggg gtgagaatgg acgaaaaca agaattgctt atgaagaat gtgcaacatt
ctcaaaggga aatttcaaac tgctgcacaa aaagcaatga tggatcaagt gagagagagc
cggaacccag ggaatgctga gttcgaagat ctcacttttc tagcacggtc tgcactcata
ttgagagggt cggttgctca caagtcctgc ctgcctgct gtgtgtatgg acctgccgta
gccagtgggt acgactttga aaggaggga tactctctag tggaataga cctttcaga
ctgcttcaaa acagccaagt gtacagccta atcagaccaa atgagaaatco agcacacaag
agtcaactgg tgtggatggc atgccattct gccgcatttg aagatctaag agtattaagc
ttcatcaaag ggacgaaggt gctcccaaga ggaagcttt cactagagg agtcaaatt
gcttccaatg aaaatatgga gactatggaa tcaagtacac ttgaactgag aagcaggtac
tgggccataa agaccagaag tggaggaaac accaatcaac agagggcat gggggccaa
atcagcatac aaactaogtt ctcagtacag agaaatctcc ctttgacag aacaaccatt
atggcagcat tcaatgggaa tacagagggg agaacatctg acatgaggac cgaaatcata
aggatgatgg aaagtgcaag accagaagat gtgtctttcc aggggcggg agtcttcgag
ctctcggacg aaaaggcagc gagccgatc gtgccttcct ttgacatgag taatgaagga
tcttatttct tcggagacaa tgcagaggag tacgacaatt aaagaaaat acccttgttt
ctact SEQ ID NO: 5
agcaaaagca ggtagatatt gaaagatgag tcttctaacc gaggtcgaaa cgtacgtact
ctctatcatc ccgtcaggcc cctcaaagc cgagatcgca cagagacttg aagatgtctt
tgcagggaag aacaccgatc ttgaggttct catggaatgg ctaaagacaa gaccaatcct
gtcacctctg actaagggga tttaggatt tgtgttcacg ctcaccgtgc ccagtgagcg
aggactgcag cgtagacgct ttgtccaaaa tgcccttaat gggaacgggg atccaaataa
catggacaaa gcagttaaac tgtataggaa gctcaagagg gagataacat tccatggggc
caaagaaatc tcactcagtt attctgctgg tgcacttgcc agttgtatgg gcctcatata
caacaggatg gggctgtga ccactgaagt ggcatttggc ctggtatgtg caacctgtga
```

FIGURE 2C

```
acagattgct gactcccagc atcggtctca taggcaaatg gtgacaacaa ccaatccact    540
aatcagacat gagaacagaa tggttttagc cagcactaca gctaaggcta tggagcaaat    600
ggctggatcg agtgagcaag cagcagaggc catggaggtt gctagtcagg ctagacaaat    660
ggtgcaagcg atgagaacca ttggactca tcctagctcc agtgctggtc tgaaaaatga    720
tcttcttgaa aatttgcagg cctatcagaa acgaatgggg gtgcagatgc aacggttcaa    780
gtgatcctct cactattgcc gcaaatatca tggatcttt gcacttgaca ttgtggattc    840
ttgatcgtct tttttcaaa tgcattacc gtgctttaa atacggactg aaaggagggc       900
cttctacgga aggagtgcca aagtctatga gggaagaata tcgaaaggaa cagcagagtg    960
ctgtggatgc tgacgatggt cattttgtca gcatagagct ggagtaaaaa actacttgt   1020
ttctact                                                             1027

SEQ ID NO: 6
agcaaaagca gggtgacaaa aacataatgg atccaaacac tgtgtcaagc tttcaggtag     60
attgctttct ttggcatgtc cgcaaacgag ttgcagacca agaactaggc gatgcccat     120
tcctgatcg gcttcgccga gatcagaaat cctaagagg aagtggcagt actctcggtc      180
tggacatcaa gacagccaca cgtgctggaa agcagatagt ggagcggatt ctgaaagaag    240
aatcgatga ggcacttaaa atgaccatgg cctctgtacc tgcgtcggt tacctaactg      300
acatgactct tgaggaaatg tcaagggact ggtccatgct catacccaag cagaaagtgg    360
caggccctct ttgtatcaga atggaccagg cgatcatgga taagaacatc atactgaaag    420
cgaacttcag tgtgattttt gacggctgg agactctaat attgctaagg gcttttcaccg    480
aagagggagc aatgtttggc gaaatttcac cattgccttc tcctccagga catactgctg    540
aggatgtgaa aaatgcagtt ggagtcctca tggaggact tgaatggaat gataaacag      600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga gataacaga gaatagttt     780
gagcaaataa cattatgca agccttacat ctattgcttg aagtggagca agagataaga    840
actttctcgt ttcagttat ttagtactaa aaaacaccct tgtttctact                890

SEQ ID NO: 7
agcaaaagca gggaaaaata aaaacaacca aaatgaaggc aaacctactg gtcctgttat     60
gtgcacttgc agctgcagat gcagacacaa tatgtatagg ctaccatgcg aacaattcaa    120
ccgacactgt tgacacagta ctcgagaaga atgtgacagt gacacactct gttaacctgc    180
tcgaagacag ccacaacgga aaactatgta gattaaaagg aatagcccca ctacaattgg    240
ggaaatgtaa catcgccgga tggctcttgg gaaacccaga atgcgaccca ctgcttccag    300
tgagatcatg tcctacatt gtagaaacac caaactctga atggaata tgttatccag      360
gagattcat cgactatgag gagctgaggg agcaattgag ctcagtgtca tcattcgaaa    420
gattcgaaat atttcccaaa gaaagctcat ggcccaacca caacacaaac ggagtaacgg    480
cagcatgctc ccatgagggg aaaagcagtt tttacagaaa ttgctatggg ctgacggaga    540
aggagggctc atacccaaag ctgaaaatt cttatgtgaa caaaaaggg aaagaagtcc      600
ttgtactgtg ggtattcat caccgcta acagtaagga acaacagaat ctctatcaga       660
atgaaaatgc ttatgtctct gtagtgactt caattataa caggagatt accggaaaa      720
tagcagaaag acccaaagta agagatcag cgggaggat gaactattac tggaccttgc     780
taaaaccggg agacacaata atattgaag caaatggaaa tctaatagca ccaatgtatg    840
cttcgcact gagtagaggc tttgggtcg gcatcatcac ctcaaacgca tcaatgcatg     900
agtgtaacac gaagtgtca acaccctgg agctataaa cagcagtctc cctaccaga     960
atatacaccc agtcacaata ggagagtgcc caaatacgt caggagtgcc aaattgagga   1020
tggttacagg actaaggaac attccgtcca ttcaatccag aggtctattt ggagccattg   1080
ccggttttat tgaaggggga tggactggaa tgatagatgg atggtatggt tatcatcatc   1140
agaatgaaca gggatcaggc tatgcagcgg atcaaaaaag cacacaaaat gccattaacg   1200
ggattacaa caaggtgaac actgttatcg agaaatgaa cattcaattc acagctgtgg   1260
gtaagaatt caacaatta gaaaaagga tggaaatt aataaaaaa gttgatgatg         1320
gattctgga cattggaca tataatgcag aattgttagt tctactgaa aatgaaagga      1380
ctctggattt ccatgactca aatgtgaaga atctgtatga gaaagtaaaa agccaattaa   1440
```

FIGURE 2D

```
agaataatgc caagaaaatc ggaaatggat gttttgagtt ctaccacaag tgtgacaatg    1500
aatgatgga aagtgtaaga aatgggactt atgattatcc caaatattca gaagagtcaa    1560
agttgaacag ggaaaaggta gatggagtga aattggaatc aatgggatc tatcagattc    1620
tggcgatcta ctcaactgtc gccagttcac tggtgctttt ggtctcctg ggggcaatca    1680
gtttctggat gtgttctaat ggatctttgc agtgcagaat atgcatctga gattagaatt    1740
tcagagatat gaggaaaaac accttgttt ctact                                1775

SEQ ID NO: 8
agcaaaagca gggtttaaa atgaatccaa atcagaaaat aataaccatt ggatcaatct       60
gtctggtagt tggactaatt agcctaatat tgcaaatagg gaatataatc tcaatacgga     120
ttagccattc aattcaaact ggaagtcaaa accatactgc aatatgcaac caaaacatca     180
ttacctataa aaatagcacc tgggtaaagg cacaaacttc agtgatatta acggcaatt      240
catctctttg tccatccgt gggtggcta tatacagcaa agacaatago ataagaattg       300
gttccaaagg agacgttttt gtcataagag agccctttat tcatgttct cacttggaat     360
gcaggacctt ttttctgacc caaggtgcct tactgaatga caagcattca agtgggactg     420
ttaaggacag aagccttat agggccttaa tgagctgcc tgtcggtgaa gctccgtccc      480
cgtacaattc aagatttgaa tcggctgctt ggtcagcaag tcatgtcat gatggcatgg     540
gctggctaac aatcgagaatt tcaggtccag ataatggagc agtggctgta ttaaaatcca     600
acggcataat aactgaaacc ataaaaagtt ggaggaagaa aatattgagg acacaagagt     660
ctgaatgtgc ctgtgtaaat ggttcatgtt ttactataat gactgatggc ccagtgatg     720
ggctggcctc gtacaaaatt tcaagatcg aaaaggggaa ggttactaaa tcaatagagt     780
tgaatgcacc taattctgac tatgaggaat gttctgtta cctgataccc ggcaaagtga     840
tgtgtgtgtg cagagagag tggaacggcc atgggtgtct ttcgatcaaa              909
acctggatta tcaaatagga tacatctgca gtgggtttt cggtgacaac ccgcgtcccg     969
aagatggaac aggcagctgt ggtccagtgt atgttgatgg agcaaaacga gtaaagggat    1020
tttcatatag gtatggtaat ggtgtttgga taggaaggac caaaagtcac agttccagac    1080
atgggttgga gatgattgg gatcctaatg gatggacaga gactgatagt aagtctctcg    1140
tgaggcaaga tgttgtggca atgactgatt ggtcagggta tagcggaagt ttcgttcaac    1200
atcctgagct gacaggcta gactgtatga ggccgtgctt ctgggttgaa ttaatcaggy    1260
gacgacctaa agaaaaaca atctggacta gtgcgagcag catttcttt tgtggcgtga    1320
atagtgatac tgtagattgg tcttggccag acggtgctga gttgccattc agcattgaca    1380
agtagtctgt tcaaaaaact cctgttcct act                                 1413

SEQ ID NO: 10
agcgaaagca ggtcaattat attcaaatatg gaaagaataa aagaactaag aaatctaatg      60
tgcagtctc gcaccgcga gatactcaca aaaaccaccg tggaccatat ggccataatc        120
aagaagtaca catcaggaag acaggagaag aaccagcac ttaggatgaa atggatgatg        160
gcaatgaaat atccaattac agcagacaag aggataaacg aaatgattcc tgagagaaat       240
gagcaaggac aaactttatg gagtaaaatg aatgatgccg gatcagaccg agtgatggta       300
tcacctctgg ctgtgacatg gtggaatagg aatggaccaa tgacaaatac agttcattat       360
ccaaaaatct acaaactta ttttgaaaga gtcgaaaggc taaagcatgg aacctttgc        420
cctgtccatt ttagaaacca agtcaaaata cgtcggagag ttgacataaa tcctggtcat       460
gcagatctca gtgccaagga ggcacaggat gtaatcatgg aagttgttt ccctaacgaa       540
gtgggagcca ggatactaac atggaatcg caactaacga taccaaaga gaagaagaa         600
gaactccagg attgcaaaat tctcctttg atggttgcat acatgttgga gagagaactg       660
gtccgcaaaa cgagattcct cccagtggct ggtggaacaa gcagtgtgta cattgaagtg       720
ttgcatttga ctcaaggaac atgctgggaa cagatgtata cccaggagg gaagtgaag         780
aatgatgatg ttgatcaaag cttgattatt gctgctagga acatagtgag aagagctgca       840
gtatcagcag accactaagc atcttattg gagatgtgcc acagcacaca gattggtgga       900
attaggatgc tagacatcct taagcagaac ccaacagaag gcaagcgt ggatatgc           960
aagtctgcaa tggactgag aattagctca tcttcagtt tggtggatt cacatttaag          1020
agaacaagcg gatcatcagt caagagagag gaagaggtgc ttacgggca tctcaaaca        1080
ttgaagataa gagtgcatga gggatctgaa gagttcacaa tggttggag aagagcaaca       1140
gccatactca gaaaagcaac caggagattg attcagctga tagtgagtgg agagacgaa        1200
```

FIGURE 2E

```
cagtcgattg ccgaagcaat aattgtggcc atgtatttt cacaagagga ttgtatgata 1260
aaagcagtta gaggtgatct gaatttcgtc aataggcga atcagcgact gaatcctatg 1320
catcaacttt taagacattt tcagaaggat gcgaaagtgc ttcttcaaaa ttggggagtt 1380
gaacctatcg acaatgtgat gggaatgatt gggatattgc ccgacatgac tccaagcatc 1440
gagatgtcaa tgagaggagt gagaatcagc aaaatgggtg tagatgagta ctccagcacg 1500
gagagggtag tggtgagcat tgaccggttc ttgagggtca gggaccaacg aggaaatgta 1560
ctactgtctc ccgaggaggt cagtgaaaca cagggaacag agaaactgac aataacttac 1620
tcatcgtcaa tgatgtggga gattaatggt cctgaatcag tgttggtcaa tacctatcaa 1680
tggatcatca gaaactggga aactgttaaa attcagtggt cccagaaccc tacaatgcta 1740
tacaataaaa tggaatttga accatttcag tcttagtac ctaaggcat tagaggccaa 1800
tacagtgggt ttgtcagcac tctgttccaa caaatgaggg atgtgcttgg gacatttgat 1860
acggacaga taataaact tcttccttc gcagccgctc caccaaagca aagtagaatg 1920
cagttctcct catttactgt gaatgtgagg ggatcaggaa tgaactact tgtaaggggc 1980
aattctcctg tattcaacta caacaaggcc acgaagagac tcacagttct cggaaaggat 2040
gctggcactt taacgaaga cccagatgaa ggcacagctg gagtggagtc cgctgttctg 2100
agggattcc tcattctggg caaagaagac aggagatatg ggcagcatt aagcatcaat 2160
gaactgagca accttgcgaa aggagagaag gctaatgtgc taattgggca aggagacgtg 2220
gtgtggtaa tgaaacgaaa acgggactct agcatactta ctgacagcca gacagcgacc 2280
aaaagaattc ggatggccat caattagtgt cgaatagttt aaaaacgacc ttgtttctac 2340
t                                                                 2341

SEQ ID NO: 11
agcgaaagca ggcaaaccat ttgaatggat gtcaatccga ccttacttt cttaaaagtg  60
ccagcacaaa atgctataag cacaactttc cctatacg gagacctc ttacagccat  120
gggacaggaa caggatacac catggatact gtcaacagga cacatcagta ctcagaaaag 180
ggaagatgga caacaaacac cgaaactgga gcaccgcaac tcaacccgat tgatgggcca 240
ctgccagaag acaatgaacc aagtggttat gcccaaacag attgtgtatt ggaagcaatg 300
gctttccttg aggaatccca tcctggtatt ttgaaaact cgtgtattga acgatggag  360
gttgttcagc aaaacacgagt agacaagctg acacaaggcc gacagaccta tgactggact 420
ttaaatagaa accagcctgc tgcaacagca ttggccaaca caataagagt gttcagatca 480
aatggcctca aggccaatga tcaggaaggg ctaagagact tccttaaggt tgtaatggag 540
tcaatgaaaa aagaagaaat ggggatcaca actcatttc agagaaagag acgggtgaga 600
gccaatatga ctaagaaaat gataacacag agaacaatag taaaggaa acagagattg 660
aacaaaggg gttatctaat tagagcattg accctgaaca caatgaccaa agatgctgag 720
agagggaagc taaaacggag agcaattgca acccaggga tgcaaataag gggtttgta 780
tactttgttg agacactggc aaggagtata tgtgagaaac ttgaacaatc agggttgcca 840
gttggaggca atgagaagaa agcaaagttg gcaaatgttg taaggaagat gatgaccaat 900
tctcaggaca ccgaactttc tttcaccatc actggagata caccaaatg gaacgaaat 960
cagaatctcc ggatgttttt ggccatgatc acatatatga ccagaaatca gcccgaatgg 1020
ttcagaaatg ttctaagtat tgctccaata atgttctcaa acaaaatggc gagactggga 1080
aagggtata tgttgaccaa gagtatact cagacttagt ttagatttcca aacaaatgga 1140
ctagcaaagca ttgatttgaa atatttcaat gattcaacaa gaaagaagat tgaaaaatc 1200
cgaccgctct taatagaggg gactgcatca ttgagccctg aatgatgat gggcatgttc 1260
aatatgttaa gcactgtatt agcgtctcc atctgaatc ttggacaaaa gagatacacc 1320
aagactactt actggtgga tggtcttcaa tcctctgacg atttgctct gattgtgaat 1380
gcaccaatc atgaaggat tcagcgga gtgacaggt ttatcgaac tgtaagcta 1440
cttggaatca atatgagcaa gaaaagtct acataaaca gaacaggtac atttgaattc 1500
acaagtttt tctatcgtta tgggttttgt gcaattca gcatggagct tccagttttt 1560
ggggtgtctg ggatcaacga gtcagcgac atgagtattg gagttactgt catcaaaaac 1620
aatatgataa acaatgatct tggtccagca acagctcaa tggccttca gttgttcatc 1680
aagattaca ggtacaagta ccgatgccat agaggtgaca caaaataca accccgaaga 1740
tcattgaaa taagaaact gtgggagcaa accgttcca agctgggact gctggtctcc 1800
gacggaggcc caaatttata caacattaga aatctccaca ttcctgaagt ctgcctaaaa 1860
tgggaattga tggatgagga ttaccagggg cgtttatgca acccactgaa cccatttgtc 1920
```

```
agccataaag aaattgaatc aatgaacaat gcagtgatga tgccagcaca tggtccagcc    1980
aaaaacatgg agtatgatgc tgttgaaaca acaactcct ggatcccaa aagaaatcga     2040
tccatcttga atacaagtca aagaggagta cttgaagatg aacaaatgta ccaaaggtgc    2100
tgcaatttat ttgaaaaatt cttccccagc agttcataca gaagaccagt cgggatatcc    2160
agtatggtgg aggctatggt ttccagagcc cgaattgatc cacggattga tttcgaatct    2220
ggaaggataa agaaagaaga gttcactgag atcatgaaga tctgttccac cattgaagag    2280
ctcagacggc aaaaatagtg aatttagctt gtccttcatg aaaaaatgcc ttgtttctac    2340
t                                                                    2341

SEQ ID NO: 12
agcgaaagca ggtactgatt caaaatggaa gatttttgtgc gacaatgctt caatccgatg    60
attgtcgagc ttgcggaaaa aaccatgaaa gagtatgggg aggacctgaa aatcgaaaca    120
aacaaattg cagcaatatg cactcacttg gaagtatgct tcatgtattc agatttccac    180
ttcatcaatg agcaaggcga gtcaataatc gtagaacttg gtgatcctaa tgcacttttg    240
aagcacagat ttgaaataat cgagggaaga gatcgcacaa tggcctggac agtagtaaac    300
agtatttgca acactacagg ggctgagaaa ccaagtttc taccagattt gtatgattac    360
aaggaaaata gattcatcga aattggagta acaaggagag aagttcacat atactatctg    420
gaaaaggcca ataaaattaa atctgagaaa acacacatcc acattttctc gttcactggg    480
gaagaaatgg ccacaaggac cgactacact ctcgatgaag aaagcagggc taggatcaaa    540
accaggctat tcaccataag acaagaaatg gccagcagag gcctctggga ttcctttcgt    600
cagtccgaga gaggagaaga gacaattgaa gaaagtttg aaatcacagg aacaatgcga    660
aagcttgccg accaaagtct ccgccgaac ttctccagcc ttgaaaattt tagagcctat    720
gtggatggat tcgaaccgaa cggctacatt gagggcaagc tgtctcaaat gtccaaagaa    780
gtaaatgcta gaattgaacc ttttttgaaa acaacaccac gaccacttag acttccgaat    840
gggcctccct gttctcagcg gtccaaattc ctgctgatgc atgccttaaa attaagcatt    900
gaggaccaa gtcatgaagg agggaaata ccgctatatg atgcaatcaa atgcatgaga    960
acactctttg gatggaagga accaatgtt gttaaacac acgaaaaggg aataaatcca    1020
aattatcttc tgtcatggaa gcaagtactg gcagaactgc aggacattga gaatgaggag    1080
aaaattccaa agactaaaaa tatgaaaaaa acaagtcagc taaagtggc actggtgag    1140
aacatggcac cagaaaggt agactttgac gactgtaaag atgtaggtga tttgaagcaa    1200
tatgatagtg atgaaccaga attgaggtcg ctgcaagtt ggattcagaa tgagttcaac    1260
aaggcatgcg aactgacaga tcaagctgg atagagcttg atgagattgg agaagatgtg    1320
gctccaattg aacacattgc aagcatgaga aggaattatt tcacatcaga ggtgtctcac    1380
tgcagagcca cagaatacat aatgaagggg gtgtacatca atactgcctt actaatgca    1440
tctttgtgcag caatggaatc tttccaatta attcatga taagcaagtg tagaactaag    1500
gagggaagcc gaaagaccaa cttgtatggt ttcatcataa aaggaaagatc acacttaagg    1560
aatgacaccg acgtggtaaa cttgtgagc atggagtttt ctctcactga cccaagactt    1620
gaaccacaca atggagaaa gtactgtgtt cttgagtag agatatgct tctaagaagt    1680
gccataggcc aggtttcaag gccatgttc ttgtatgtga ggacaaatgg aacctcaaaa    1740
attaaaatga aatggggaat ggagatgaag cgttgtctcc tccagtcact tcaacaaatt    1800
gagagtatga ttgaactga gtcctctgtc aaagagaaag acatgaccaa agagttctct    1860
gagacaaat cagaaacatg gccattgga gagtctccca aggagtggga gaaagttcc    1920
attgggaagg tctgcaggac tttattagca aagtcggtat taacagctt gtatgcatct    1980
ccacaactag aaggattttc agctgaatca agaaactgc ttcttatcgt tcaggctctt    2040
agggacaatc tggaactgg gactttgat cttggggggc tatatgaagc aattgaggag    2100
tgcctaatta atgatccctg ggttttgctt aatgcttctt ggttcaactc cttccctaca    2160
catgcattga gttagttgtg gcagtgctac tattgctat ccatactgtc caaaaagta    2220
cctgttcct act                                                        2233

SEQ ID NO: 13
agcaaaagca gggtagataa tcactcactg agtgacatca aaatcatggc gtccaaggc     60
accaaacggt cttacgaaca gatggagact gatggagaac gccagaatgc cactgaaatc    120
agagcatccg tcggaaaaat gattgatggg attggacgat tctacatcca aatgtgcaca    180
```

FIGURE 2G

```
gaacttaaac tcagtgatta tgagggacgg ttgatccaaa acagcttaac aatagagaga   240
atggtgctct ctgctttga cgaaggaga aataaatacc tggaagaaca tcccagtgcg    300
gggaaagatc ctaagaaaac tggaggacct atatacagaa gagtaaacgg aaagtggatg   360
agagaactca tcctttatga caaagaagaa ataaggcgaa tctggcgcca agtaataat    420
ggtgacgatg caacggctgg tctgactcac atgatgatct ggcattccaa tttgaatgat   480
gcaacttatc agaggacaag ggctcttgtt cgcaccggaa tggatccag gatgtgctct    540
ctgatgcaag gttcaactct ccctaggagg tctggagccg caggtgctgc agtcaaagga   600
gttggaacaa tggtgatga attggtcagg atgatcaaac gtggatcaa tgatcggaac    660
ttctggaggg gtgagaatgg acgaaaaaca gaattgcttt atgaagaat gtgcaacatt    720
ctcaaaggga aatttcaaac tgctgcacaa aagcaatga tggatcaagt gagagagagc    780
cggaaccag ggaatgctga gttcgaagat ctacttttc tagcacggtc tgcactcata    840
ttgagagggt cggttgctca caagtcctgc ctgcctgcct gtgtgtatgg acctgccgta   900
gccagtgggt acgactttga agagagagga tactctctag tcggaataga ccctttcaga   960
ctgcttcaaa acagccaagt gtacagccta atcagaaaac atgagaatcc agccacacaag  1020
agtcaactgg tgtggatggc atgccattct gccgcatttg aagatctaag agtattgagc   1080
ttcatcaaag ggacgaaggt ggtcccaaga ggaagctttc ccactagagg agttcaaatt   1140
gcttccaatg aaaatatgga gactatggaa tcaagtacac ttgaactgag aagcaggtac   1200
tgggccataa ggaccagaag tggagaaac accaatcaac agaggcatc tgcgggccaa    1260
atcagcatac aacctacgtt ctcagtacag agaaatctcc cttttgacag aacaacgtt    1320
atggcagcat tcactgggaa tacagagggg agaacatctg acatgaggac cgaaatcata   1380
aggatgatgg aaagtgcaag accagaagat gtgtctttcc agggcgggg agtcttcgag    1440
ctctcggacg aaaaggcagc gagcccgatc gtgccttcct tgacatgag taacgaagga   1500
tcttattct tcggagacaa tgcagaggag tacgacaatt aaagaaaat acccttgttt     1560
ctact                                                              1565

SEQ ID NO: 14
agcaaaagca ggtagatatt gaaagatgag tcttctaacc gaggtcgaaa cgtacgttct   60
ctctatcatc ccgtcaggcc ccctcaaagc cgagatcgca cagagacttg aagatgtctt  120
tgcagggaag aacaccgatc ttgaggttct catggaatgg ctaaagacaa gaccaatcct  180
gtcacctctg actaagggga tttaggatt tgtgttcacg ctcaccgtgc ccagtgagcg  240
aggactgcag cgtagacgct ttgtccaaaa tgccttaat gggaacgggg atcaaataa   300
catggacaaa gcagttaaac tgtataggaa gctcaagagg gagataacat tccatgggc   360
caaagaaatc tcactcagtt attctgctgg tgcacttgcc agttgtatgg gcctcatata   420
caacaggatg ggggctgtga ccactgaagt ggcatttggt ctggtatgtg caacctgtga   480
acagattgct gactccagc atggtctca taggcaaatg gtgacaacaa ccaacccact   540
aatcagacat gagaacagaa tggttctagc cagcactaca gctaaggcta tggagcaaat  600
ggctggatcg agtgagcaag cagcagaggc catggaggtt gctagtcagg ctaggcaaat  660
ggtgcaagcg atgagaacca ttggactca tcctagctcc agtgctggtc tgaaaaatga   720
tcttcttgaa aattttgcagg cctatcagaa acgaatgggg gtgcagatgc aacggttcaa  780
gtgatcctct cgctattgcc gcaaatatca ttggatctt gcacttgata ttgtggattc   840
ttgatcgtct ttttttcaaa tgcatttacc gtcgttttaa ataggactg aaaggaggc    900
cttctacgga aggagtgcca aagtctatga ggaagaata tgaaaggaa cagcagagtg   960
ctgtggatgc tgacgatggt catttgtca gcatagagct ggagtaaaaa actaccttgt  1020
ttctact                                                           1027

SEQ ID NO: 15
agcaaaagca gggtgacaaa gacataatgg atccaaacac tgtgtcaagc tttcaggtag   60
attgcttct tggcatgtc cgcaaacgag ttgcagacca agaactaggt gatgccccat   120
tccttgatcg gcttcgccga gatcagaaat ccctaagagg aaggggcagc actcttggtc   180
tggacatcga gacagcaca cgtgctggaa agcagatagt ggagcggatt ctgaaagaag   240
aatccgatga ggcacttaaa atgaccatgg cctctgtacc tgctgcggt tacctaaccg   300
acatgactct tgaggaaatg tcaagggaat ggtccatgct cataccaag cagaaagtgg   360
caggccctct ttgtatcaga atggaccagg cgatcatgga taaaaacatc atactgaaag   420
cgaacttcag tgtgattttt gaccggctgg agactctaat attgctaagg gctttcaccg   480
aagggggagc aattgttgc gaaatttgac cattgcctc tcttccagga catactgctg    540
```

```
aggatgtcaa aaatgcagtt ggagtcctca tcggaggact tgaatggaat gataacacag    600
ttgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga aggtaacaga gaatagtttt    780
gagcaaataa catttatgca agccttacat ctattgcttg aagtggagca agagataaga    840
actttctcat ttcagcttat ttaataataa aaaacaccct tgtttctact               890
```

Fig 11. PB2KO virus expressing pspA of pneumococcus

Fig 12. Growth kinetics of PB2KO-PspA virus

Survival post-challenge with Influenza virus

Survival post-challenge with pneumococcus

SEQUENCE LISTING

```
<160> NUMBER OF SEQ ID NOS: 16

<210> SEQ ID NO 1
<211> LENGTH: 2233
<212> TYPE: DNA
<213> ORGANISM: Artificial Sequence
<220> FEATURE:
<223> OTHER INFORMATION: A synthetic oligonucleotide

<400> SEQUENCE: 1
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
```

-continued

```
aacaaatttg cagcaatatg cactcacttg gaagtatgct tcatgtattc agattttcac      180
ttcatcaatg agcaaggcga gtcaataatc gtagaacttg gtgatccaaa tgcacttttg      240
aagcacagat ttgaaataat cgagggaaga gatcgcacaa tggcctggac agtagtaaac      300
agtatttgca acactacagg ggctgagaaa ccaaagtttc taccagattt gtatgattac      360
aaggagaata gattcatcga aattggagta acaaggagag aagttcacat atactatctg      420
gaaaaggcca ataaaattaa atctgagaaa acacacatcc acattttctc gttcactggg      480
gaagaaatgg ccacaaaggc agactacact ctcgatgaag aaagcagggc taggatcaaa      540
accagactat tcaccataag acaagaaatg ccagcagag gcctctggga ttcctttcgt       600
cagtccgaga gaggagaaga gacaattgaa gaaaggtttg aaatcacagg aacaatgcgc      660
aagcttgccg accaaagtct cccgccgaac ttctccagcc ttgaaaattt tagagcctat      720
gtggatggat tcgaaccgaa cggctacatt gagggcaagc tgtctcaaat gtccaaagaa      780
gtaaatgcta gaattgaacc ttttttgaaa caacaccac gaccacttag acttccgaat       840
gggcctccct gttctcagcg gtccaaattc ctgctgatgg atgccttaaa attaagcatt      900
gaggacccaa gtcatgaagg agagggaata ccgctatatg atgcaatcaa atgcatgaga      960
acattctttg gatggaagga acccaatgtt gttaaaccac acgaaaaggg aataaaatcca    1020 aattatcttc tgtcatggaa gcaagtactg gcagaactgc aggacattga gaatgaggag     1080
aaaattccaa agactaaaaa tatgaagaaa acaagtcagc taaagtgggc acttggtgag     1140
aacatggcac cagaaaaggt agactttgac gactgtaaag atgtaggtga tttgaagcaa     1200
tatgatagtg atgaaccaga attgaggtcg cttgcaagtt ggattcagaa tgagtttaac     1260
aaggcatgcg aactgacaga ttcaagctgg atagagctcg atgagattgg agaagatgtg     1320
gctccaattg aacacattgc aagcatgaga aggaattatt tcacatcaga ggtgtctcac     1380
tgcagagcca cagaatacat aatgaaggga gtgtacatca atactgcctt gcttaatgca     1440
tcttgtgcag caatggatga tttccaatta attccaatga taagcaagtg tagaactaag     1500
gagggaaggc gaaagaccaa cttgtatggt ttcatcataa aggaagatc ccacttaagg      1560 aatgacaccg acgtggtaaa cttttgtgagc atggagtttt ctctcactga cccaagactt    1620
gaaccacata aatgggagaa gtactgtgtt cttgagatag agatatgct tataagaagt      1680 gccataggcc aggtttcaag gcccatgttc ttgtatgtga gaacaaatgg aacctcaaaa     1740
attaaaatga atgggggaat ggagatgagg cgttgcctcc tccagtcact tcaacaaatt     1800
gagagtatga ttgaagctga gtcctctgtc aaagagaaag acatgaccaa agagttcttt     1860
gagaacaaat cagaaacatg gcccattgga gagtccccca aaggagtgga ggaaagttcc     1920
attgggaagg tctgcaggac tttattagca agtcggtat tcaacagctt gtatgcatct      1980
ccacaactag aaggattttc agctgaatca agaaaactgc ttcttatcgt tcaggctctt     2040
agggacaacc tggaacctgg gacctttgat cttgggggc tatatgaagc aattgaggag      2100
tgcctgatta atgatccctg ggttttgctt aatgcttctt ggttcaactc cttccttaca     2160
catgcattga gttagttgtg gcagtgctac tatttgctat ccatactgtc caaaaaagta     2220
ccttgtttct act                                                         2233
```

<210> SEQ ID NO 2
<211> LENGTH: 2341
<212> TYPE: DNA
<213> ORGANISM: Artificial Sequence
<220> FEATURE:
<223> OTHER INFORMATION: A synthetic oligonucleotide

```
<400> SEQUENCE: 2
agcgaaagca ggcaaaccat ttgaatggat gtcaatccga ccttactttt cttaaaagtg      60
ccagcacaaa atgctataag cacaactttc ccttatactg gagaccctcc ttacagccat     120
gggacaggaa caggatacac catggatact gtcaacagga cacatcagta ctcagaaaag     180
ggaagatgga caacaaacac cgaaactgga gcaccgcaac tcaacccgat tgatgggcca     240
ctgccagaag acaatgaacc aagtggttat gcccaaacag attgtgtatt ggaggcgatg     300
gctttccttg aggaatccca tcctggtatt tttgaaaact cgtgtattga acgatggag      360 gttgttcagc aaaacacgag tagacaagct acacaaggcc gacagaccta tgactggact     420
ctaaatagaa accaacctgc tgcaacagca ttggccaaca caatagaagt gttcagatca     480
aatggcctca cggccaatga gtctggaagg ctcatagact tccttaagga tgtaatggag     540
tcaatgaaca aagaagaaat ggggatcaca actcattttc agagaaagag acgggtgaga     600
gacaatatga ctaagaaaat gataacacag agaacaatgg gtaaaagaa gcagagattg      660 aacaaaagga gttatctaat tagagcattg accctgaaca caatgaccaa agatgctgag     720
agagggaagc taaacggag agcaattgca accccaggga tgcaaataag ggggtttgta     780
tactttgttg agacactggc aaggagtata tgtgagaaac ttgaacaatc agggttgcca     840
gttggaggca atgagaagaa agcaaagttg gcaaatgttg taaggaagat gatgaccaat     900
tctcaggaca ccgaactttc tttcaccatc actggagata caccaaatg gaacgaaaat     960 cagaatcctc ggatgttttt ggccatgatc acatatatga ccagaaatca gcccgaatgg    1020
ttcagaaatg ttctaagtat tgctccaata atgttctcaa acaaatggc gagactggga     1080 aaagggtata tgtttgagag caagagtatg aacttagaa ctcaaatacc tgcagaaatg     1140
ctagcaagca tcgatttgaa atatttcaat gattcaacaa gaagaagat tgaaaaatc      1200 cgaccgctct aatagaggg gactgcatca ttgagccctg aatgatgat gggcatgttc      1260 aatatgttaa gcactgtatt aggcgtctcc atcctgaatc ttggacaaaa gagatacacc    1320
aagactactt actggtggga tggtcttcaa tcctctgacg attttgctct gattgtgaat    1380
gcacccaatc atgaagggat tcaagccgga gtcgacaggt tttatcgaac ctgtaagcta    1440
cttggaatca atatgagcaa gaaaaagtct tacataaaca gaacaggtac atttgaattc    1500
acaagttttt tctatcgtta tgggtttgtt gccaatttca gcatggagct tcccagtttt    1560
ggggtgtctg ggatcaacga gtcagcggac atgagtattg gagttactgt catcaaaaac    1620
aatatgataa acaatgatct tggtccagca acagctcaaa tggcccttca gttgttcatc    1680
aaagattaca ggtacacgta ccgatgccat ataggtgaca cacaaataca aacccgaaga    1740
tcatttgaaa taagaaact gtgggagcaa acccgttcca agctggact gctggtctcc    1800 gacggaggcc caaatttata caacattaga atctccaca ttcctgaagt ctgcctaaaa    1860
tgggaattga tggatgagga ttaccagggg cgtttatgca cccactgaa cccatttgtc     1920 agccataaag aaattgaatc aatgaacaat gcagtgatga tgccagcaca tggtccagcc    1980
aaaaacatgg agtatgatgc tgttgcaaca acacactcct ggatcccaa aagaaatcga     2040 tccatcttga atacaagtca agaggagta cttgaggatg aacaaatgta ccaaaggtgc    2100 tgcaattttat ttgaaaaatt cttccccagc agttcataca gaagaccagt cgggatatcc    2160
agtatggtgg aggctatggt ttccagagcc cgaattgatg cacggattga tttcgaatct    2220
ggaaggataa agaaagaaga gttcactgag atcatgaaga tctgttccac cattgaagag    2280
```

```
ctcagacggc aaaaatagtg aatttagctt gtccttcatg aaaaaatgcc ttgtttctac    2340
t                                                                   2341
```

<210> SEQ ID NO 3
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 3

```
agcgaaagca ggtcaattat attcaatatg gaaagaataa aagaactacg aaatctaatg      60
tcgcagtctc gcacccgcga gatactcaca aaaaccaccg tggaccatat ggccataatc     120
aagaagtaca catcaggaag acaggagaag aacccagcac ttaggatgaa atggatgatg     180
gcaatgaaat atccaattac agcagacaag aggataacgg aaatgattcc tgagagaaat     240
gagcaaggac aaactttatg gagtaaaatg aatgatgccg gatcagaccg agtgatggta     300
tcacctctgg ctgtgacatg gtggaatagg aatggaccaa taacaaatac agttcattat     360
ccaaaaatct acaaaactta ttttgaaaga gtcgaaaggc taaagcatgg aaccttggc     420
cctgtccatt ttagaaacca agtcaaaata cgtcggagag ttgacataaa tcctggtcat     480
gcagatctca gtgccaagga ggcacaggat gtaatcatgg aagttgtttt ccctaacgaa     540
gtgggagcca ggatactaac atcggaatcg caactaacga taaccaaaga gaagaaagaa     600
gaactccagg attgcaaaat ttctcctttg atggttgcat acatgttgga gagagaactg     660
gtccgcaaaa cgagattcct cccagtggct ggtggaacaa gcagtgtgta cattgaagtg     720
ttgcatttga ctcaaggaac atgctgggaa cagatgtata ctccaggagg ggaagtgagg     780
aatgatgatg ttgatcaaag cttgattatt gctgctagga acatagtgag aagagctgca     840
gtatcagcag atccactagc atctttattg gagatgtgcc acagcacaca gattggtgga     900
attaggatgg tagacatcct taggcagaac ccaacagaag agcaagccgt ggatatatgc     960
aaggctgcaa tgggactgag aattagctca tccttcagtt ttggtggatt cacatttaag    1020
agaacaagcg gatcatcagt caagagagag gaagaggtgc ttacgggcaa tcttcaaaca    1080
ttgaagataa gagtgcatga gggatatgaa gagttcacaa tggttgggag aagagcaaca    1140
gccatactca gaaaagcaac caggagattg attcagctga tagtgagtgg gagagacgaa    1200
cagtcgattg ccgaagcaat aattgtggcc atggtatttt cacaagagga ttgtatgata    1260
aaagcagtca gaggtgatct gaatttcgtc aatagggcga atcaacgatt gaatcctatg    1320
catcaacttt taagacattt tcagaaggat gcgaaagtgc tttttcaaaa ttggggagtt    1380
gaacctatcg acaatgtgat gggaatgatt gggatattgc ccgacatgac tccaagcatc    1440
gagatgtcaa tgagaggagt gagaatcagc aaaatgggtg tagatgagta ctccagcacg    1500
gagagggtag tggtgagcat tgaccgtttt ttgagaatcc gggaccaacg aggaaatgta    1560
ctactgtctc ccgaggaggt cagtgaaaca caggaacag agaaactgac aataacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg gacatttgat    1860
accgcacaga taataaaact tcttcccttc gcagccgctc caccaaagca agtagaatg    1920
cagttctcct catttactgt gaatgtgagg ggatcaggaa tgagaatact tgtaaggggc    1980
```

```
aattctcctg tattcaacta taacaaggcc acgaagagac tcacagttct cggaaaggat    2040
gctggcactt taactgaaga cccagatgaa ggcacagctg gagtggagtc cgctgttctg    2100
aggggattcc tcattctggg caaagaagac aagagatatg gccagcact aagcatcaat    2160 gaactgagca accttgcgaa aggagagaag gctaatgtgc taattgggca aggagacgtg    2220
gtgttggtaa tgaaacggaa acgggactct agcatactta ctgacagcca gacagcgacc    2280
aaaagaattc ggatggccat caattagtgt cgaatagttt aaaaacgacc ttgtttctac    2340
t                                                                   2341
```

<210> SEQ ID NO 4
<211> LENGTH: 1565
<212> TYPE: DNA
<213> ORGANISM: Artificial Sequence
<220> FEATURE:
<223> OTHER INFORMATION: A synthetic oligonucleotide

<400> SEQUENCE: 4

```
agcaaaagca gggtagataa tcactcactg agtgacatca aaatcatggc gtctcaaggc      60
accaaacgat cttacgaaca gatggagact gatggagaac gccagaatgc cactgaaatc     120
agagcatccg tcggaaaaat gattggtgga attggacgat tctacatcca aatgtgcacc     180
gaactcaaac tcagtgatta tgagggacgg ttgatccaaa acagcttaac aatagagaga     240
atggtgctct ctgcttttga cgaaaggaga aataaatacc ttgaagaaca tcccagtgcg     300
gggaaagatc ctaagaaaac tggaggacct atatacagga gagtaaacgg aaagtggatg     360
agagaactca tcctttatga caaagaagaa ataaggcgaa tctggcgcca agctaataat     420
ggtgacgatg caacggctgg tctgactcac atgatgatct ggcattccaa tttgaatgat     480
gcaacttatc agaggacaag agctcttgtt cgcaccggaa tggatcccag gatgtgctct     540
ctgatgcaag gttcaactct ccctaggagg tctggagccg caggtgctgc agtcaaagga     600
gttggaacaa tggtgatgga attggtcaga atgatcaaac gtgggatcaa tgatcggaac     660
ttctggaggg gtgagaatgg acgaaaaaca agaattgctt atgaaagaat gtgcaacatt     720
ctcaaaggga atttcaaac tgctgcacaa aagcaatga tggatcaagt gagagagagc     780
cggaacccag ggaatgctga gttcgaagat ctcactttc tagcacggtc tgcactcata     840
ttgagagggt cggttgctca caagtcctgc ctgcctgcct gtgtgtatgg acctgccgta     900
gccagtgggt acgactttga aagggaggga tactctctag tcggaataga cccttcaga     960 ctgcttcaaa acagccaagt gtacagccta atcagaccaa atgagaatcc agcacacaag    1020
agtcaactgg tgtggatggc atgccattct gccgcatttg aagatctaag agtattaagc    1080
ttcatcaaag gacgaagt gctcccaaga gggaagcttt ccactagagg agttcaaatt    1140
gcttccaatg aaaatatgga gactatgaa tcaagtacac ttgaactgag aagcaggtac    1200
tgggccataa ggaccagaag tggaggaaac accaatcaac agagggcatc tgcgggccaa    1260
atcagcatac aacctacgtt ctcagtacag agaaatctcc cttttgacag aacaaccatt    1320
atggcagcat tcaatgggaa tacagagggg agaaacatctg acatgaggac cgaaatcata    1380
aggatgatgg aaagtgcaag accagaagat gtgtctttcc aggggcgggg agtcttcgag    1440
ctctcggacg aaaaggcagc gagcccgatc gtgccttcct ttgacatgag taatgaagga    1500
tcttatttct tcggagacaa tgcagaggag tacgacaatt aaagaaaaat acccttgttt    1560
ctact                                                               1565
```

<210> SEQ ID NO 5
<211> LENGTH: 1027
<212> TYPE: DNA
<213> ORGANISM: Artificial Sequence
<220> FEATURE:
<223> OTHER INFORMATION: A synthetic oligonucleotide

<400> SEQUENCE: 5

```
agcaaaagca ggtagatatt gaaagatgag tcttctaacc gaggtcgaaa cgtacgtact      60
ctctatcatc ccgtcaggcc ccctcaaagc cgagatcgca cagagacttg aagatgtctt     120
tgcagggaag aacaccgatc ttgaggttct catggaatgg ctaaagacaa gaccaatcct     180
gtcacctctg actaagggga ttttaggatt tgtgttcacg ctcaccgtgc ccagtgagcg     240
aggactgcag cgtagacgct ttgtccaaaa tgcccttaat gggacggggg atccaaataa     300
catggacaaa gcagttaaac tgtataggaa gctcaagagg gagataacat ccatggggc      360
caaagaaatc tcactcagtt attctgctgg tgcacttgcc agttgtatgg gcctcatata     420
caacaggatg ggggctgtga ccactgaagt ggcatttggc ctggtatgtg caacctgtga     480
acagattgct gactcccagc atcggtctca taggcaaatg gtgacaacaa ccaatccact     540
aatcagacat gagaacagaa tggttttagc cagcactaca gctaaggcta tggagcaaat     600
ggctggatcg agtgagcaag cagcagaggc catggaggtt gctagtcagg ctagacaaat     660
ggtgcaagcg atgagaacca ttgggactca tcctagctcc agtgctggtc tgaaaaatga     720
tcttcttgaa aatttgcagg cctatcagaa cgaatggggg gtgcagatgc aacggttcaa     780
gtgatcctct cactattgcc gcaaatatca ttgggatctt gcacttgaca ttgtggattc     840
ttgatcgtct ttttttcaaa tgcatttacc gtcgctttaa atacggactg aaaggagggc     900
cttctacgga aggagtgcca aagtctatga gggaagaata tcgaaggaa cagcagagtg      960
ctgtggatgc tgacgatggt cattttgtca gcatagagct ggagtaaaaa actaccttgt    1020
ttctact                                                             1027
```

<210> SEQ ID NO 6
<211> LENGTH: 890
<212> TYPE: DNA
<213> ORGANISM: Artificial Sequence
<220> FEATURE:
<223> OTHER INFORMATION: A synthetic oligonucleotide

<400> SEQUENCE: 6

```
agcaaaagca gggtgacaaa aacataatgg atccaaacac tgtgtcaagc tttcaggtag      60
attgctttct ttggcatgtc cgcaaacgag ttgcagacca agaactaggc gatgccccat     120
tccttgatcg gcttcgccga gatcagaaat ccctaagagg aagggggcagt actctcggtc     180
tggacatcaa gacagccaca cgtgctggaa agcagatagt ggagcggatt ctgaaagaag     240
aatccgatga ggcacttaaa atgaccatgg cctctgtacc tgcgtcgcgt tacctaactg     300
acatgactct tgaggaaatg tcaagggact ggtccatgct catacccaag cagaaagtgg     360
caggcccctct ttgtatcaga atggaccagg cgatcatgga taagaacatc atactgaaag     420
cgaacttcag tgtgattttt gaccggctgg agactctaat attgctaagg ctttccaccg     480
aagagggagc aattgttggc gaaatttcac cattgccttc tcttccagga catactgctg     540
aggatgtcaa aaatgcagtt ggagtcctca tcggaggact tgaatggaat gataacacag     600
ttcgagtctc tgaaactcta cagagattcg cttggagaag cagtaatgag aatgggagac     660
ctccactcac tccaaaacag aaacgagaaa tggcgggaac aattaggtca gaagtttgaa     720
```

| | |
|---|---|
| gaaataagat ggttgattga agaagtgaga cacaaactga agataacaga gaatagtttt | 780 |
| gagcaaataa catttatgca agccttacat ctattgcttg aagtggagca agagataaga | 840 |
| actttctcgt ttcagcttat ttagtactaa aaaacaccct tgtttctact | 890 |

<210> SEQ ID NO 7
<211> LENGTH: 1775
<212> TYPE: DNA
<213> ORGANISM: Artificial Sequence
<220> FEATURE:
<223> OTHER INFORMATION: A synthetic oligonucleotide

<400> SEQUENCE: 7

| | |
|---|---|
| agcaaaagca ggggaaaata aaaacaacca aaatgaaggc aaacctactg gtcctgttat | 60 |
| gtgcacttgc agctgcagat gcagacacaa tatgtatagg ctaccatgcg aacaattcaa | 120 |
| ccgacactgt tgacacagta ctcgagaaga atgtgacagt gacacactct gttaacctgc | 180 |
| tcgaagacag ccacaacgga aaactatgta ttaaaagg aatagcccca ctacaattgg | 240 |
| ggaaatgtaa catcgccgga tggctcttgg gaaacccaga atgcgaccca ctgcttccag | 300 |
| tgagatcatg gtcctacatt gtagaaacac caaactctga gatggaata tgttatccag | 360 |
| gagatttcat cgactatgag gagctgaggg agcaattgag ctcagtgtca tcattcgaaa | 420 |
| gattcgaaat atttcccaaa gaaagctcat ggcccaacca acacaaaac ggagtaacgg | 480 |
| cagcatgctc ccatgagggg aaaagcagtt tttacagaaa tttgctatgg ctgacggaga | 540 |
| aggagggctc atacccaaag ctgaaaaatt cttatgtgaa caaaaaaggg aaagaagtcc | 600 |
| ttgtactgtg gggtattcat cacccgccta acagtaagga caacagaat ctctatcaga | 660 |
| atgaaaatgc ttatgtctct gtagtgactt caaattataa caggagattt accccggaaa | 720 |
| tagcagaaag acccaaagta agagatcaag ctggaggat gaactattac tggaccttgc | 780 |
| taaaacccgg agacacaata atatttgagg caaatggaaa tctaatagca ccaatgtatg | 840 |
| ctttcgcact gagtagaggc tttgggtccg gcatcatcac ctcaaacgca tcaatgcatg | 900 |
| agtgtaacac gaagtgtcaa acaccctgg gagctataaa cagcagtctc ccttaccaga | 960 |
| atatacaccc agtcacaata ggagagtgcc caaaatacgt caggagtgcc aaattgagga | 1020 |
| tggttacagg actaaggaac attccgtcca ttcaatccag aggtctattt ggagccattg | 1080 |
| ccggttttat tgaaggggga tggactggaa tgatagatgg atggtatggt tatcatcatc | 1140 |
| agaatgaaca gggatcaggc tatgcagcgg atcaaaaag cacacaaaat gccattaacg | 1200 |
| ggattacaaa caaggtgaac actgttatcg agaaaatgaa cattcaattc acagctgtgg | 1260 |
| gtaaagaatt caacaaatta gaaaaagga tggaaatttt aaataaaaa gttgatgatg | 1320 |
| gatttctgga catttggaca tataatgcag aattgttagt tctactggaa aatgaaagga | 1380 |
| ctctggattt ccatgactca aatgtgaaga tctgtatga gaaagtaaaa agccaattaa | 1440 |
| agaataatgc caaagaaatc ggaaatggat gttttgagtt ctaccacaag tgtgacaatg | 1500 |
| aatgcatgga aagtgtaaga aatgggactt atgattatcc caaatattca gaagagtcaa | 1560 |
| agttgaacag ggaaaaggta gatggagtga aattggaatc aatggggatc tatcagattc | 1620 |
| tggcgatcta ctcaactgtc gccagttcac tggtgctttt ggtctccctg ggggcaatca | 1680 |
| gtttctggat gtgttctaat ggatctttgc agtgcagaat atgcatctga gattagaatt | 1740 |
| tcagagatat gaggaaaaac acccttgttt ctact | 1775 |

<210> SEQ ID NO 8

<211> LENGTH: 1413
<212> TYPE: DNA
<213> ORGANISM: Artificial Sequence
<220> FEATURE:
<223> OTHER INFORMATION: A synthetic oligonucleotide

<400> SEQUENCE: 8

```
agcaaaagca ggggtttaaa atgaatccaa atcagaaaat aataaccatt ggatcaatct      60
gtctggtagt cggactaatt agcctaatat tgcaaatagg gaatataatc tcaatatgga     120
ttagccattc aattcaaact ggaagtcaaa accatactgg aatatgcaac caaaacatca     180
ttacctataa aaatagcacc tgggtaaagg acacaacttc agtgatatta accggcaatt     240
catctctttg tcccatccgt gggtgggcta tatacagcaa agacaatagc ataagaattg     300
gttccaaagg agacgttttt gtcataagag agcccttttat ttcatgttct cacttggaat     360
gcaggacctt ttttctgacc caaggtgcct tactgaatga caagcattca gtgggactg     420
ttaaggacag aagcccttat agggccttaa tgagctgccc tgtcggtgaa gctccgtccc     480
cgtacaattc aagatttgaa tcggttgctt ggtcagcaag tgcatgtcat gatggcatgg     540
gctggctaac aatcggaatt tcaggtccag ataatggagc agtggctgta ttaaaataca     600
acggcataat aactgaaacc ataaaaagtt ggaggaagaa aatattgagg acacaagagt     660
ctgaatgtgc ctgtgtaaat ggttcatgtt ttactataat gactgatggc ccgagtgatg     720
ggctggcctc gtacaaaatt ttcaagatcg aaaaggggaa ggttactaaa tcaatagagt     780
tgaatgcacc taattctcac tatgaggaat gttcctgtta ccctgatacc ggcaaagtga     840
tgtgtgtgtg cagagacaat tggcatggtt cgaaccggcc atgggtgtct ttcgatcaaa     900
acctggatta tcaaatagga tacatctgca gtggggtttt cggtgacaac ccgcgtcccg     960
aagatgaaac aggcagctgt ggtccagtgt atgttgatgg agcaaacgga gtaaagggat    1020
tttcatatag gtatggtaat ggtgtttgga taggaaggac caaaagtcac agttccagac    1080
atgggtttga gatgatttgg gatcctaatg atggacaga gactgatagt aagttctctg    1140
tgaggcaaga tgttgtggca atgactgatt ggtcagggta tagcggaagt ttcgttcaac    1200
atcctgagct gacagggcta gactgtatga ggccgtgctt ctgggttgaa ttaatcaggg    1260
gacgacctaa agaaaaaaca atctggacta gtgcgagcag catttctttt tgtggcgtga    1320
atagtgatac tgtagattgg tcttggccag acggtgctga gttgccattc agcattgaca    1380
agtagtctgt tcaaaaaact ccttgtttct act                                1413
```

<210> SEQ ID NO 9
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 9

```
atggaaagaa taaaagaact acga                                             24
```

<210> SEQ ID NO 10
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 10

```
agcgaaagca ggtcaattat attcaatatg gaaagaataa agaactaag aaatctaatg      60
```

```
tcgcagtctc gcacccgcga gatactcaca aaaaccaccg tggaccatat ggccataatc      120
aagaagtaca catcaggaag acaggagaag aacccagcac ttaggatgaa atggatgatg      180
gcaatgaaat atccaattac agcagacaag aggataacgg aaatgattcc tgagagaaat      240
gagcaaggac aaactttatg gagtaaaatg aatgatgccg gatcagaccg agtgatggta      300
tcacctctgg ctgtgacatg gtggaatagg aatggaccaa tgacaaatac agttcattat      360
ccaaaaatct acaaaactta ttttgaaaga gtcgaaaggc taaagcatgg aacctttggc      420
cctgtccatt ttagaaacca agtcaaaata cgtcggagag ttgacataaa tcctggtcat      480
gcagatctca gtgccaagga ggcacaggat gtaatcatgg aagttgtttt ccctaacgaa      540
gtgggagcca ggatactaac atcggaatcg caactaacga taaccaaaga gaagaaagaa      600
gaactccagg attgcaaaat ttctcctttg atggttgcat acatgttgga gagagaactg      660
gtccgcaaaa cgagattcct cccagtggct ggtggaacaa gcagtgtgta cattgaagtg      720
ttgcatttga ctcaaggaac atgctgggaa cagatgtata ctccaggagg gaagtgaag       780 aatgatgatg ttgatcaaag cttgattatt gctgctagga acatagtgag aagagctgca      840
gtatcagcag acccactagc atctttattg gagatgtgcc acagcacaca gattggtgga      900
attaggatgg tagacatcct taagcagaac ccaacagaag agcaagccgt ggatatatgc      960
aaggctgcaa tgggactgag aattagctca tccttcagtt ttggtggatt cacatttaag     1020
agaacaagcg gatcatcagt caagagagag gaagaggtgc ttacgggcaa tcttcaaaca     1080
ttgaagataa gagtgcatga gggatctgaa gagttcacaa tggttgggag aagagcaaca     1140
gccatactca gaaaagcaac caggagattg attcagctga tagtgagtgg gagagacgaa     1200
cagtcgattg ccgaagcaat aattgtggcc atggtatttt cacaagagga ttgtatgata     1260
aaagcagtta gaggtgatct gaatttcgtc aatagggcga atcagcgact gaatcctatg     1320
catcaacttt taagcatttt tcagaaggat gcgaaagtgc ttttttcaaaa ttggggagtt     1380 gaacctatcg acaatgtgat gggaatgatt gggatattgc cgacatgac tccaagcatc      1440 gagatgtcaa tgagaggagt gagaatcagc aaaatgggtg tagatgagta ctccagcacg     1500
gagagggtag tggtgagcat tgaccggttc ttgagagtca gggaccaacg aggaaatgta     1560
ctactgtctc ccgaggaggt cagtgaaaca caggaacag agaaactgac aataacttac      1620
tcatcgtcaa tgatgtggga gattaatggt cctgaatcag tgttggtcaa tacctatcaa     1680
tggatcatca gaaactggga aactgttaaa attcagtggt cccagaaccc tacaatgcta     1740
tacaataaaa tggaatttga accatttcag tctttagtac ctaaggccat tagaggccaa     1800
tacagtgggt ttgtaagaac tctgttccaa caaatgaggg atgtgcttgg acatttgat      1860 accgcacaga taataaaact tcttcccttc gcagccgctc caccaaagca agtagaatg      1920 cagttctcct catttactgt gaatgtgagg ggatcaggaa tgagaatact tgtaaggggc     1980
aattctcctg tattcaacta caacaaggcc acgaagagac tcacagttct cggaaaggat     2040
gctggcactt taaccgaaga cccagatgaa ggcacagctg gagtggagtc cgctgttctg     2100 agggattcc tcattctggg caagaagac aggagatatg gccagcatt aagcatcaat       2160 gaactgagca accttgcgaa aggagagaag gctaatgtgc taattgggca aggagacgtg     2220
gtgttggtaa tgaaacgaaa acgggactct agcatactta ctgacagcca gacagcgacc     2280
aaaagaattc ggatggccat caattagtgt cgaatagttt aaaaacgacc ttgtttctac     2340
t                                                                     2341
```

<210> SEQ ID NO 11
<211> LENGTH: 2341
<212> TYPE: DNA
<213> ORGANISM: Artificial Sequence
<220> FEATURE:
<223> OTHER INFORMATION: A synthetic oligonucleotide

<400> SEQUENCE: 11

| | | | | | |
|---|---|---|---|---|---|
| agcgaaagca | ggcaaaccat | ttgaatggat | gtcaatccga | ccttactttt | cttaaaagtg | 60 |
| ccagcacaaa | atgctataag | cacaactttc | ccttataccg | gagaccctcc | ttacagccat | 120 |
| gggacaggaa | caggatacac | catggatact | gtcaacagga | cacatcagta | ctcagaaaag | 180 |
| ggaagatgga | caacaaacac | cgaaactgga | gcaccgcaac | tcaacccgat | tgatgggcca | 240 |
| ctgccagaag | acaatgaacc | aagtggttat | gcccaaacag | attgtgtatt | ggaagcaatg | 300 |
| gctttccttg | aggaatccca | tcctggtatt | tttgaaaact | cgtgtattga | aacgatggag | 360 |
| gttgttcagc | aaacacgagt | agacaagctg | acacaaggcc | gacagaccta | tgactggact | 420 |
| ttaaatagaa | accagcctgc | tgcaacagca | ttggccaaca | caatagaagt | gttcagatca | 480 |
| aatggcctca | cggccaatga | gtcaggaagg | ctcatagact | tccttaagga | tgtaatggag | 540 |
| tcaatgaaaa | aagaagaaat | ggggatcaca | actcattttc | agagaaagag | acgggtgaga | 600 |
| gacaatatga | ctaagaaaat | gataacacag | agaacaatag | gtaaaggaa | acagagattg | 660 |
| aacaaagggg | gttatctaat | tagagcattg | accctgaaca | caatgaccaa | agatgctgag | 720 |
| agagggaagc | taaaacggag | agcaattgca | accccaggga | tgcaaataag | ggggtttgta | 780 |
| tactttgttg | agacactggc | aaggagtata | tgtgagaaac | ttgaacaatc | agggttgcca | 840 |
| gttggaggca | atgagaagaa | agcaaagttg | gcaaatgttg | taaggaagat | gatgaccaat | 900 |
| tctcaggaca | ccgaactttc | tttcaccatc | actggagata | acaccaaatg | gaacgaaaat | 960 |
| cagaatcctc | ggatgttttt | ggccatgatc | acatatatga | ccagaaatca | gcccgaatgg | 1020 |
| ttcagaaatg | ttctaagtat | tgctccaata | atgttctcaa | acaaaatggc | gagactggga | 1080 |
| aagggtata | tgtttgagag | caagagtatg | aaacttagaa | ctcaaatacc | tgcagaaatg | 1140 |
| ctagcaagca | ttgatttgaa | atatttcaat | gattcaacaa | gaagaagat | tgaaaaaatc | 1200 |
| cgaccgctct | aatagaggg | gactgcatca | ttgagccctg | gaatgatgat | gggcatgttc | 1260 |
| aatatgttaa | gcactgtatt | aggcgtctcc | atcctgaatc | ttggacaaaa | gagatacacc | 1320 |
| aagactactt | actggtggga | tggtcttcaa | tcctctgacg | attttgctct | gattgtgaat | 1380 |
| gcacccaatc | atgaagggat | tcaagccgga | gtcgacaggt | tttatcgaac | ctgtaagcta | 1440 |
| cttggaatca | atatgagcaa | gaaaaagtct | tacataaaca | gaacaggtac | atttgaattc | 1500 |
| acaagttttt | tctatcgtta | tgggtttgtt | gccaatttca | gcatggagct | tcccagtttt | 1560 |
| ggggtgtctg | ggatcaacga | gtcagcggac | atgagtattg | gagttactgt | catcaaaaac | 1620 |
| aatatgataa | acaatgatct | tggtccagca | acagctcaaa | tggcccttca | gttgttcatc | 1680 |
| aaagattaca | ggtacacgta | ccgatgccat | agaggtgaca | cacaaataca | aacccgaaga | 1740 |
| tcatttgaaa | taaagaaact | gtgggagcaa | acccgttcca | aagctggact | gctggtctcc | 1800 |
| gacgaggcc | caaatttata | caacattaga | aatctccaca | ttcctgaagt | ctgcctaaaa | 1860 |
| tgggaattga | tggatgagga | ttaccagggg | cgtttatgca | acccactgaa | cccatttgtc | 1920 |
| agccataaag | aaattgaatc | aatgaacaat | gcagtgatga | tgccagcaca | tggtccagcc | 1980 |
| aaaaacatgg | agtatgatgc | tgttgcaaca | acacactcct | ggatcccaa | agaaatcga | 2040 |
| tccatcttga | atacaagtca | aagaggagta | cttgaagatg | aacaaatgta | ccaaaggtgc | 2100 |

| | |
|---|---:|
| tgcaatttat tgaaaaatt cttccccagc agttcataca aagaccagt cgggatatcc | 2160 |
| agtatggtgg aggctatggt ttccagagcc cgaattgatg cacggattga tttcgaatct | 2220 |
| ggaaggataa agaaagaaga gttcactgag atcatgaaga tctgttccac cattgaagag | 2280 |
| ctcagacggc aaaaatagtg aatttagctt gtccttcatg aaaaaatgcc ttgtttctac | 2340 |
| t | 2341 |

<210> SEQ ID NO 12
<211> LENGTH: 2233
<212> TYPE: DNA
<213> ORGANISM: Artificial Sequence
<220> FEATURE:
<223> OTHER INFORMATION: A synthetic oligonucleotide

<400> SEQUENCE: 12

| | |
|---|---:|
| agcgaaagca ggtactgatt caaaatggaa gattttgtgc gacaatgctt caatccgatg | 60 |
| attgtcgagc ttgcggaaaa acaatgaaa gagtatgggg aggacctgaa atcgaaaca | 120 |
| aacaaatttg cagcaatatg cactcacttg gaagtatgct tcatgtattc agatttccac | 180 |
| ttcatcaatg agcaaggcga gtcaataatc gtagaacttg gtgatcctaa tgcacttttg | 240 |
| aagcacagat ttgaaataat cgagggaaga gatcgcacaa tggcctggac agtagtaaac | 300 |
| agtatttgca acactacagg ggctgagaaa ccaaagtttc taccagattt gtatgattac | 360 |
| aaggaaaata gattcatcga aattggagta acaaggagag aagttcacat atactatctg | 420 |
| gaaaaggcca ataaaattaa atctgagaaa acacacatcc acattttctc gttcactggg | 480 |
| gaagaaatgg ccacaagggc cgactacact ctcgatgaag aaagcagggc taggatcaaa | 540 |
| accaggctat tcaccataag acaagaaatg gccagcagag gcctctggga ttcctttcgt | 600 |
| cagtccgaga gaggagaaga gacaattgaa gaaaggtttg aaatcacagg aacaatgcgc | 660 |
| aagcttgccg accaaagtct cccgccgaac ttctccagcc ttgaaaattt tagagcctat | 720 |
| gtggatggat tcgaaccgaa cggctacatt gagggcaagc tgtctcaaat gtccaaagaa | 780 |
| gtaaatgcta gaattgaacc ttttttgaaa acaacaccac gaccacttag acttccgaat | 840 |
| gggcctcoct gttctcagcg gtccaaattc ctgctgatgg atgccttaaa attaagcatt | 900 |
| gaggacccaa gtcatgaagg agagggaata ccgctatatg atgcaatcaa atgcatgaga | 960 |
| acattctttg gatggaagga acccaatgtt gttaaaccac acgaaagggg aataaatcca | 1020 |
| aattatcttc tgtcatggaa gcaagtactg gcagaactgc aggacattga gaatgaggag | 1080 |
| aaaattccaa agactaaaaa tatgaaaaaa acaagtcagc taaagtgggc acttggtgag | 1140 |
| aacatggcac cagaaaaggt agactttgac gactgtaaag atgtaggtga tttgaagcaa | 1200 |
| tatgatagtg atgaaccaga attgaggtcg cttgcaagtt ggattcagaa tgagttcaac | 1260 |
| aaggcatgcg aactgacaga ttcaagctgg atagagcttg atgagattgg agaagatgtg | 1320 |
| gctccaattg aacacattgc aagcatgaga aggaattatt tcacatcaga ggtgtctcac | 1380 |
| tgcagagcca cagaatacat aatgaagggg gtgtacatca atactgcctt acttaatgca | 1440 |
| tcttgtgcag caatggatga tttccaatta attccaatga taagcaagtg tagaactaag | 1500 |
| gagggaaggc gaaagaccaa cttgtatggt ttcatcataa aaggaagatc ccacttaagg | 1560 |
| aatgacaccg acgtggtaaa ctttgtgagc atggagtttt ctctcactga cccaagactt | 1620 |
| gaaccacaca aatgggagaa gtactgtgtt cttgagatag gagatatgct tctaagaagt | 1680 |
| gccataggcc aggtttcaag gcccatgttc ttgtatgtga ggacaaatgg aacctcaaaa | 1740 |

| | |
|---|---:|
| attaaaatga aatggggaat ggagatgagg cgttgtctcc tccagtcact tcaacaaatt | 1800 |
| gagagtatga ttgaagctga gtcctctgtc aaagagaaag acatgaccaa agagttcttt | 1860 |
| gagaacaaat cagaaacatg gcccattgga gagtctccca aaggagtgga ggaaagttcc | 1920 |
| attgggaagg tctgcaggac tttattagca aagtcggtat ttaacagctt gtatgcatct | 1980 |
| ccacaactag aaggattttc agctgaatca agaaaactgc ttcttatcgt tcaggctctt | 2040 |
| agggacaatc tggaacctgg gacctttgat cttgggggc tatatgaagc aattgaggag | 2100 |
| tgcctaatta atgatccctg gttttgctt aatgcttctt ggttcaactc cttccttaca | 2160 |
| catgcattga gttagttgtg gcagtgctac tatttgctat ccatactgtc caaaaagta | 2220 |
| ccttgtttct act | 2233 |

<210> SEQ ID NO 13
<211> LENGTH: 1565
<212> TYPE: DNA
<213> ORGANISM: Artificial Sequence
<220> FEATURE:
<223> OTHER INFORMATION: A synthetic oligonucleotide

<400> SEQUENCE: 13

| | |
|---|---:|
| agcaaaagca gggtagataa tcactcactg agtgacatca aaatcatggc gtcccaaggc | 60 |
| accaaacggt cttacgaaca gatggagact gatggagaac gccagaatgc cactgaaatc | 120 |
| agagcatccg tcgaaaaaat gattggtgga attggacgat tctacatcca aatgtgcaca | 180 |
| gaacttaaac tcagtgatta tgagggacgg ttgatccaaa acagcttaac aatagagaga | 240 |
| atggtgctct ctgcttttga cgaaaggaga aataaatacc tggaagaaca tcccagtgcg | 300 |
| gggaaagatc ctaagaaaac tggaggacct atatacagaa gagtaaacgg aaagtggatg | 360 |
| agagaactca tcctttatga caaagaagaa ataaggcgaa tctggcgcca agctaataat | 420 |
| ggtgacgatg caacggctgg tctgactcac atgatgatct ggcattccaa tttgaatgat | 480 |
| gcaacttatc agaggacaag ggctcttgtt cgcaccggaa tggatcccag gatgtgctct | 540 |
| ctgatgcaag gttcaactct ccctaggagg tctggagccg caggtgctgc agtcaaagga | 600 |
| gttggaacaa tggtgatgga attggtcagg atgatcaaac gtgggatcaa tgatcggaac | 660 |
| ttctggaggg gtgagaatgg acgaaaaaca agaattgctt atgaaagaat gtgcaacatt | 720 |
| ctcaaaggga aatttcaaac tgctgcacaa aaagcaatga tggatcaagt gagagagagc | 780 |
| cggaacccag ggaatgctga gttcgaagat ctcacttttc tagcacggtc tgcactcata | 840 |
| ttgagagggt cggttgctca caagtcctgc ctgcctgcct gtgtgtatgg acctgccgta | 900 |
| gccagtgggt acgactttga agagaggga tactctctag tcggaataga ccctttcaga | 960 |
| ctgcttcaaa acagccaagt gtacagccta atcagaccaa atgagaatcc agcacacaag | 1020 |
| agtcaactgg tgtggatggc atgccattct gccgcatttg aagatctaag agtattgagc | 1080 |
| ttcatcaaag gacgaaggt ggtcccaaga gggaagcttt ccactagagg agttcaaatt | 1140 |
| gcttccaatg aaaatatgga gactatggaa tcaagtacac ttgaactgag aagcaggtac | 1200 |
| tgggccataa ggaccagaag tggaggaaac accaatcaac agagggcatc tgcgggccaa | 1260 |
| atcagcatac aacctacgtt ctcagtacag agaaatctcc cttttgacag aacaaccgtt | 1320 |
| atggcagcat tcactgggaa tacagagggg agaacatctg acatgaggac cgaaatcata | 1380 |
| aggatgatgg aaagtgcaag accagaagat gtgtctttcc aggggcgggg agtcttcgag | 1440 |
| ctctcggacg aaaaggcagc gagcccgatc gtgccttcct ttgacatgag taatgaagga | 1500 |
| tcttatttct tcggagacaa tgcagaggag tacgacaatt aaagaaaaat accttgtttt | 1560 |

```
ctact                                                                  1565

<210> SEQ ID NO 14
<211> LENGTH: 1027
<212> TYPE: DNA
<213> ORGANISM: Artificial Sequence
<220> FEATURE:
<223> OTHER INFORMATION: A synthetic oligonucleotide

<400> SEQUENCE: 14
agcaaaagca ggtagatatt gaaagatgag tcttctaacc gaggtcgaaa cgtacgttct     60
ctctatcatc ccgtcaggcc ccctcaaagc cgagatcgca cagagacttg aagatgtctt    120
tgcagggaag aacaccgatc ttgaggttct catggaatgg ctaaagacaa gaccaatcct    180
gtcacctctg actaagggga ttttaggatt tgtgttcacg ctcaccgtgc ccagtgagcg    240
aggactgcag cgtagacgct ttgtccaaaa tgcccttaat gggaacgggg atccaaataa    300
catggacaaa gcagttaaac tgtataggaa gctcaagagg gagataacat tccatggggc    360
caaagaaatc tcactcagtt attctgctgg tgcacttgcc agttgtatgg gcctcatata    420
caacaggatg ggggctgtga ccactgaagt ggcatttggc ctggtatgtg caacctgtga    480
acagattgct gactcccagc atcggtctca taggcaaatg gtgacaacaa ccaacccact    540
aatcagacat gagaacagaa tggttttagc cagcactaca gctaaggcta tggagcaaat    600
ggctggatcg agtgagcaag cagcagaggc catggaggtt gctagtcagg ctaggcaaat    660
ggtgcaagcg atgagaacca ttgggactca tcctagctcc agtgctggtc tgaaaaatga    720
tcttcttgaa aatttgcagg cctatcagaa acgaatgggg gtgcagatgc aacggttcaa    780
gtgatcctct cgctattgcc gcaaatatca ttgggatctt gcacttgata ttgtggattc    840
ttgatcgtct tttttttcaaa tgcatttacc gtcgctttaa atacggactg aaaggagggc    900
cttctacgga aggagtgcca aagtctatga gggaagaata tcgaaaggaa cagcagagtg    960
ctgtggatgc tgacgatggt cattttgtca gcatagagct ggagtaaaaa actaccttgt   1020
ttctact                                                             1027

<210> SEQ ID NO 15
<211> LENGTH: 890
<212> TYPE: DNA
<213> ORGANISM: Artificial Sequence
<220> FEATURE:
<223> OTHER INFORMATION: A synthetic oligonucleotide

<400> SEQUENCE: 15
agcaaaagca gggtgacaaa gacataatgg atccaaacac tgtgtcaagc tttcaggtag     60
attgctttct ttggcatgtc cgcaaacgag ttgcagacca agaactaggt gatgccccat    120
tccttgatcg gcttcgccga gatcagaaat ccctaagagg aaggggcagc actcttggtc    180
tggacatcga gacagccaca cgtgctggaa agcagatagt ggagcggatt ctgaaagaag    240
aatccgatga ggcacttaaa atgaccatgg cctctgtacc tgcgtcgcgt tacctaaccg    300
acatgactct tgaggaaatg tcaagggaat ggtccatgct catacccaag cagaaagtgg    360
caggccctct ttgtatcaga atggaccagg cgatcatgga taaaaacatc atactgaaag    420
cgaacttcag tgtgattttt gaccggctgg agactctaat attgctaagg ctttcaccg     480
aagagggagc aattgttggc gaaatttcac cattgcctt ttcttccagga catactgctg    540
aggatgtcaa aaatgcagtt ggagtcctca tcggaggact tgaatggaat gataacacag    600
```

-continued

```
ttcgagtctc tgaaactcta cagagattcg cttggagaag cagtaatgag aatgggagac      660
ctccactcac tccaaaacag aaacgagaaa tggcgggaac aattaggtca gaagtttgaa      720
gaaataagat ggttgattga agaagtgaga cacaaactga aggtaacaga gaatagtttt      780
gagcaaataa catttatgca agccttacat ctattgcttg aagtggagca agagataaga      840
actttctcat ttcagcttat ttaataataa aaaacaccct tgtttctact                 890

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16
gccacaatta ttgcttcggc                                                   20
```

INFLUENZA VIRUSES WITH MUTANT PB2 GENE SEGMENT AS LIVE ATTENUATED VACCINES

CROSS-REFERENCE TO RELATED APPLICATIONS

This application claims the benefit of the filing date of U.S. application Ser. No. 61/527,935, filed on Aug. 26, 2011, the disclosure of which is incorporated by reference herein.

STATEMENT OF GOVERNMENT RIGHTS

This invention was made with government support under AI047446 awarded by the National Institutes of Health. The government has certain rights in the invention.

BACKGROUND

Influenza viruses instigate annual global epidemics and sporadic pandemics. Influenza A viruses annually cause epidemics characterized by a contagious respiratory illness, mild to severe fever, and in some instances death (Palese & Shaw, 2007). Vaccine and curative antiviral research that focuses on the prevention and control of this potentially fatal virus is warranted to avoid considerable strains on health care systems and the global economy. Intensive research has led to the discovery of therapeutic interventions to combat influenza infections; however, due to the virus's error-prone polymerase, the hemagglutinin (HA) and neuraminidase (NA) influenza viral proteins are subject to point mutations, known as antigenic or genetic drift (Lin et al., 2004), that allow the virus to escape host immune responses or result in some types of drug resistance (Moss et al., 2010). Vaccination is one of the most effective means of preventing influenza-associated morbidity and mortality.

Currently available therapeutic and prophylactic interventions include two types of vaccines (i.e., inactivated and live vaccines) and two classes of antivirals (i.e., M2 ion channel blockers, such as amantadine and rimantadine, and neuraminidase (NA)-inhibitors, such as oseltamivir and zanamivir) (Davies et al., 1964; Hayden, 2001). Nonetheless, seasonal influenza is a contagious disease with one of the highest impacts on public health epidemiology. Further, during the 2009-2010 influenza season, a novel influenza A virus strain, the 2009 H1N1 pandemic virus, emerged and spread worldwide, causing the first influenza pandemic in 40 years with a considerable impact on global health and economics (http://www.cdc.gov/flu/about/disease/index.htm). In the United States alone, an estimated 61 million H1N1 cases, including 274,000 hospitalizations and 12,470 deaths were reported (http://www.cde.gov/flu/about/season/index.htm).

Due to an underdeveloped or impaired immune system, young, elderly or immuno-compromised individuals are especially susceptible to infectious diseases such as influenza. Several studies conducted in Japan suggested that high rates of influenza vaccination among school age children provided protection, reduced community-wide effects, and reduced incidence and mortality of older persons from influenza infection; the 2001 study reported the prevention of approximately 37,000 to 49,000 deaths per year and the rise of excess mortality rates when vaccination of schoolchildren was discontinued (Reichert et al., 2001).

Currently available inactivated influenza vaccines are associated with short protection periods and limited efficacy, especially in young children and the elderly. Due to the inability to effectively elicit cell-mediated immunity, inactivated vaccines are generally less immunogenic, and hence less potent, than live attenuated vaccines, which are approved for use in a limited number of countries such as the Unites States. Intranasally administered live attenuated viruses are considered superior to inactivated vaccines for children because they elicit robust mucosal immunity and humoral and cellular immune responses coupled with long-lasting protective efficacy (Cox et al., 2004). However, live attenuated vaccines are currently licensed only for individuals aged 2 through 49 who lack chronic medical conditions and who are not pregnant or immunocompromised, even though licensed live attenuated influenza viruses are considered safe and stable with respect to the underlying risk of the emergence of revertant viruses.

Parenterally administered inactivated vaccines are also associated with adverse or anaphylactic reactions due to virus propagation in embryonated eggs, and the propensity of egg proteins in these vaccines to induce allergies by inducing hypersensitivity reactions in susceptible hosts. A prerequisite for successful egg-based vaccine propagation is the selection of variants adapted to embryonated chicken eggs; a criterion that may no longer match the antigenicity of circulating viruses. A further complication includes the possible depletion of chicken stocks in light of a looming zoonotic outbreak of avian influenza pandemic, which could compromise mass vaccine production.

Live attenuated influenza vaccine (LAIV) was originally derived by cold adaptation of an influenza type A strain (A/Ann Arbor/6/60 H2N2) and a type B strain (B/Ann Arbor/1/66) by serial passage at sequentially lower temperatures in specific pathogen-free primary chick kidney cells (Maassab et al., 1968). During this process, the viruses acquired multiple mutations in internal protein gene segments (i.e., genes encoding "internal" nonglycosylated proteins) that produced the cold-adapted (ca), temperature sensitive (ts), and attenuated (att) phenotype of the master donor viruses (MDVs). The MDVs represent the LAIV genetic backbone that is updated annually with hemagglutinin (HA) and neuraminidase (NA) genes from contemporary influenza viruses to produce the annual trivalent formulation. Thus, each of the three influenza virus strains is a 6:2 genetic reassortant virus, containing six internal gene segments from ca, ts, and att MDVs and two gene segments (encoding the HA and NA proteins) from a wild-type influenza virus that is selected annually by the World Health Organization and the U.S. Public Health Service.

Because multiple loci in several genes control the ca, ts, and att phenotypes of LAIV vaccine viruses, it is highly improbable that LAIV would lose these phenotypes as a result of reversion (Kemble et al., 2003; Murphy et al., 2002). Given the error rate of $10^{-4}$ to $10^{-5}$ misincorporations per nucleotide position during influenza virus replication and the fact that at least five point mutations are responsible for the attenuated properties of each MDV (Murphy et al., 2002; Smith et al., 1987), the probability of a LAIV vaccine virus reverting to wild-type influenza, with mutations in the five attenuating loci, would be one in at least $10^{20}$ replication cycles. In one study of 135 vaccine strains recovered from young vaccinated children, no evidence of reversion was observed (Vesikari et al., 2006).

The first nasally administered LIAV was approved for use in the United States in 2003, marketed in the United States as FluMist® [Influenza Virus Vaccine Live, Intranasal]). Although LAIV vaccine viruses were originally generated using classical reassortment, in 2008 the process transitioned to reverse genetics technology. The genetic reassortant viruses therein are prepared using reverse genetics technology in cell culture, a technique whereby influenza viruses can be generated from DNA plasmids containing influenza genes. Three vaccine strains are formulated together to produce a trivalent LAIV vaccine in single-dose sprayers. The intranasal LAIV is currently approved in the United States for use in individuals 2-49 years of age.

Live attenuated viruses are considered superior to inactivated vaccines due to their ability to elicit both humoral and cellular immune responses and hence confer advanced protection in infants and young children. In particular, intranasally administered live attenuated vaccines elicit robust mucosal immunity and cellular responses coupled with longer lasting protective efficacies (Cox et al., 2004). Live attenuated influenza vaccine viruses replicate primarily in the ciliated epithelial cells of the nasopharyngeal mucosa to induce immune responses (via mucosal immunoglobulin IgA, serum IgG antibodies, and cellular immunity), but LAIV viruses do not replicate well at the warmer temperatures found in the lower airways and lung (Murphy et al., 2002; Gruber et al., 2002). In addition, there are several advantages of a cell-based (e.g., cells employed to amplify virus after virus generation using reverse genetics) alternative over the conventional egg-based vaccine propagation system. Cell-based vaccine studies have demonstrated significant advantages over egg-based vaccinology in that they are a more economically feasible, rapid, and less labor-intensive alternative whose manufacturing capacity can be readily scaled-up in proportion to demand in the context of a pandemic. Moreover, genetic engineering of viruses through recombinant DNA-based technologies allows the exploitation of a virus' genetic parasitism, while disarming its pathogenic power. Viruses can be rendered replication-incompetent and non-pathogenic or manipulated to introduce and express a foreign gene in a receptive host.

SUMMARY OF THE INVENTION

The invention provides a recombinant biologically contained influenza virus that is useful to generate a multivalent vaccine, and satisfies safety concerns regarding pathogenicity or reversion, which virus optionally may stably express a foreign gene and so can be effectively traced and have its replication easily assessed. As disclosed hereinbelow, a PB2-knock-out (PB2-KO) influenza virus was generated that harbors a reporter gene, e.g., a fluorescent protein gene such as a GFP gene or a luciferase gene, in the coding region of its PB2 viral RNA (vRNA), where the replication of the virus was restricted to a cell line that stably expressed the PB2 protein. The reporter gene-encoding PB2 vRNA was stably incorporated into progeny viruses during replication in PB2-expressing cells, and the reporter gene was expressed in virus infected cells with no evidence of recombination between the recombinant PB2 vRNA and the PB2 protein mRNA. Further, the HA and NA genes of different virus strains were readily accommodated by the PB2-KO virus. The PB2-KO virus was used to establish an improved assay to screen neutralizing antibodies against influenza viruses by using reporter gene expression as an indicator of virus infection rather than observing cytopathic effect. These results indicate that the PB2-KO virus have the potential to be a valuable tool for basic and applied influenza virology research, and that may be applicable to other polymerase gene knock-out viruses, e.g., PA-KO viruses or PB1-KO viruses.

In one embodiment, the invention provides isolated infectious, biologically contained influenza virus that has a viral gene segment that does not comprise contiguous nucleic acid sequences corresponding to those encoding PB2 (a mutant PB2 viral gene segment), a protein which is one of the viral RNA polymerase subunits and is essential for virus replication. To prepare such a virus in cell culture, a cell line is employed that expresses PB2 in trans in combination with vectors for influenza virus vRNA production, but not one for a wild-type PB2 viral gene segment, and in one embodiment vectors for influenza virus mRNA protein production. The resulting virus is not competent to express PB2 after infection of cells that do not express PB2 in trans or are not infected with helper virus, which provides for a "biologically contained" virus. However, virions produced from cells that express PB2 in trans contain PB2. Such an infectious, biologically contained influenza virus with a mutant PB2 viral gene segment was generated in multiple cell lines that express PB2 in trans, such as PB2-expressing 293 human embryonic kidney (293), human lung adenocarcinoma epithelial (A549), or 2,6-linked sialyltransferase-overexpressing Madin-Darby canine kidney (MDCK) cells (AX4 cells), resulting in high virus titers of at least $10^4$, $10^5$, $10^6$, $10^7$ or $10^8$ PFU/mL, or more.

Vaccination is the primary means for prophylaxis against influenza infection. As disclosed herein, the PB2-KO virus replicated to high titers (>$10^8$ PFU/mL) in PB2-expressing but not in normal uninfected cells (cells that do not express PB2 in trans), accommodated HA and NA genes of a heterologous influenza virus), stably incorporated a reporter gene into progeny PB2-KO virions that was retained through sequential passages, and was attenuated in mice, suggesting its potential as a vaccine. Its ability to express antigens and its vaccine candidacy was tested in a murine model. Significantly higher levels of IgG and IgA antibodies were induced in sera, nasal washes and broncho-alveolar lavage samples from mice immunized with only one dose of PB2-KO (GFP) virus compared to inactivated influenza vaccine. All PB2-KO virus-treated mice survived challenge with various lethal doses of PR8. Limited replication of that virus occurs in vivo as the virus produced in cells that express PB2 in trans carries along a small amount of PB2 protein into the host cell which is subsequently infected (such as a host cell which does not itself express or comprise PB2 or comprise wild-type PB2 vRNA), thereby allowing for a limited amount (e.g., a round or so) of replication to occur but without a significant infectious process (for instance, amplification of virus titers of over about 1000). The limited replication of the KO virus in vivo allows for an immune response that provides for a more robust immune response than induced by conventional inactivated influenza vaccines. It is noteworthy that the immunized mice produce antibodies against the reporter, as determined by an immunofluorescence assay, suggesting that PB2-KO virus has the potency of a multivalent vaccine. The PB2-KO exhibited similar or better safety and efficacy profiles when compared to controls, and so holds promise for combating influenza virus infection.

In one embodiment, the invention provides an isolated infectious, biologically contained recombinant influenza virus comprising 8 gene segments including a PA viral gene segment, a PB1 viral gene segment, a mutant PB2 viral gene segment, a HA viral gene segment, a NA viral gene segment, a NP viral gene segment, a M (M1 and M2) viral gene segment, and a NS (NS1 and NS2) viral gene segment. In another embodiment, the invention provides an isolated infectious, biologically contained recombinant influenza virus comprising 8 gene segments including a PA viral gene segment, a PB1 viral gene segment, a mutant PB2 viral gene segment, a HA viral gene segment, a NA (NA and NB) viral gene segment, a NP viral gene segment, a M (M1 and BM2) viral gene segment, and a NS (NS1 and NS2) viral gene segment. In one embodiment, the infectious, biologically contained recombinant influenza virus has a M viral gene segment for M1 and M2. In one embodiment, the infectious, biologically contained recombinant influenza virus has a NA viral gene segment for NB and NA. In one embodiment, the infectious, biologically contained recombinant influenza virus has a HEF gene segment.

In yet another embodiment, the invention provides an isolated infectious, biologically contained recombinant influenza virus comprising gene segments including a PA viral gene segment, a PB1 viral gene segment, a mutant PB2 viral gene segment, a NP viral gene segment, a M viral gene segment, a NS viral gene segment (for NS1 and NS2), and a HEF viral gene segment. In one embodiment, the mutant PB2 viral gene segment includes 5' and/or 3' PB2 viral non-coding and coding incorporation sequences, optionally flanking a heterologous nucleotide sequence, and does not include contiguous sequences corresponding to sequences encoding a functional PB2. The PB2 open reading frame in the mutant PB2 viral gene segment may be replaced with or disrupted by a heterologous nucleotide sequence, such as one that is readily detectable after transfection or infection, e.g., a reporter gene such as a GFP gene or a luciferase gene, e.g., a *Renilla* luciferase gene, or a gene encoding an antigen from a pathogen. In one embodiment, the PB2 coding region in the mutant PB2 viral gene segment may include mutations such as insertions or deletions of one or more nucleotides or those that result in one or more amino acid substitutions or a stop codon, or any combination thereof, that yields a non-functional PB2 coding sequence. In one embodiment, the heterologous nucleotide sequence is about 30 to about 5,000, e.g., about 100 to about 4,500 or about 500 to about 4,000, nucleotides in length.

The infectious, biologically contained viruses of the invention may thus be used as influenza vaccines to induce an immunogenic response in a host, without the risk of symptoms associated with an infection or genetic reversion from an attenuated to a fully infectious form. The infectious, biologically contained viruses of the invention may elicit a better immune response than chemically inactivated viruses because they are live viruses, yet because they are biologically contained, the viruses of the invention likely do not cause symptoms of the disease, which is often an issue with live attenuated vaccines. And in contrast to the use of virus-like particles (VLPs), which are non-replicative, the KO viruses of the invention contain RNA, which is an adjuvant that enhances the host's immune response against the virus. The properties of a PB2-KO influenza virus of the invention were surprising given that a similar virus, a M2 deficient virus that lacks the transmembrane and cytoplasmic domains of M2 (see, Watanabe et al., *J. Virol.*, 83:5944 (2009)) grew to low titers, e.g., $10^2$-$10^3$ PFU/mL, in the absence of M2 supplied in trans, and so was replication-defective but not biologically contained.

In one embodiment, the invention provides an isolated recombinant infectious, biologically contained influenza virus comprising 7 gene segments including a PA viral gene segment, a PB1 viral gene segment, a HA viral gene segment, a NA viral gene segment, a NP viral gene segment, a M viral gene segment, and a NS1 and NS2 viral gene segment, i.e., the virus lacks a PB2 viral gene segment.

In one embodiment, for the 8 segment PB2-KO influenza virus having a mutant PB2 viral gene segment, the mutant PB2 viral gene segment has a deletion of PB2 coding sequences, a deletion of PB2 coding sequences and an insertion of heterologous nucleotide sequences, or an insertion of heterologous nucleotide sequences which disrupts PB2 coding sequences. That virus replicates in vitro when PB2 is supplied in trans to titers that are substantially the same or at most 10, 100 or 1,000 fold less than a corresponding wild-type influenza virus, but is attenuated in vivo or in vitro in the absence of PB2 supplied in trans. In one embodiment, the deletion of PB2 coding sequences includes 1 or more contiguous or noncontiguous nucleotides of PB2 and may include a deletion of the entire coding region, e.g., a region encoding 759 amino acids. In one embodiment, the deletion includes at least 10%, 30%, 40%, 50%, 70%, 80%, 85%, 90%, 93%, 95% and up to 99%, or a percent numerical value that is any integer between 10 and 99, but not all, of the PB2 coding region. In one embodiment, the deletion of PB2 coding sequences does not include the deletion of 5' or 3' coding sequences that enhance incorporation of the resulting viral gene segment into virions, e.g., sequences that are contiguous to 3' or 5' non-coding PB2 sequences, relative to a recombinant viral gene segment with only non-coding PB2 incorporation sequences.

In one embodiment, the mutant PB2 gene segment may comprise an insertion of one or more nucleotides, e.g., those that result in a frame-shift, so that functional PB2 cannot be expressed. In one embodiment, the insertion does not include the alteration of 5' or 3' coding sequences that enhance incorporation of the gene segment into virions relative to a recombinant gene segment with only non-coding PB2 incorporation sequences.

In one embodiment, the mutant PB2 viral gene segment may comprise at least one mutation that results in at least one amino acid substitution relative to a corresponding wild-type PB2 protein, e.g., a mutation that removes or replaces the initiator codon, or that introduces one or more stop codons into the coding region, so that functional PB2 cannot be expressed from that viral gene segment after infection. In one embodiment, the substitution, removal or replacement of the initiator codon, or introduction of the one or more stop codons in the reading frame for PB2, does not include the alteration of 5' or 3' coding sequences that enhance incorporation of the gene segment into virions relative to a recombinant gene segment with only non-coding PB2 incorporation sequences.

In one embodiment of the invention, the heterologous nucleotide sequence may encode a heterologous protein (a non-influenza viral protein such as a glycoprotein or a cytosolic, nuclear or mitochondrial specific protein, or any antigenic protein such as an antigen from a microbial pathogen), which may confer a detectable phenotype. In one embodiment, the heterologous nucleotide sequence may be fused to truncated portions of PB2 coding sequences, e.g., those corresponding to 5' or 3' PB2 coding incorporation sequences, optionally forming a chimeric protein. In one embodiment, the heterologous nucleotide sequence replaces or is introduced to sequences in the viral gene segment corresponding to the coding region for that segment, so as not to disrupt the incorporation sequences in the coding region of the gene segment. For instance, the heterologous nucleotide sequence may be flanked by about 3 to about 400 nucleotides of the 5' and/or 3' PB2 coding region adjacent to non-coding sequence. In one embodiment, the 3' PB2 incorporation sequences correspond to nucleotides 3 to 400, nucleotides 3 to 300, nucleotides 3 to 100, nucleotides 3 to 50, or any integer between 3 and 400, of the N-terminal and/or C-terminal PB2 coding region. In one embodiment, after infection of a host cell with the biologically contained PB2-KO virus, a heterologous protein is produced which is a fusion with the N-terminus and/or C-terminus of the remaining residues of the deleted PB2 protein.

A vector for vRNA production of the mutant PB2 gene segment is introduced into a cell along with a vector or vectors for vRNA production for PA vRNA, PB1 vRNA, NP vRNA, HA vRNA, NA vRNA, M vRNA, and NS (NS1 and/or NS2) vRNA, and vectors for mRNA (protein) production for one or more of PA, PB1, PB2, and NP, or vectors for mRNA production of up to three of PA, PB1, PB2, and NP, where the cell stably expresses the remaining viral protein(s), and optionally expresses HA, NA, M, e.g., M1 and M2, NS1 and/or NS2. The vRNA for the mutant PB2 gene segment may be incorporated into virions at an efficiency that is at least 1%, 5%, 10%, or 30%, or at least 50%, that of a corresponding wild-type PB2 vRNA.

In one embodiment, the influenza virus of the invention elicits both systemic and mucosal immunity at the primary portal of infection. Thus, the invention provides a live, attenuated vaccine or immunogenic composition comprising the recombinant biologically contained virus of the invention, and a method of using the vaccine or immunogenic composition to immunize a vertebrate, e.g., an avian or a mammal, such as a human, or induce an immune response in a vertebrate, respectively. In one embodiment, the composition or vaccine is formulated for intranasal administration. In one embodiment, the recombinant biologically contained virus in a vaccine comprises a HA gene segment for influenza A virus HA, e.g., H1, H2, H3, H5, H7, or H9 HA. In one embodiment, the HA in the recombinant biologically contained virus in a vaccine is modified at the HA cleavage site. In one embodiment, the vaccine comprises at least one influenza virus strain that is different than the recombinant biologically contained virus of the invention, for instance, the vaccine comprises two or three different influenza viruses.

The invention provides a plurality of vectors to prepare an infectious, biologically contained 8 segment influenza A virus having one or more vectors which include transcription cassettes for vRNA production and transcription cassettes for mRNA production. The transcription cassettes for vRNA production are a transcription cassette comprising a promoter for vRNA production, e.g., a PolI promoter, operably linked to an influenza virus PA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus PB1 DNA in an orientation for genomic viral RNA production linked to a transcription termination sequence that results in influenza virus-like vRNA termini, for instance, PolI transcription termination sequence, a transcription cassette comprising a promoter for vRNA production, e.g., a PolI promoter, operably linked to a mutant influenza virus PB2 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus HA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NP DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus M DNA in an orientation for genomic viral RNA production linked to a transcription termination sequence that results in influenza virus-like vRNA termini, for instance, a PolI transcription termination sequence, and a transcription cassette comprising a promoter for vRNA production, e.g., a PolI promoter, operably linked to an influenza virus NS (NS1 and NS2) DNA in an orientation for genomic viral RNA production linked to a transcription termination sequence that results in influenza virus-like vRNA termini, for instance, a PolI transcription termination sequence. The mutant PB2 DNA includes 5' and 3' incorporation sequences flanking a heterologous nucleotide sequence and does not include contiguous sequences corresponding to sequences that encode a functional PB2. The transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, and a transcription cassette comprising a PolII promoter operably linked to a DNA coding region for influenza virus NP linked to a PolII transcription termination sequence, and optionally a transcription cassette comprising a PolII promoter operably linked to a DNA coding region for influenza virus one or more of PB2, HA, NA, NS1, NS2, M1 and/or M2 linked to a PolII transcription termination sequence. Further provided is a composition having the vectors, and a method which employs the vectors.

The invention also provides a plurality of vectors to prepare an infectious, biologically contained 8 segment influenza B virus having one or more vectors which include transcription cassettes for vRNA production and transcription cassettes for mRNA production. The transcription cassettes for vRNA production are a transcription cassette comprising a promoter for vRNA production, e.g., a PolI promoter, operably linked to an influenza virus PA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus PB1 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to a mutant influenza virus PB2 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus HA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NA and NB DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NP DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus M DNA in an orientation for genomic viral RNA production linked to a transcription termination sequence that results in influenza virus-like vRNA termini, for instance, a PolI transcription termination sequence, and a transcription cassette comprising a PolI promoter operably linked to an influenza virus NS (NS1 and NS2) DNA in an orientation for genomic viral RNA production linked to a PolI transcription termination sequence, The mutant PB2 DNA is includes 5' and 3' incorporation sequences, optionally flanking a heterologous nucleotide sequence, and does not include contiguous sequences corresponding to sequences that encode a functional PB2. The transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, and a transcription cassette comprising a PolII promoter operably linked to a DNA coding region for influenza virus NP linked to a PolII transcription termination sequence, and optionally a transcription cassette comprising a PolII promoter operably linked to a DNA coding region for influenza virus one or more of PB2, HA, NA, NS1, NS2, M1 and/or BM2 linked to a PolII transcription termination sequence. Further provided is a composition having the vectors and a method which employs the vectors.

In one embodiment, the promoter in a vRNA vector includes but is not limited to a RNA polymerase I (PolI) promoter, e.g., a human RNA PolI promoter, a RNA polymerase II (PolII) promoter, a RNA polymerase III promoter, a SP6 promoter, a T7 promoter, or a T3 promoter. In one embodiment, one or more vRNA vectors include a PolII promoter and ribozyme sequences 5' to influenza virus sequences and the same or different ribozyme sequences 3' to the influenza virus sequences. In one embodiment, the mutant PB2 gene segment is in a vector and is operably linked to a promoter including, but not limited to, a RNA PolI promoter, e.g., a human RNA PolI promoter, a RNA PolII promoter, a RNA polymerase III promoter, a SP6 promoter, a T7 promoter, or a T3 promoter. In one embodiment, the vRNA vectors include a transcription termination sequence including, but not limited to, a PolI transcription termination sequence, a PolII transcription termination sequence, or a PolIII transcription termination sequence, or one or more ribozymes.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid. In one embodiment, one or more vectors for vRNA production are on the same plasmid (see, e.g., U.S. published application No. 20060166321, the disclosure of which is incorporated by reference herein). In one embodiment, one or more vectors for mRNA production are on the same plasmid (see, e.g., U.S. published application No. 2006/0166321). In one embodiment, the vRNA vectors employed in the method are on one plasmid or on two or three different plasmids. In one embodiment, the mRNA vectors for PA, PB1, and NP, and optionally PB2, employed in the method are on one plasmid or on two or three different plasmids.

Also provided is a host cell comprising a vector expressing PB2, e.g., PB2 from PR8 or other master vaccine strain. In one embodiment, the PB2 has at least 90%, 95%, 98%, 99% or 100% identity to PB2 encoded by SEQ ID NO:3. In one embodiment, the host cell is transduced with a viral vector, e.g., a vector which is stably maintained in the cell as an episome or integrated into a chromosome, such as a lentiviral or retroviral vector. In one embodiment, the host cell further includes one or more vectors which include transcription cassettes for transient vRNA production and transcription cassettes for transient mRNA production. The transcription cassettes for vRNA production are a transcription cassette comprising a promoter for vRNA production, e.g., a PolI promoter, operably linked to an influenza virus PA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter operably linked to an influenza virus PB1 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to a mutant influenza virus PB2 DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus HA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NA DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus NP DNA in an orientation for genomic viral RNA production linked to a transcription termination sequence that results in influenza virus-like vRNA termini, for instance, a PolI transcription termination sequence, a transcription cassette comprising a promoter for vRNA production, e.g., a PolI promoter, operably linked to an influenza virus M DNA in an orientation for genomic viral RNA production linked to a transcription termination sequence that results in influenza virus-like vRNA termini, for instance, a PolI transcription termination sequence, and a transcription cassette comprising a promoter for vRNA production, e.g., a PolI promoter, operably linked to an influenza virus NS (NS1 and NS2) DNA in an orientation for genomic viral RNA production linked to a transcription termination sequence that results in influenza virus-like vRNA termini, for instance, a PolI transcription termination sequence. The mutant PB2 DNA includes 5' and 3' incorporation sequences, optionally flanking a heterologous nucleotide sequence, and does not include contiguous sequences corresponding to sequences that encode a functional PB2.

The transcription cassettes for mRNA production are a transcription cassette comprising a PolII promoter operably linked to a DNA coding region for influenza virus PA linked to a PolII transcription termination sequence, a transcription cassette comprising a PolII promoter operably linked to a DNA coding region for influenza virus PB1 linked to a PolII transcription termination sequence, and a transcription cassette comprising a PolII promoter operably linked to a DNA coding region for influenza virus NP linked to a PolII transcription termination sequence. The host cell does not include sequences corresponding to PB2 coding sequences for vRNA production of a wild-type PB2 viral gene segment.

The invention also provides a method to prepare influenza virus, e.g., using a host cell of the invention. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with virus of the invention. In another embodiment, the invention includes contacting the cell with one or more vectors, either vRNA or protein production vectors, prior to other vectors, either vRNA or protein production vectors.

In one embodiment, the invention provides a method of preparing a recombinant influenza virus comprising a mutant PB2 viral gene segment. The method comprises contacting a host cell with a plurality of influenza vectors, including a vector comprising the mutant PB2 gene segment sequence, so as to yield recombinant virus. For example, the host cell is contacted with vectors for vRNA production including a vector comprising a promoter for vRNA production operably linked to an influenza virus PA DNA linked to a transcription termination sequence, a vector comprising a promoter for vRNA production operably linked to an influenza virus PB1 DNA linked to a transcription termination sequence, a vector comprising a promoter for vRNA production operably linked to a mutant influenza virus PB2 DNA linked to a transcription termination sequence, a vector comprising a promoter for vRNA production operably linked to an influenza virus HA DNA linked to a transcription termination sequence, a vector comprising a promoter for vRNA production operably linked to an influenza virus NP DNA linked to a transcription termination sequence, a vector comprising a promoter for vRNA production operably linked to an influenza virus NA DNA linked to a transcription termination sequence, a vector comprising a promoter for vRNA production operably linked to an influenza virus M DNA linked to a transcription termination sequence, and a vector comprising a promoter for vRNA production operably linked to an influenza virus NS (NS1 and NS2) DNA linked to a transcription termination sequence, wherein the mutant PB2 DNA is in an orientation for genomic vRNA production and includes 5' and 3' incorporation sequences, optionally flanking a heterologous nucleotide sequence, and does not include contiguous sequences corresponding to those for a functional PB2, and vectors for mRNA production including a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus NP, wherein the cell is not contacted with sequences corresponding to PB2 coding sequences for vRNA production. Optionally, the host cell is contacted with a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding a M2 protein, e.g., a mutant M2 protein, and a vector comprising a promoter operably linked to a DNA segment encoding influenza virus NS1 and/or NS2. In one embodiment, separate vectors for M1 and M2 mRNA, and/or for NS1 and NS2 mRNA are provided and employed.

In one embodiment of a method of preparing a recombinant biologically contained influenza virus of the invention, each transcription cassette is on a plasmid vector. In one embodiment of a method of preparing a biologically contained influenza virus of the invention, one or more transcription cassettes are on one or more plasmid vectors, e.g., one plasmid vector has transcription cassettes for vRNA production of PA, PB1, HA, NP, NA, M1, NS1 and/or NS2, and the mutant PB2 cDNAs. In one embodiment of a method of preparing a biologically contained influenza virus of the invention, one plasmid vector has one of the transcription cassette for mRNA production and another plasmid vector has the other transcription cassettes for mRNA production. In one embodiment of a method of preparing a biologically contained influenza virus of the invention, three plasmid vectors for mRNA production are employed, each with one of the transcription cassettes for mRNA production. In one embodiment of a method of preparing a biologically contained influenza virus of the invention, one plasmid vector has six of the transcription cassettes for vRNA production and another plasmid vector has the other transcription cassette for vRNA production, e.g., one plasmid vector has one of the transcription cassettes for mRNA production and another plasmid vector has the other transcription cassettes for mRNA production. In one embodiment of a method of preparing a biologically contained influenza virus of the invention, three plasmid vectors for mRNA production are employed. In one embodiment of a method of preparing a biologically contained influenza virus of the invention, one plasmid has the three transcription cassettes for mRNA production. In one embodiment of a method of preparing a biologically contained influenza virus of the invention, the HA cDNA encodes an avirulent cleavage site. In one embodiment of a method of preparing a biologically contained influenza virus of the invention, the HA and NA are from the same virus isolate. In one embodiment of a method of preparing a biologically contained influenza virus of the invention, the HA is a type B HA.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host. In one embodiment, the PolI promoter for each PolI containing vector is the same. In one embodiment, the PolI promoter is a human PolI promoter. In one embodiment, the PolII promoter for each PolII containing vector is the same. In one embodiment, the PolII promoter for two or more, but not all, of the PolII containing vectors, is the same. In one embodiment, the PolII promoter for each PolII containing vector is different.

In another embodiment, the method includes contacting a host cell with a vector having a PolII promoter linked to a PolI transcription termination sequence linked to an influenza virus PA DNA linked to a PolI promoter linked to a PolII transcription termination sequence (a bidirectional cassette), a vector having a PolII promoter linked to a PolII transcription termination sequence linked to an influenza virus PB1 DNA linked to a PolI promoter linked to a PolI transcription termination sequence, a vector having a PolII promoter linked to a PolI transcription termination sequence linked to a mutant influenza virus PB2 DNA linked to a PolI promoter linked to a PolII transcription terminator sequence, a vector having a PolII promoter linked to a PolI transcription termination sequence linked to an influenza virus HA DNA linked to a PolI promoter linked to a PolII transcription termination sequence, a vector having a PolII promoter linked to a PolI transcription termination sequence linked to an influenza virus NP DNA linked to a PolI promoter linked to a PolII transcription termination sequence, a vector having a PolII promoter linked to a PolI transcription termination sequence linked to an influenza virus NA DNA linked to a PolI promoter linked to a PolII transcription termination sequence, a vector having a PolII promoter linked to a PolI transcription termination sequence linked to an influenza virus M DNA linked to a PolI promoter linked to PolII transcription termination sequence, and a vector having a PolII promoter linked to a PolI transcription termination sequence linked to an influenza virus NS1 and/or NS2 DNA linked to a PolI promoter linked to PolII transcription termination sequence. The host cell comprises PB2 DNA expressing a PB2 protein, e.g., from a chicken beta-actin promoter. No sources of vRNA for wild-type PB2 are present so that replication-incompetent virus is provided.

In one embodiment, the promoter for vRNA production in a bidirectional cassette includes but is not limited to a RNA polymerase I (PolI) promoter, e.g., a human RNA PolI promoter, a RNA polymerase II (PolII) promoter, a RNA polymerase III promoter, a SP6 promoter, a T7 promoter, or a T3 promoter. In one embodiment, one or more vRNA vectors include a PolII promoter and ribozyme sequences 5' to influenza virus sequences and the same or different ribozyme sequences 3' to the influenza virus sequences. In one embodiment, the mutant PB2 gene segment is in a vector and is operably linked to a promoter including, but not limited to, a RNA PolI promoter, e.g., a human RNA PolI promoter, a RNA PolII promoter, a RNA polymerase III promoter, a SP6 promoter, a T7 promoter, or a T3 promoter. In one embodiment, the vRNA vectors include a transcription termination sequence including, but not limited to, a PolI transcription termination sequence, a PolII transcription termination sequence, or a PolIII transcription termination sequence, or one or more ribozymes. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

The plurality of vectors, compositions and host cells of the invention may also include another vector for vRNA production or protein production that includes heterologous sequences, e.g., for a therapeutic or prophylactic gene of interest e.g., an immunogen for a cancer associated antigen or for a pathogen such as a bacteria, a noninfluenza virus, fungus, or other pathogen. For example, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

In one embodiment, the recombinant virus of the invention includes one or more genes from influenza A virus. In another embodiment, the recombinant virus of the invention may include one or more genes from influenza B virus, e.g., an influenza B HA gene. In yet another embodiment, the recombinant virus of the invention may include one or more genes from influenza C virus. The DNA for vRNA production of NA may be from any NA, e.g., any of N1-N9, a chimeric NA sequence or any non-native NA sequence, and the DNA for vRNA production of HA may be from any HA, e.g., H1-H16, a chimeric HA sequence or any non-native HA sequence. In one embodiment, the DNAs for vRNA production may be for an influenza B or C virus. In one embodiment, other attenuating mutations may be introduced to the vectors, e.g., a mutation in a HA cleavage site that results in a site that is not cleaved. The DNAs for vRNA production of NA and HA may be from different strains or isolates relative to those for the (6:1:1 reassortants) or from the same strain or isolate (6:2 reassortants), the NA may be from the same strain or isolate as that for the internal genes (7:1 reassortant), or one of the internal genes, NA and HA may be from the same strain or isolate (5:3 reassortant).

Viruses that may provide the internal genes for reassortants within the scope of the invention include viruses that have high titers in Vero cells, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ EID$_{50}$/mL, e.g., at least $10^8$ EID$_{50}$/mL, $10^9$ EID$_{50}$/mL or $10^{10}$ EID$_{50}$/mL; high titers in MDCK, e.g., AX5, cells, e.g., titers of at least about $10^7$ PFU/mL, e.g., at least $10^8$ PFU/mL, or high titers in two of more of those host cells. In one embodiment, the DNAs for vRNA production of PB1 vRNA, mutant PB2 vRNA, PA vRNA, NP vRNA, M vRNA (for M1 and/or M2 or M1 and/or BM2), and/or NS vRNA (for NS1 and/or NS2), may have sequences from an influenza virus that replicates to high titers in cultured mammalian cells such as AX4 cells, Vero cells or PER.C6® cells and also optionally embryonated eggs, and/or from a vaccine virus, e.g., one that does not cause significant disease in humans.

For example, reassortants with internal genes from other PR8 isolates or vaccine viruses may be employed in recombinant reassortant viruses of the invention. In particular, 5:1:2 reassortants having PR8(UW) PB1, PB2, PA, NP, and M ("5") and PR8(Cam) NS ("1"); 6:1:1 reassortants having PR8(UW) NA, PB1, PB2, PA, NP, and M ("6") and PR8 (Cam) NS ("1") gene segments; and 7:1 reassortants having PR8(UW) PB1, PB2, PA, NP, M, NA, and NS ("7") gene segments may be employed.

In one embodiment, the DNAs for the internal genes for PB1, PB2, PA, NP, M, and NS encode proteins with substantially the same activity as a corresponding polypeptide encoded by one of SEQ ID NOs:1-6 or 10-15. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:1-6 or 10-15. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 or 33-38 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs:1-6 or 10-15. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:1-6 or 10-15. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:1-6 or 10-15.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The methods include administering to a host organism, e.g., a mammal, an effective amount of the influenza virus of the invention, e.g., a live or inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. In one embodiment, two to three doses are administered. The vaccine may be multivalent as a result of the heterologous nucleotide sequence introduced into a viral gene segment in the influenza virus of the invention. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

In one embodiment, the influenza viruses of the invention may be vaccine vectors for influenza virus and for at least one other pathogen, such as a viral or bacterial pathogen, or for a pathogen other than influenza virus, pathogens including but not limited to, lentiviruses such as HIV, hepatitis B virus, hepatitis C virus, herpes viruses such as CMV or HSV, Foot and Mouth Disease Virus, Measles virus, Rubella virus, Mumps virus, human Rhinovirus, Parainfluenza viruses, such as respiratory syncytial virus and human parainfluenza virus type 1, Coronavirus, Nipah virus, Hantavirus, Japanese encephalitis virus, Rotavirus, Dengue virus, West Nile virus, *Streptococcus pneumoniae, Mycobacterium tuberculosis, Bordetella pertussis,* or *Haemophilus influenza*. For example, the biologically contained influenza virus of the invention may include sequences for H protein of Measles virus, viral envelope protein E1 of Rubella virus, HN protein of Mumps virus, RV capsid protein VP1 of human Rhinovirus, G protein of Respiratory syncytial virus, S protein of Coronavirus, G or F protein of Nipah virus, G protein of Hantavirus, E protein of Japanese encephalitis virus, VP6 of Rotavirus, E protein of Dengue virus, E protein of West Nile virus, PspA of *Streptococcus pneumonia*, HSP65 from *Mycobacterium tuberculosis*, IRP1-3 of *Bordetella pertussis*, or the heme utilization protein, protective surface antigen D15, heme binding protein A, or outer membrane protein P1, P2, P5 or P6 of *Haemophilus influenza*.

Further provided is a method to detect neutralizing antibodies for a selected influenza virus strain in a physiological sample of a vertebrate. The method includes contacting the sample, a recombinant virus of the invention which expresses HA and/or NA of the selected strain, and cells susceptible to influenza virus infection. The presence or amount of the reporter or the antigen in the cells is detected, wherein the absence of the reporter or antigen or a reduced amount of the reporter or antigen in the sample relative to a control sample, is indicative of a vertebrate that has been infected with the influenza virus strain.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 1. Schematic diagram of mutant PB2 vRNAs and their efficiencies in virion formation and virion incorporation. The numbers of VLPs and the virion incorporation efficiencies of mutant PB2 vRNAs were determined by using the numbers of WSN HA- and GFP-expressing cells as a denominator. All mutants are shown in the negative-sense orientation. Each mutant contains the GFP reading frame (green bar); 27 and 34 nucleotides of the 3' and 5' noncoding regions, respectively (gray bars); and coding regions of various lengths (black bars). The dotted lines represent deleted sequences of the PB2 coding region. PB2(−) indicates the omission of this vRNA (i.e., VLPs were generated using only seven vRNA segments).

FIG. 2A-FIG. 2I. Exemplary vaccine virus internal gene sequences (SEQ ID NOs:1-8 and 10-15).

FIG. 4. Accommodation of various HA genes in PB2-KO virus. HA expression in PB2-KO virus-infected cells. AX4/PB2 cells were infected with PR8/PB2-GFP, WSN/PB2-GFP, CA04/PB2-GFP, or VN1203/PB2-GFP. At 16 hours post-infection, the cells were stained with monoclonal antibodies specific for WSN, CA04, or VN1203 HA protein. The expression of HA and GFP were examined by using fluorescence microscopy.

FIG. 11. Detection of heterologous antigen expression after infection of cells with PB2-KO virus having sequences for pspA of pneumococcus (*S. pneumoniae*). Anti-influenza virus antibodies and anti-PspA antibodies were used to detect expression of influenza virus and PspA proteins in cells with PB2-KO-GFP or PB2-KO-PspA.

FIG. 12. Growth kinetics of PB2-KO-PspA in cells that do not express PB2 and cells that stably express PB2.

FIG. 16. Survival post-challenge of mice immunized three times with PB2-KO-PspA and challenged with 10 $LD_{50}$ or 100 $LD_{50}$ of influenza virus.

FIG. 19. Survival post-challenge of mice immunized three times with PB2-KO-PspA and challenged with $2 \times 10^7$ CFU pneumococcus WU2 (a lethal strain)/mouse.

DETAILED DESCRIPTION

Definitions

Figure 3:
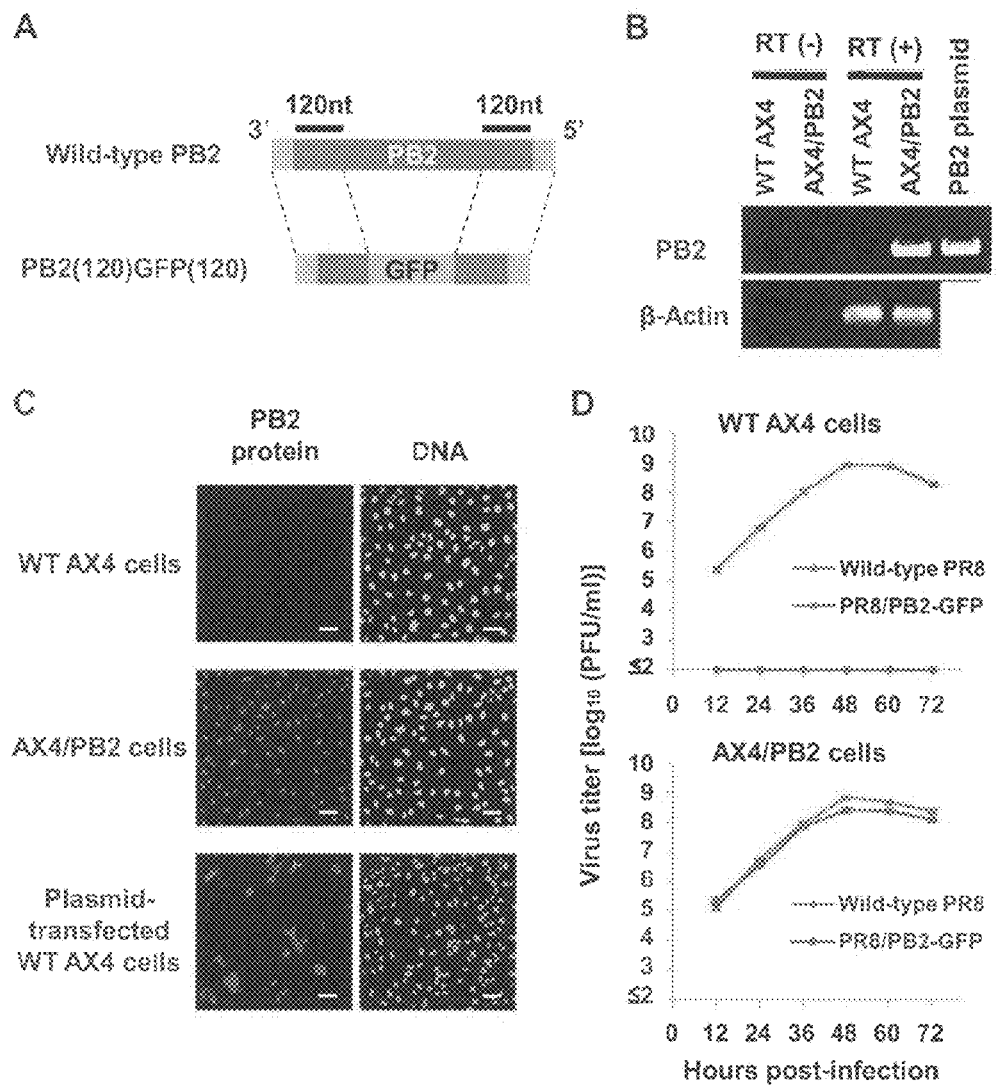
FIG. 3. Characterization of PR8/PB2-GFP virus. A) Schematic diagram of wild-type PB2 and PB2(120)GFP(120) vRNAs. PB2(120)GFP(120) vRNA possesses the 3' noncoding region, 120 nucleotides of the coding sequence of PB2 vRNA, the GFP gene, and 120 nucleotides of the 3' coding and the 5' noncoding regions of PB2 vRNA. The noncoding region and coding regions of PB2 vRNA are represented by gray and red bars, respectively. The GFP gene is represented by the green bar. B) PB2 gene expression in AX4/PB2 cells (AX4 cells are derived from MDCK cells). RNA was extracted from both wild-type AX4 and AX4/PB2 cells. RT-PCR was performed by using an oligo(dT) primer followed by cDNA synthesis and PCR with PB2—(upper panel) or canine beta-actin—(lower panel) specific primers. C) PB2 protein expression in AX4/PB2 cells. Cells were reacted with an anti-PB2 antibody 18/1 (Hatta et al., 2000) (left panels) and Hoechst 33342 (right panels). Scale bar, 50 μm. D) Growth kinetics of PR8/PB2-GFP monitored over 72 hours. Wild-type AX4 (upper panel) and AX4/PB2 (lower panel) cells were infected with wild-type PR8 (red) or PR8/PB2-GFP (green) viruses at an MOI of 0.001. Supernatants collected at the indicated time points were assayed for infectious virus in plaque assays in AX4/PB2 cells.

As used herein, an "infectious, biologically contained" virus means that the virus is incapable of producing progeny in normal cells or incapable of significant replication in vitro or in vivo, e.g., titers of less than about $10^2$ to $10^3$ PFU/mL, in the absence of helper virus or a viral protein stably supplied in trans.

A used herein, "replication-deficient" virus means that the virus can replicate to a limited extent in vitro or in vivo, e.g., titers of at least about $10^2$ to $10^3$ PFU/mL, in the absence of helper virus or a viral protein supplied in trans.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro so that its sequence is not naturally occurring or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" nucleotide sequence is from a source other than a parent influenza virus, e.g., a reporter gene or a gene from another virus or organism, e.g., a bacterium, or is from an influenza virus source but is in a context that does not mimic a native influenza virus genome, e.g., it is a subset of a full length influenza virus gene segment and is in a non-native context, e.g., fused to truncated PB2 coding sequences.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=-4, and a comparison of both strands. For amino acid sequences, the BLASTP program may use as defaults a wordlength (W) of 3, an expectation (E) of 10, and the BLOSUM62 scoring matrix. See http://www.ncbi.nlm.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus

The life cycle of viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell (reviewed by Roizman and Palese, 1996). Different viral proteins play a role in each of these steps.

The influenza A virus is an enveloped negative-strand virus with eight RNA segments encapsidated with nucleoprotein (NP) (reviewed by Lamb and Krug, 1996). The eight single-stranded negative-sense viral RNAs (vRNAs) encode a total of ten to eleven proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, the M segment of influenza B virus encodes two proteins, M1 and BM2, through a termination-reinitiation scheme of tandem cistrons, and the NA segment encodes the NA and NB proteins from a bicistronic mRNA. Influenza C virus, which has 7 vRNA segments, relies on spliced transcripts to produce M1 protein; the product of the unspliced mRNA is proteolytically cleaved to yield the CM2 protein. In addition, influenza C virus encodes a HA-esterase (HEF) rather than individual HA and NA proteins.

Spanning the viral membrane for influenza A virus are three proteins: hemagglutinin (HA), neuraminidase (NA), and M2. The extracellular domains (ectodomains) of HA and NA are quite variable, while the ectodomain domain of M2 is essentially invariant among influenza A viruses. The M2 protein which possesses ion channel activity (Pinto et al., 1992), is thought to function at an early state in the viral life cycle between host cell penetration and uncoating of viral RNA (Martin and Helenius, 1991; reviewed by Helenius, 1992; Sugrue et al., 1990). Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm (reviewed by Helenius, 1992). In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment (Hay et al., 1985; Ohuchi et al., 1994; Takeuchi and Lamb, 1994).

Cell Lines that can be Used in the Present Invention

Any cell, e.g., any avian or mammalian cell, such as a human, e.g., 293T or PER.C6® cells, or canine, bovine, equine, feline, swine, ovine, rodent, for instance mink, e.g., MvLu1 cells, or hamster, e.g., CHO cells, non-human primate, e.g., Vero cells, or non-primate higher vertebrate cells, e.g., MDCK cells, including mutant cells such as AX4 cells, which support efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular components, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines.

Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines.

Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the M2 gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 10 to 100 μg, such as about 15 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, such as about 15 μg, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Health Service (PHS), which is usually 15 μg, per component for older children □3 years of age, and 7.5 μg per component for older children <3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

The invention will be described by the following nonlimiting examples.

Example I

PB2 Incorporation Sequences

Most defective RNA segments of influenza A viruses retain 150 to 300 nucleotides corresponding to the 5' and 3' ends of the respective gene segment (Duhaut et al., 1998; Jennings et al., 1983; Noble et al., 1995; and Odagiri et al., 1990), indicating that these 300 to 600 nucleotides may possess the structural features required for efficient genome packaging. To identify the regions in the PB2, PB1, and PA vRNAs that are critical for vRNA virion incorporation and virion formation, plasmids were generated in which the GFP gene is flanked by the noncoding regions and portions of the coding regions derived from both termini [PB2(300)GFP(300), PB1 (300)GFP(300), and PA(120)GFP(120)]. Transfection of such a plasmid into 293T cells, together with expression plasmids for the PB2, PB1, PA, and NP proteins (minimal components for transcription and replication of vRNAs), resulted in the expression of GFP in cells, indicating that the chimeric vRNAs were synthesized by the cellular RNA polymerase I and transcribed into mRNA by the viral proteins produced by the expression plasmids.

To calculate the vRNA virion incorporation efficiencies, the number of virions containing a test vRNA must be compared with the total number of VLPs. The total number of VLPs could be determined by inoculating cells with VLPs and then counting the number of cells expressing a given influenza virus protection. To ensure that the number of infectious VLPs determined by this method was not drastically affected by the viral gene product selected as a marker, we determined the number of cells expressing either HA or NP. Because we were testing the incorporation efficiencies of the PB2, PB1, and PA vRNAs, helper virus was needed to provide functional polymerase proteins. To distinguish between the HA and NP proteins expressed from out test VLPs (derived from WSN virus) and those expressed from the helper PR8 virus, we used antibiotics that recognize the WSN HA and NP proteins, but not their PR8 virus counterparts.

To establish a system that allowed the assessment of the number of VLPs generated, 293T cells were transfected with a plasmid for the transcription of a test vRNA (derived from the PB2, PB1, or PA segment), 7 plasmids for the production of the remaining vRNAs, and 10 expression plasmids for the expression of the viral proteins (i.e., PB2, PB1, PA, HA, NP, NA, M1, M2, NS1, and NS2). Forty-eight hours later, VLP-containing supernatants derived from transfected cells were mixed with PR8 helper virus and used to infect MDCK cells. Twelve hours postinfection, the number of cells that expressed either HA or NP protein were determined. For all three vRNAs, the numbers of HA- or NP-expressing cells differed by less than a factor of 3; for example, using the PB2(300)GFP(300) test vRNA, 240,800 HA-expressing cells versus 353,200 NP-expressing cells were detected. Therefore, for the subsequent experiments, the number of HA-expressing cells was employed as an indicator of the efficiency of infectious virion formation. The incorporation efficiencies of test vRNAs were thus calculated by dividing the number of GFP-expressing cells (as a marker for the test vRNA) by the sum of the number of HA-expressing cells (as a marker for the number of virions) plus the number of GFP-expressing cells.

Sequences in the coding region of the PB2 vRNA affect infectious virion formation and vRNA virion incorporation. To delineate the sequences in the PB2 vRNA that are critical for virion formation and/or vRNA virion incorporation, a series of plasmids was generated for the production of PB2 vRNAs that express GFP and contain portions of the PB2 coding region derived from both termini (FIG. 1), in addition to the noncoding regions of the PB2 vRNA (FIG. 1). The numbers of VLPs and the incorporation efficiencies of the test vRNAs were determined as described above.

With PB2(300)GFP(300), which contains 300 nucleotides corresponding to the 5' and 3' coding regions of the PB2 vRNA, about $2.8 \times 10^6$ VLPs per mL were detected. Stepwise deletion of the coding sequences at the 3' end of the vRNA (referred to as the 3' coding region) had only moderate effects on the efficiency of VLP production; PB2(0)GFP(120), which lacks the entire coding region of the 3' end, yielded about $1 \times 10^6$ VLPs/mL. Deletion of the coding sequences at the 5' end of the vRNA (referred to as the 5' coding region) [PB2(120)GFP(0)], however, reduced VLP production by 98% of that of PB2(300)GFP(300) and yielded a number of VLPs comparable to that obtained in the absence of the PB2 vRNA [PB2(−)]. This result suggests that sequences in the 5' coding region of the PB2 vRNA are critical for the efficient generation of infectious virions. Further analysis revealed that 30 nucleotides of the 5' coding region are critical for this effect [compare the numbers of VLPs for PB2(120)GFP(0) and PB2(120)GFP(30)].

With regard to the efficiencies of vRNA virion incorporation. PB2(300)GFP(300), 54.7% of the VLPs contained the PB2(300)GFP(300) test vRNA, indicating that the 300 terminal nucleotides at both ends are sufficient for virion incorporation. To achieve the incorporation efficiencies observed for wild-type segments, internal PB2 coding sequences would likely be required. Stepwise deletion of nucleotides in the 3' coding region of the PB2 vRNA had only moderate effects provided 30 or more nucleotides were retrained; the deletion of these remaining 30 nucleotides, however, reduced the virion incorporation efficiency to 29.5% for PB2(0)GFP (120), demonstrating that this region is important for the efficient incorporation of the PB2 vRNA into virions. For PB2 vRNAs that lack a functional packaging sequence in the 3' coding region, sequences in the 5' coding region do contribute to virion incorporation, as exemplified by the inability of the PB2(0)GFP(0) test vRNA to be incorporated.

Deletions in the 5' coding region only, by contrast, had no effect on incorporation efficiencies, as demonstrated by a 75.7% incorporation rate for PB2(120)GFP(0). Thus while the use of this test vRNA produced a very low number of infectious VLPs, the test vRNA was efficiently incorporated into these particles. This finding suggests that sequences in the PB2 vRNA are involved in two biologically distinct processes: efficient infectious virion formation (a function residing in the 5' coding region) and efficient vRNA incorporation into particles (a function primarily residing in the 3' coding region).

The difference in packaging efficiencies could reflect differences in transcription levels of the test vRNAs in 293T cells. To exclude this possibility, the levels of PB2(0)GFP(0) and PB2(120)GFP(120) in plasmid-transfected 293T cells were examined using real-time PCR. The amount of PB2(0) GFP(0) vRNA was 52% of that of PB2(120)GFP(120); however, this difference is unlikely to explain the 99% reduction in VLP generation and the abrogation of vRNA virion incorporation.

PB2 vRNA is more critical for efficient infectious virion generation than the PB1 or PA vRNA. Thus, a hierarchy may exist in which the PB2 vRNA is critical for the efficient virion incorporation of other vRNAs, while the omission of other segments is tolerable to some extent.

Omission of the PB2 vRNA resulted in an about 30-fold reduction in VLP production, whereas omission of the other vRNA segments resulted in 1.4- to 5.1-fold reductions. These results provided further proof of a hierarchy among the vRNA segments with respect to the importance of the individual vRNAs for the incorporation of the other vRNA segments.

Example II

The stable expression of a foreign gene in a replication-incompetent influenza virus allows for the effective tracking of the manipulated virus. In pursuit of a biologically contained foreign gene-expressing virus with extensive applications in the field of virology, the PB2 protein, an influenza viral polymerase subunit that forms part of the trimeric viral RNA-dependent RNA polymerase that is essential for virus replication was selected. The partial coding sequences of the 3' and 5' ends of the PB2 viral RNA (vRNA) confer its more critical role in efficient infectious virion generation relative to the other vRNAs in the vRNA hierarchy (Example I and Muramoto et al., 2006). This finding suggests that a PB2-knock out (PB2-KO) influenza virus harboring a reporter gene flanked by the coding and non-coding sequences of the PB2 vRNA would replicate only in PB2-expressing cells while stably expressing the reporter gene.

A cell line that stably expresses PB2 protein was established and used to characterize a PB2-KO virus that possesses the GFP gene. The potential for various virus strain-derived HA and NA genes, as well as other reporter genes, to be accommodated by the PB2-KO virus, was also investigated. Further, the PB2-KO virus was employed as a platform to screen neutralizing antibodies against 2009 pandemic viruses.

Methods

Cells.

293T human embryonic kidney cells (a derivative of the 293 line into which the gene for simian virus 40 T antigen was inserted (DuBridge et al., 1987)) were maintained in Dulbecco's modified Eagle medium (Lonza) supplemented with 10% fetal calf serum (Invitrogen). Madin-Darby canine kidney (MDCK) cells were maintained in minimum essential medium (MEM; Invitrogen) supplemented with 5% newborn calf serum (NCS; Sigma, St. Louis, Mo.). AX4 cells, derived from MDCK cells and transfected with the cDNA of human 2,6-sialyltransferase (Hatakeyama et al., 2005), were maintained in 5% NCS/MEM+puromycin (2 μg/mL). AX4/PB2 cells (AX4 cells stably expressing the PB2 protein derived from A/Puerto Rico/8/34 (H1N1, PR8), established by transduction with a retroviral vector, see the Results section) were maintained in 5% NCS/MEM+puromycin (2 μg/mL)+blasticidin (10 μg/mL). All cells were maintained at 37° C. in 5% $CO_2$.

Reverse Genetics and Virus Propagation.

Reverse genetics was performed with plasmids that contained the cDNAs of the PR8 viral genes between the human RNA polymerase 1 promoter and the mouse RNA polymerase 1 terminator (referred to as Pol1 plasmids) and eukaryotic protein expression plasmids (NP, PA, PB1, and PB2) under the control of the chicken β-actin promoter (Niwa et al., 1991), as described in Neumann et al. (1999). Briefly, the wild-type PR8 virus was engineered by using the eight previously produced wild-type constructs derived from PR8 (Horimoto et al., 2007); whereas the PB2-KO mutant was comprised of pPolIPB2(120)GFP(120) (FIG. 3A) (Muramoto et al., 2006) and the remaining seven segmental PolI plasmids. The pPolIPB2(120)GFP(120) plasmid contains the A/WSN/33 (H1N1, WSN)-derived 3' PB2 non-coding region, 120 nucleotides that correspond to the PB2 coding sequence at the 3' end of the vRNA followed by the GFP coding sequence, 120 nucleotides that correspond to the PB2 coding sequence at the 5' end of the vRNA, and finally the 5' PB2 non-coding region (Muramoto et al., 2006). Likewise, pPolIPB2(120)Fluc(120) and pPolIPB2(120)Rluc(120) were constructed to generate PB2-KO viruses possessing the firefly luciferase (Fluc) or *Renilla* luciferase (Rluc) genes, respectively. The eight PolI plasmids and protein expression plasmids were mixed with the transfection reagent TransIT-293 (Minis), incubated at room temperature for 15 minutes, and added to $10^6$ 293T cells cultured in Opti-MEM 1 (Invitrogen). Forty-eight hours post-transfection, the supernatant containing wild-type PR8 or PB2-KO virus was harvested and propagated in 10-day-old embryonated chicken eggs or AX4/PB2 cells, respectively. Wild-type CA04 was also generated by using reverse genetics, as described in Yamada et al. (2010), and propagated in MDCK cells. The propagated viruses were titrated by using plaque assays in MDCK cells to determine plaque-forming units (PFU) of virus.

Immunofluorescence Staining of the PB2 Protein.

Confluent AX4 and AX4/PB2 cells seeded in 35 mm glass bottom dishes (Asahi Techno Glass) were fixed in phosphate buffered saline (PBS) containing 4% paraformaldehyde (Wako Pure Chemical Industries Ltd) and permeabilized with 0.1% Triton X-100. Cells were incubated with an anti-PB2 antibody clone 18/1 (Hatta et al., 2000) and further incubated with an Alexa Fluor 594-labeled anti-mouse secondary antibody (Invitrogen) in Hoescht 33342 (Invitrogen). Samples were observed under a confocal laser microscope (LSM510META; Carl Zeiss).

Reverse Transcription-PCR (RT-PCR).

To detect PB2 mRNA in AX4/PB2 cells, total RNA was extracted by using an RNeasy RNA extraction kit (Qiagen Sciences). Viral RNAs were isolated from virions by using a QIAmp viral RNA mini kit (Qiagen Sciences). Reverse transcription and cDNA synthesis were performed by using oligo (dT) primer and SuperScript III reverse transcriptase (Invitrogen). RT-minus samples were prepared as negative controls. The synthesized cDNA was amplified by use of PCR with Phusion PCR polymerase (Finnzymes) and PB2-specific primers. Primer sequences are as follows:

```
forward primer,
                              (SEQ ID NO: 9)
ATGGAAAGAATAAAAGAACTACGA,
and reverse primer
                              (SEQ ID NO: 16)
GCCACAATTATTGCTTCGGC.
```

Growth Kinetics and Virus Titration.

To determine virus growth rates, triplicate wells of confluent AX4 or AX4/PB2 cells were infected at a multiplicity of infection (MOI) of 0.001. After 1 hour of virus adsorption, cells were washed in MEM containing 0.3% BSA, overlaid with MEM containing L-(tosylamido-2-phenyl)ethyl chloromethyl ketone (TPCK)-treated trypsin (0.5 μg/mL). Supernatants were collected every 12 hours for three days and assayed for infectious virus in plaque assays in AX4/PB2 cells.

Immunostaining.

To assess the stability of the GFP reporter gene incorporation in the PB2-KO virus, AX4/PB2 cells were infected with various PB2-KO virus dilutions (undiluted to) $10^{-10}$. The supernatant from the second to last well in which a cytopathic effect (CPE) was observed, was harvested and diluted for subsequent infections. Supernatants from five rounds of virus passaging were subjected to standard virus plaque assays. Once the number of plaques formed was counted, the agar was removed and wells containing plaques were fixed with 100% methanol for 30 minutes. Wells were then washed with PBS and incubated with a monoclonal anti-GFP antibody (clone GFP-20; Sigma-Aldrich) at room temperature for 1 hour. Immunohistochemical staining was performed by using a biotinylated anti-mouse antibody according to the Vectastain Elite ABC kit instructions (Vector Laboratories). GFP-positive plaques were visualized by using Sigma Fast 3,3'-Diaminobenzidine tablets (Sigma), and the number of GFP-positive plaques was calculated as a percentage of the total number of plaques that formed in the respective wells.

Immunofluorescent Staining for HA Protein.

GFP-encoding PB2-KO virus possessing HA and NA vRNAs derived from PR8, WSN, A/California/04/09 (CA04), or A/Vietnam/1203/04 (VN1203) were generated by using reverse genetics, as described above, and propagated in AX4/PB2 cells. The multiple basic amino acid residues in the VN1203 HA cleavage site were replaced with a non-virulent type cleavage sequence. Confluent AX4/PB2 cells were infected with these viruses at an MOI of 0.2-1. At 16 hours post-infection, cells were fixed with 4% paraformaldehyde in PBS and permeabilized with 0.1% Triton X-100. Cells were then incubated with an anti-WSN HA antibody (WS 3-54), an anti-CA04 HA antibody (IT-096; eENZYME), and an anti-H5 HA antibody (VN04-10; Rockland Immunochemicals Inc.) and then further incubated with an Alexa Fluor 594-labeled anti-mouse secondary antibody. Samples were observed under a fluorescence microscope.

Luciferase Assay.

Cells infected with PB2-KO virus encoding Fluc or Rluc gene were subjected to a luciferase assay by using a dual-luciferase reporter assay system (Promega) at 8 hours post-infection according to the manufacturer's instructions. Fluc and Rluc activities were measured with a microplate reader Infinite M1000 (Tecan).

Microneutralization Assay.

Sera were collected from two ferrets infected with $10^6$ PFU of wild-type CA04 three weeks post-infection and from two uninfected ferrets. Two-fold serial dilutions of receptor-destroying enzyme (DENKA SEIKEN CO., LTD)-treated ferret sera were mixed with 100 PFU of wild-type CA04 or Rluc-encoding PB2-KO virus possessing CA04-derived HA and NA vRNAs (CA04/PB2-Rluc). After incubation at 37° C. for 1 hour, wild-type AX4 or AX4/PB2 cells were inoculated with the wild-type virus- or PB2-KO virus-serum mixtures, respectively, in triplicate wells and incubated for three days or 24 hours for the wild-type virus or PB2-KO virus, respectively. The neutralization activity of the ferret sera was determined on the basis of the CPE observed under the microscope or the Rluc activity as measured by using the *Renilla* luciferase assay system (Promega) for the wild-type virus or PB2-KO virus, respectively.

Results

Characterization of the PR8/PB2-GFP Virus.

To establish a cell line that stably expresses PB2 protein, AX4 cells, which are human 2,6-sialyltransferase overexpressing Madin-Darby canine kidney (MDCK) cells that allow better replication of clinical influenza isolates compared with wild-type MDCK cells (Hatakeyama et al., 2005) were transduced, with a retroviral vector that possessed the cDNA of the A/Puerto Rico/8/34 (H1N1, PR8) PB2 protein followed by an internal ribosome entry site sequence derived from the encephalomyocarditis virus and the blasticidin resistance gene. A blasticidin-resistant cell clone was designated as AX4/PB2. To confirm the expression of mRNA for the PB2 protein in AX4/PB2 cells, total RNAs were extracted from AX4/PB2 and wild-type AX4 cells and subjected to RT-PCR with PB2-specific primers. PB2 mRNA was detected in AX4/

PB2 cells but not in wild-type AX4 cells (FIG. 3B). To further validate the expression of the PB2 protein in AX4/PB2 cells, immunofluorescence staining of AX4/PB2 cells was performed by using a PB2-specific monoclonal antibody. Fluorescent signals were detected in AX4/PB2 cells and in some of the PB2 protein expression plasmid-transfected AX4 cells (which served as a positive control), whereas no signal was detected in wild-type AX4 cells (FIG. 3C). These results indicate that AX4/PB2 cells stably express the PB2 protein.

To investigate whether PB2-expressing cells support PB2-KO virus replication, a PR8-based PB2-KO virus possessing PB2(120)GFP(120) vRNA (FIG. 3A), designated as PR8/PB2-GFP (Table 1), was generated by and used to infect AX4/PB2 and wild-type AX4 cells (FIG. 3D). Although no infectious virus was detected in wild-type AX4 cells, replication of PR8/PB2-GFP virus in AX4/PB2 cells was comparable to that of wild-type PR8 (FIG. 3D). These results indicate that the replication of PB2-KO virus is restricted to PB2-expressing cells.

TABLE 1

|  | Origin of: | | | |
| --- | --- | --- | --- | --- |
| Virus | HA gene | NA gene | PB2 gene | Remaining genes |
| Wild-type PR8 | PR8* | PR8 | PR8 | |
| PR8/PB2-GFP | PR8 | PR8 | PB2(120)GFP(120)‖ | |
| PR8ΔPB2 | PR8 | PR8 | –¶ | |
| WSN/PB2-GFP | WSN† | WSN | PB2(120)GFP(120) | |
| CA04/PB2-GFP | CA04‡ | CA04 | PB2(120)GFP(120) | PR8 |
| VN1203/PB2-GFP | VN1203§ | VN1203 | PB2(120)GFP(120) | |
| PR8/PB2-Rluc | PR8 | PR8 | PB2(120)Rluc(120)‖ | |
| PR8/PB2-Fluc | PR8 | PR8 | PB2(120)Fluc(120)‖ | |
| CA04/PB2-Rluc | CA04 | CA04 | PB2(120)Rluc(120) | |

*PR8, A/Puerto Rico/8/34 (H1N1).
†WSN, A/WSN/33 (H1N1).
‡CA04, A/California/04/09 (H1N1).
§VN1203, A/Vietnam/1203/04 (H5N1). The multiple basic amino acid residues in the HA cleavage site (RERRRKKR↓G) were replaced with a non-virulent type cleavage sequence (RETR↓G).
‖PB2(120)GFP(120), PB2(120)Rluc(120), and PB2(120)Fluc(120). GFP, firefly luciferase, and Renilla luciferase genes, respectively, flanked by the 3' and 5' non-coding sequences and 120 bases of the 3' and 5' coding sequences of the PB2 gene.
¶-, not applicable.

The stability of the reporter gene in PB2-KO virus was ascertained by serial passaging of PR8/PB2-GFP virus in AX4/PB2 cells. GFP-expressing plaques versus total plaques formed were calculated to determine the percentage of plaque-forming viruses expressing the GFP reporter gene (Table 2); after five serial passages, 80%-90% of the plaque-forming viruses expressed GFP. PB2-KO virus failed to form plaques in wild-type cells even after five serial passages in AX4/PB2 cells, indicating that reversion of PB2-KO virus to a replication-competent genotype by recombination between the PB2-GFP vRNA and the cell-expressed PB2 mRNA is unlikely. An attempt was made to rescue a PB2 gene-deficient virus possessing seven vRNA segments (PR8ΔPB2, Table 1); however, neither cytopathic effect (CPE) nor NP protein expression were observed in AX4/PB2 or wild-type AX4 cells inoculated with the transfectant supernatant for PR8ΔPB2 (data not shown). These results highlight the importance of the PB2 vRNA for efficient generation of infectious virions (Muramoto et al., 2006).

TABLE 2

Genetic stability of PB2-KO virus.

| | Ratio of GFP-positive plaques* from viruses in: | | | | |
| --- | --- | --- | --- | --- | --- |
| | Passage 1 | Passage 2 | Passage 3 | Passage 4 | Passage 5 |
| Exp. 1 | 100% | 90% | 90% | 100% | 80% |
| Exp. 2 | 100% | 100% | 90% | 100% | 90% |
| Exp. 3 | 100% | 90% | 90% | 100% | 90% |

*The respective viral supernatants were subjected to standard virus plaque assays in confluent AX4/PB2 cells. Ten plaques were marked per well, which were then subjected to the immunodetection assay by using an anti-GFP antibody to detect GFP-expressing viral plaques. The percentage of plaques that stained brown among all plaques is presented. The results of three independent experiments (Exp.) are shown.

Functional Expression of Different HA and NA Genes in PB2-KO Virus.

Figure 4:
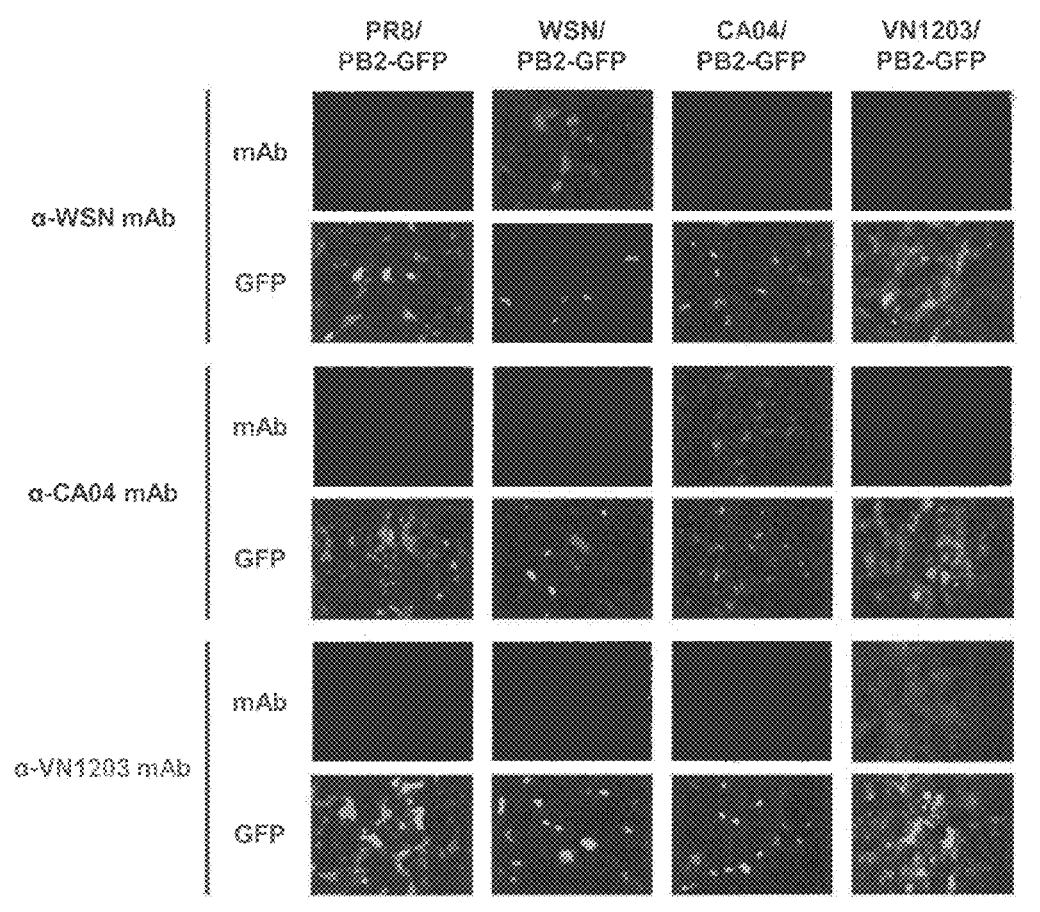

Two surface glycoproteins on influenza A virions, hemagglutinin (HA) and neuraminidase (NA), are the main protective antigens (Wright et al., 2007). In particular, HA mediates cell attachment; therefore, an antibody against HA is crucial for virus neutralization. It was tested whether the relevant glycoproteins of a PR8 virus-based PB2-KO virus could be replaced with those of other virus strains. To this end, GFP-encoding PB2-KO viruses were generated by substituting PR8HA and NA vRNAs with those derived from a laboratory H1N1 strain A/WSN/33 (WSN/PB2-GFP), a 2009 pandemic (H1N1) strain A/California/04/2009 (CA04/PB2-GFP), or a highly pathogenic H5N1 strain A/Vietnam/1203/2004 (VN1203/PB2-GFP) (Table 1). AX4/PB2 cells were infected with these viruses and subjected to an immunofluorescence assay with various anti-HA monoclonal antibodies. In the GFP-positive virus-infected cells, virus strain-specific HA expression was detected (FIG. 4). It was confirmed by sequencing that the corresponding NA vRNAs were incorporated into virions (data not shown). These results indicate that the HA and NA genes of other influenza viruses can also be accommodated in the PB2-KO virus and hence be expressed in virus-infected cells.

Expression of Alternative Reporter Genes in PB2-KO Virus.

The activity of the luciferase reporter gene is readily quantifiable and, therefore, its incorporation into PB2-KO virus should allow one to measure virus replication based on luciferase activity. To test this possibility, PB2-KO viruses were generated that possessed either the firefly (PR8/PB2-Fluc) or Renilla (PR8/PB2-Rluc) luciferase gene in the PB2 vRNA (Table 1). AX4/PB2 and wild-type AX4 cells were infected with these viruses at various multiplicities of infection (MOIs) and subjected to a luciferase assay at 8 hours post-infection. In virus-infected AX4/PB2 cells, Fluc and Rluc activities were detected in a dose-dependent manner; viruses infected at an MOI of 0.1 and 0.001 were adequate for detecting significant Fluc and Rluc activities, respectively (FIG. 5A). By contrast, to detect significant GFP intensity in virus-infected cells, we needed to infect PR8/PB2-GFP at an MOI of 1 or higher (FIG. 5B). These results indicate that the Fluc and Rluc genes can be accommodated in PB2-KO virus and represent a more quantitative indicator for virus replication than does the GFP gene. Wild-type AX4 cells infected with PR8/PB2-Fluc and PR8/PB2-Rluc also exhibited detectable Fluc and Rluc activities, respectively, at an MOI of more than 1 for PR8/PB2-Fluc or 0.01 for PR8/PB2-Rluc, although the activity of both reporter genes was more than 10-fold lower than that detected in AX4/PB2 cells (FIG. 5A). Since the PB2 protein was not provided in trans to the wild-type AX4 cells, the expression of these reporter genes suggests that viral ribonucleoproteins (i.e., PB2, PB1, PA, and NP)

derived from incoming viruses mediate the transcription of the PB2 vRNA of PB2-KO virus at a significantly high level in wild-type AX4 cells.

PB2-KO Virus-Based Microneutralization.

Figure 6:
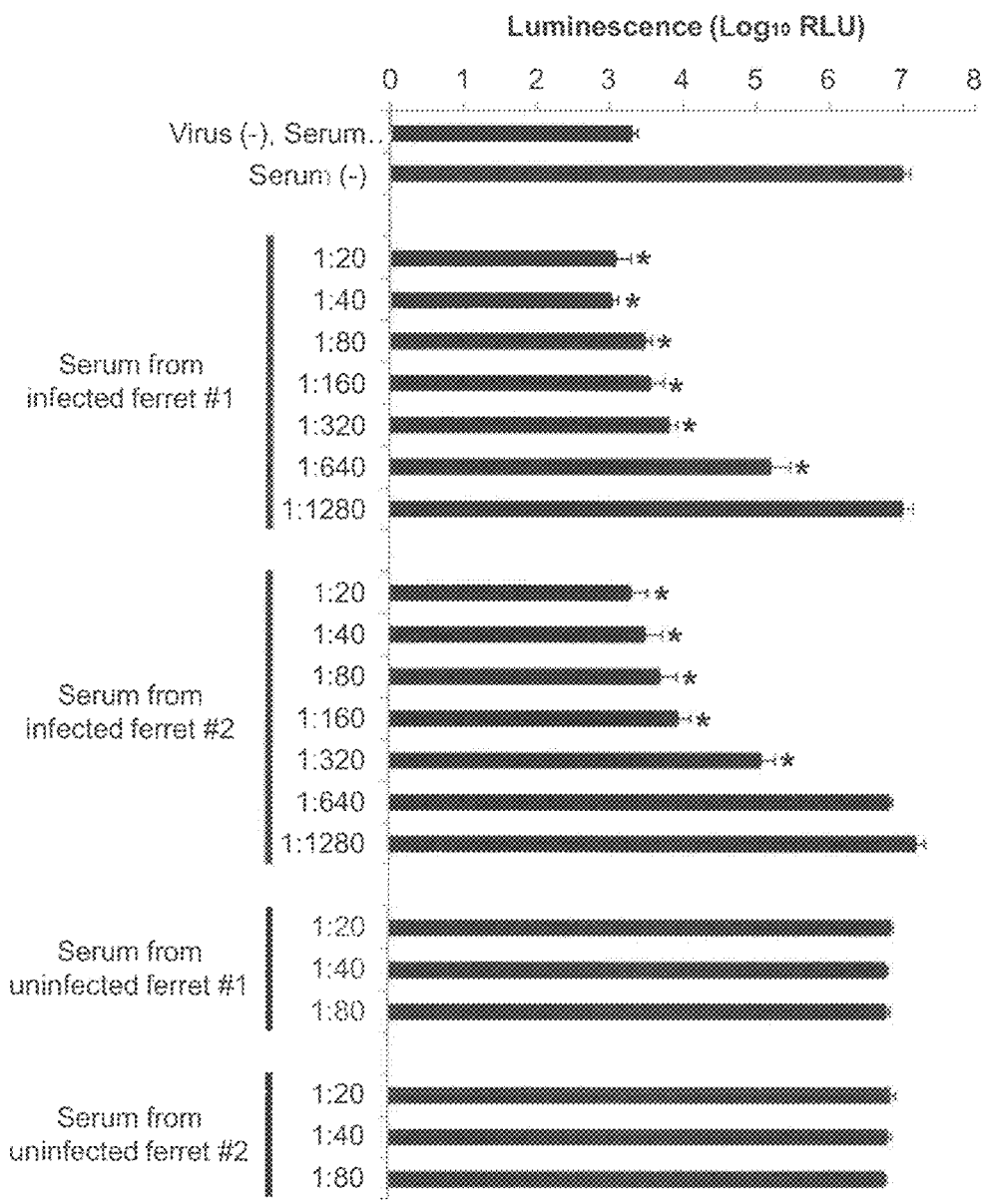
FIG. 6. PB2-KO virus-based microneutralization assay. AX4/PB2 cells were infected with 100 PFU of CA04/PB2-Rluc that were pre-mixed with serially diluted ferret sera in triplicate wells. Rluc activity in cells was measured by using a *Renilla* luciferase assay system at 24 hours post-infection. Results from virus-infected cells were compared with those from cells that were infected with serum-untreated virus (indicated by 'Serum (−)'). P values were calculated by using the Student's t test. Asterisk, P<0.05. RLU, relative light unit.

Biologically contained, reporter gene-expressing influenza viruses have the potential to supersede conventional virus replication evaluation systems in part because of the ability to quantitate growth via platereader assays. The neutralization activity of antisera is typically determined by using conventional microneutralization assays (Itoh et al., 2009; Kobasa et al., 2004), which allow the detection of neutralizing antibodies based on the presence or absence of virus infection-induced CPE or of virus antigens, as detected by using an enzyme-linked immunosorbent assay. To use PB2-KO virus to detect neutralizing antibodies against 2009 pandemic viruses, a PB2-KO virus was generated that possessed the Rluc gene-encoding PB2 vRNA and A/California/04/2009-derived HA and NA vRNAs (CA04/PB2-Rluc). CA04/PB2-Rluc (100 PFU) was mixed with serially diluted antisera collected from CA04-infected ferrets and incubated at 37° C. for 1 hour. Sera from uninfected ferrets served as negative control. The virus-sera mixtures were used to inoculate AX4/PB2 cells. At 24 hours post-infection, Rluc activity in cells was measured by using the *Renilla* luciferase assay system (Promega). To compare the detection sensitivity, the same antisera were also tested for neutralization activity by using a CPE-based conventional microneutralization assay with wild-type CA04 and wild-type AX4 cells. In the PB2-KO virus-based assay, 1:1280- and 1:640-diluted ferret sera induced a significant decrease in Rluc activity in virus-infected cells (FIG. 6). By contrast, the neutralizing titers of the same ferret sera as determined in the conventional microneutralization assay were 160 and 80 (data not shown). These results indicate that the PB2-KO virus coupled with PB2-expressing cells offer a neutralizing antibody detection method that is more sensitive than the conventional microneutralization assay.

Discussion

Figure 5:
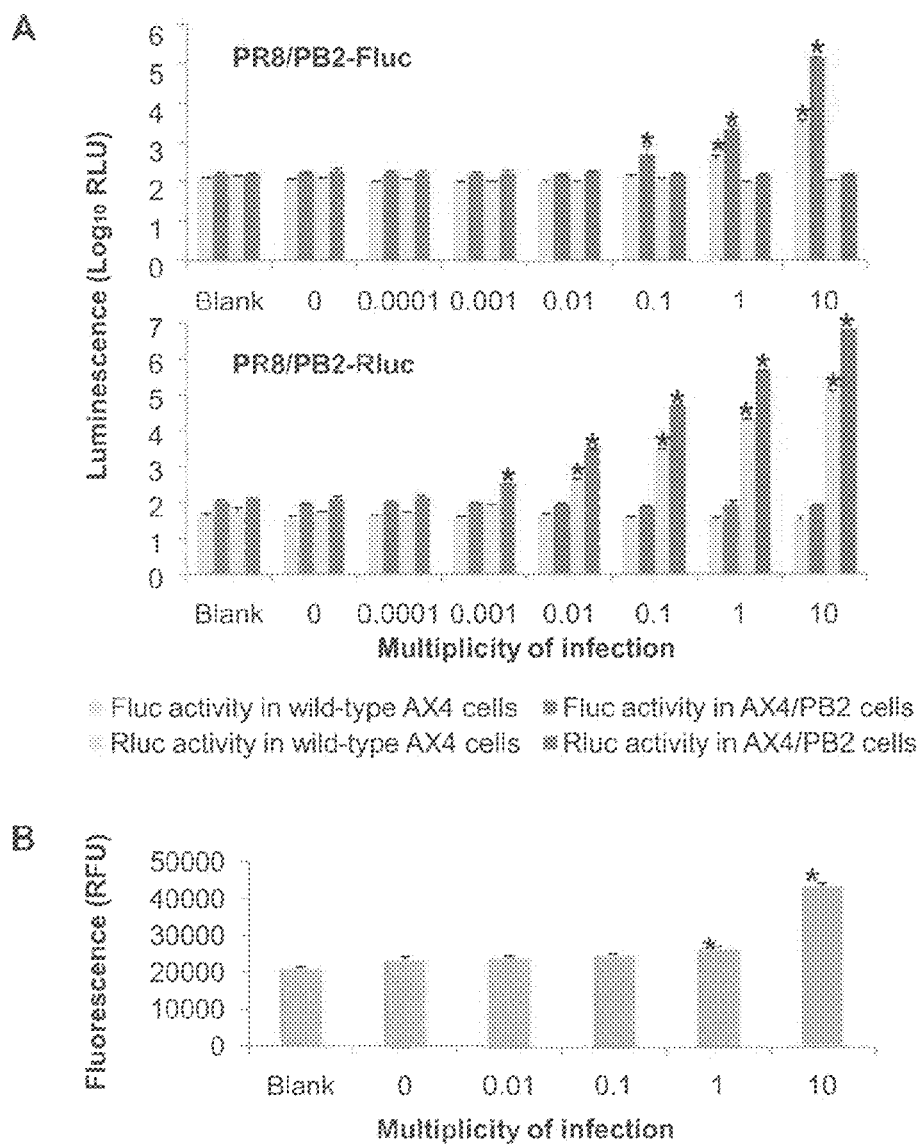
FIG. 5. Accommodation of various reporter genes in PB2-456 KO virus. A) Luciferase activity in PB2-KO virus-infected cells. Wild-type AX4 and AX4/PB2 cells were infected with PR8/PB2-Fluc (upper graph) and PR8/PB2-Rluc (lower graph) at the indicated MOIs. At 8 hours post-infection, Fluc and Rluc activities in cells were measured by using a dual-luciferase reporter assay system. Results from virus-infected cells were compared with those from uninfected cells (indicated by '0') and P values were calculated by using the Student's t test. Asterisk, P<0.05. RLU, relative light unit. B) GFP intensity in PB2-KO virus-infected cells. AX4/PB2 cells were infected with PR8/PB2-GFP at the indicated MOI. At 8 hours post-infection, GFP intensity was measured with the Infinite M1000 microplate reader. Results from virus-infected cells were compared with those from uninfected cells (indicated by '0') and P values were calculated by using the Student's t test. Asterisk, P<0.05. RFU, relative fluorescent unit.

Here, it is demonstrated that PB2-KO influenza viruses are replication-incompetent in wild-type cells, but undergo multiple replication cycles in PB2 protein-expressing cells (FIG. 3D). In addition, reporter genes flanked by the PB2 vRNA packaging signals were stably maintained in progeny viruses (Table 1) and expressed in virus-infected cells (FIGS. 4 and 5). It was also confirmed that different virus strain-derived HA and NA genes were accommodated by PB2-KO viruses (FIG. 4). These results indicate that PB2-KO viruses have broad potential use throughout the field of influenza virology.

As a practical application, a PB2-KO virus-based microneutralization assay was developed and used to detect neutralizing antibodies against the 2009 pandemic virus (FIG. 6). This PB2-KO virus-based assay proved to be more sensitive than the conventional microneutralization assay in terms of neutralizing antibody detection. The use of replication-incompetent PB2-KO viruses as a screening platform (FIGS. 3C and 3D) may enable the detection of neutralizing antibodies against highly pathogenic viruses such as H5N1 and 1918 strains, which normally must be handled in BSL3 facilities and under biosafety level 2 containment, although an additional layer of biosafety (e.g., modification of the amino acid sequence of the HA cleavage site) would be required. Kong et al. (2006) previously developed a neutralizing antibody screening system based on influenza HA-pseudotyped lentiviruses, which also allows the detection of neutralizing antibodies against the bio safety level 3 agents. However, these lentiviruses do not express influenza viral neuraminidase, which, along with HA, has the potential to induce neutralizing antibodies (Nayak et al., 2010); therefore, the PB2-KO virus-based assay should more accurately reflect the neutralizing antibody titers. Although cells that stably express reporter gene-encoding influenza vRNA have also been shown to allow the sensitive detection of neutralizing antibodies (Hossain et al., 2010; Li et al., 2009), infectious viruses are required for these recombinant cell-based assays.

Another potential application of the PB2-KO virus is its use as a novel influenza vaccine, which we believe is feasible for the following reasons. First, PB2-KO virus generates high titers (>$10^8$ PFU/mL) in the AX4/PB2 cell line (FIG. 3D); second, the fact that HA and NA proteins can be expressed (FIG. 4) demonstrates that PB2-KO virus is customizable to encode desired antigens; third, the vRNA transcription that occurs in PB2-KO virus-infected cells (FIG. 5A) may stimulate cellular innate immunity by producing double-stranded RNA; and fourth, the stable maintenance of a foreign gene inserted in the PB2 vRNA (Table 2) could serve as a carrier of an additional antigen, enabling the engineering of PB2-KO as a safe multi-valent vaccine.

To date, several recombinant influenza viruses that lack a particular viral protein have been shown to replicate comparably to wild-type virus in cell culture when the missing protein is provided in trans. M2-lacking influenza virus efficiently replicates in M2-expressing cells and has demonstrated potential as a live attenuated vaccine (Watanabe et al., 2009). A distinct advantage of the PB2-KO virus over its M2 counterpart is that the former is replication-incompetent in normal cells and, thus, safer. Further, it remains unknown whether a foreign gene encoded in the M2 protein-coding region can be incorporated into progeny viruses and expressed in virus-infected cells.

Martínez-Sobrido et al. (2010) developed an improved screening assay for the rapid detection of neutralizing antibodies by using influenza virus possessing the GFP gene flanked by the HA vRNA packaging signals. Although this HA-KO virus underwent multiple replication cycles only in cells that expressed the HA protein, the stability of reporter genes in this HA-KO virus was not tested in the study. In fact, an HA vRNA-deficient virus possessing seven vRNA segments underwent multiple rounds of replication in HA-expressing MDCK cells (data not shown) in contrast to the PB2 vRNA-deficient PR8ΔPB2 virus (see above), suggesting that the reporter gene-encoding HA vRNA in HA-KO virus could be easily dropped during replication in HA-expressing cells. A replication-competent virus that possesses the GFP gene in its NA vRNA has also been used to detect neutralizing antibodies (Rimmelzwaan et al., 2011). An in trans bacterial sialidase improved the restricted replication of this NA-KO virus and allowed reasonable virus titer recovery; however, the reporter gene stability of the NA-KO virus remains uncertain.

More recently, GFP gene-possessing replication-competent influenza viruses have been generated by using recombinant NS (Manicassamy et al., 2010) or NA (Li et al., 2010) genes. Although these viruses have potential as research tools, their replicability raises biosafety issues, which are not a concern with the PB2-KO virus. Overall, the fact that the PB2-KO virus produced in this study stably expresses a foreign gene and is replication-incompetent makes it ideal in terms of reliability and bio safety.

In conclusion, a biologically contained foreign gene-expressing influenza virus was generated by replacing the viral PB2 gene with reporter genes. The replication of the virus was restricted to cells that expressed the PB2 protein in trans. The reporter gene was stably inherited in progeny viruses during replication in PB2-expressing cells. Various HA, NA, and reporter genes were accommodated in the PB2-KO virus. This virus, therefore, shows promise in terms of its numerous applications for basic and applied studies of influenza virus.

Example III

The PB2 protein of influenza viruses is an essential component of the trimeric viral RNA-dependent RNA polymerase subunit. PB2 is implicated in the regulation of host antiviral immune pathways and hence virulence and plays a major role in the incorporation of other individual vRNA segments (Muramoto et al., 2006). Example II describes a PB2-knock-out (PB2-KO) influenza virus that harbors reporter genes, such as the green fluorescent protein (GFP) in the coding region of its PB2 viral RNA (vRNA). The replication of the PB2-KO virus was restricted to only a cell line stably expressing the PB2 protein, yielding a high titre of >$10^8$ PFU/mL. Moreover, during replication PB2 vRNA encoding the reporter gene was stably incorporated into progeny virions and retained through sequential passages. Also, HA and NA vRNA of any influenza virus could be accommodated in the PB2-KO virus and be expressed in virus-infected cells. Therefore, the PB2-KO virus can be tailored to encode desired combinations of HA and NA that are the main influenza antigens, suggesting that the PB2-KO virus can be used as a multivalent vaccine platform. Here, we tested the vaccine potential of the PB2-KO virus by immunizing mice, examining antibody response and protective efficacy in mice.

Materials and Methods

Cells.

293 and 293T (a derivative of the 293 line into which the gene for simian virus 40 T antigen was inserted (DuBridge et al., 1987) human embryonic kidney cells were maintained in Dulbecco's modified Eagle medium (Lonza, Basel, Switzerland) supplemented with 10% fetal calf serum (Invitrogen, Carlsbad, Calif.). Madin-Darby canine kidney (MDCK) cells were maintained in minimum essential medium (MEM) (Invitrogen) supplemented with 5% newborn calf serum (NCS) (Sigma, St. Louis, Mo.). AX4 cells, which are an MDCK-derived cell line with enhanced expression of human-type receptors for influenza virus and were produced by stable transfection of a plasmid expressing the human α-2,6-sialyltransferase (Hatakeyama et al., 2005), were maintained in 5% NCS-MEM supplemented with puromycin (2 µg/mL). AX4/PB2 cells (AX4 cells stably expressing the PB2 protein derived from A/Puerto Rico/8/34 [H1N1, PR8], established by transduction with a retroviral vector (Ozawa et al., 2011) were maintained in 5% NCS-MEM supplemented with puromycin (2 µg/mL) and blasticidin (10 µg/mL). All cells were maintained in a humidified incubator at 37° C. in 5% $CO_2$.

Plasmid-Driven Reverse Genetics.

The wild-type PR8 and PB2-KO viruses used in this study were engineered by using reverse genetics, as previously described (Neumann et al., 1999). For expression of viral RNA (vRNA), plasmids contained the cloned cDNAs of PR8 genes between the human RNA polymerase I promoter and the mouse RNA polymerase I terminator (referred to as PolI plasmids). A plasmid [pPolIPB2(120)GFP(120)] was constructed to replace the PolI plasmid encoding the PB2 segment and contained the A/WSN/33(H1N1)-derived 3' PB2 noncoding region, 120 nucleotides that correspond to the PB2-coding sequence at the 3' end of the vRNA followed by the GFP-coding sequence, 120 nucleotides that correspond to the PB2-coding sequence at the 5' end of the vRNA, and finally the 5' PB2 noncoding region (Muramoto et al., 2006). To generate the PB2-KO virus, pPolIPB2(120)GFP(120) and the remaining 7 PolI plasmids were cotransfected into 293T cells along with eukaryotic protein expression plasmids for PB2, PB1, PA, and NP derived from A/WSN/33 by use of the TransIT 293 transfection reagent (Mirus, Madison, Wis.), following the manufacturer's instructions. At 48 hours post-transfection, the supernatants containing the PR8 or PB2-KO virus were harvested and inoculated into 10-day-old embryonated chicken eggs or AX4/PB2 cells, respectively. Both viruses were titrated by use of plaque assay with AX4/PB2 cells.

Preparation of Formalin-Inactivated Virus.

Egg-propagated PR8 viruses were concentrated and purified by ultracentrifugation of the infected allantoic fluid through a 10% to 50% sucrose density gradient and resuspended in phosphate-buffered saline (PBS). Formalin (final concentration, 0.1%) was added to inactivate the purified PR8 virus at 4° C. for 1 week. Inactivation of the virus was confirmed by passaging viruses twice in MDCK cells and examining the cytopathic effect or lack thereof.

Experimental Infection of Mice with PB2-KO Virus.

To test the safety of the PB2-KO virus in mice, six 4-week-old female BALB/c mice were intranasally inoculated with $10^6$ PFU/mouse of the virus. The body weight and survival of the infected mice were monitored daily for 14 days postinoculation. Also, on days 1, 3, and 6 postinoculation, lungs and nasal turbinates from the inoculated mice were harvested, homogenized, and subjected to plaque assays to detect the presence of virus.

Immunization and Protection Test.

Eight-, six-, or four-week-old female BALB/c mice (3 mice per group) were anesthetized with isoflurane and intranasally inoculated with 50 µl of medium (MEM-containing 0.3% bovine serum albumin fraction V), formalin-inactivated PR8 (64 hemagglutination units, which is equivalent to $10^6$ PFU of the PB2-KO virus), or PB2-KO virus ($10^6$ PFU) once, twice, or three times at 2-week intervals, respectively. Three weeks after the final inoculation, mice were intranasally challenged with 0.5 or 5 50% mouse lethal doses ($MLD_{50}$) of PR8 virus. On days 3 and 6 postinfection, lungs and nasal turbinates of mice (3 mice per group) were collected, homogenized in 1 ml of PBS by using TissueLyser II (Qiagen, Valencia, Calif.), and clarified by low-speed centrifugation (5,000 rpm for 10 minutes at 4° C.). Virus titers in homogenates were determined by using plaque assays with AX4/PB2 cells. The body weight and survival of the remaining challenged mice (3 mice per group) were monitored daily for 14 days.

Detection of Virus-Specific Antibodies.

Sera from mice (3 mice per group) were obtained via mandibular vein bleeding prior to each immunization and via the femoral artery 1 day before challenge. Nasal wash and bronchoalveolar lavage (BAL) fluid samples (3 mice per group) were also obtained 1 day before challenge from mice sacrificed by cervical dislocation. Incisions were made to insert a cannula into the trachea. The lungs were then perfused with 1 ml of PBS by using a syringe. The lavage fluid was recovered and stored in microtubes on ice. Nasal wash was collected by passing 400 µl of PBS through the nasal cavity. IgG and IgA antibodies in the sera, nasal washes, and BAL fluid samples were detected by using an enzyme-linked immunosorbent assay (ELISA) as previously described (Kida et al., 1982). Each well was coated with purified PR8 disrupted with 0.05 M Tris-HCl (pH 7.8) containing 0.5% Triton X-100 and 0.6 M KCl. After incubation of the virus-coated plates with the test samples, IgA and IgG antibodies in the samples were detected by use of goat anti-mouse IgA or IgG antibodies conjugated to horseradish peroxidase (Kirkegaard & Perry Laboratories, Inc., Gaithersburg, Md.). Neutralizing antibody titers in sera of immunized mice were also evaluated as previously described (Iwatsuki-Horimoto et al., 2011). Briefly, virus (100 50% tissue culture infectious doses [$TCID_{50}$]) was incubated with 2-fold serial dilutions of receptor-destroying enzyme-treated sera for 30 minutes at 33° C., and the mixtures were added to confluent MDCKcells on 96-well microplates to determine the neutralizing activity.

IFA for Detection of Antibodies Against GFP.

293 cells grown in 35-mm glass-bottom dishes (Asahi Techno Glass) were transfected with a plasmid expressing GFP and incubated for 48 hours prior to the immunofluorescence assay (IFA). Cells were fixed in PBS containing 4% paraformaldehyde (Wako Pure Chemical Industries Ltd.) for 15 min and permeabilized with 0.1% Triton X-100 for 5 minutes. They were incubated for 1 hour with 20-fold-diluted serum collected from mice mock immunized with medium or immunized with formalin-inactivated PR8 or with the PB2-KO virus. Anti-GFP antibody (clone GFP-20; Sigma-Aldrich)-treated cells served as a positive control. All cells were then further incubated for 1 hour with an Alexa Fluor 594-labeled goat anti-mouse secondary antibody (Invitrogen) and Hoechst 33342 (Invitrogen) for the detection of GFP antibody and nuclear staining, respectively. Samples were observed under a confocal laser microscope (LSM510META; Carl Zeiss, Jena, Germany).

Results

Characterization of the PB2-KOvirus in Mice.

The PB2-KO virus was replication incompetent in AX4 cells but yielded high titers similar to those of PR8 in AX4/PB2 cells. To determine whether the PB2-KO virus could serve as an influenza vaccine, its safety profile was assessed in mice by intranasally inoculating each mouse with the PB2-KO virus ($10^6$ PFU in 50 µL) and monitoring body weight for 2 weeks. Mice steadily achieved stable growth increments and appeared unperturbed by PB2-KO virus infection (data not shown). Lungs and nasal turbinates obtained on days 1, 3, and 6 postinoculation were homogenized and subjected to plaque assays in AX4/PB2 cells to assess the growth of the PB2-KO virus in mice. No plaques were detected from organs of mice infected with the PB2-KO virus, whereas a high virus titer ($10^8$ PFU/g) was found in lung tissue of mice infected with $10^6$ PFU of PR8 virus. These results indicate that the PB2-KO virus did not grow in mice and that reversion to a replication-competent virus did not occur.

Virus-Specific Antibody Responses in Mice Inoculated with the PB2-KO Virus.

Figure 8:
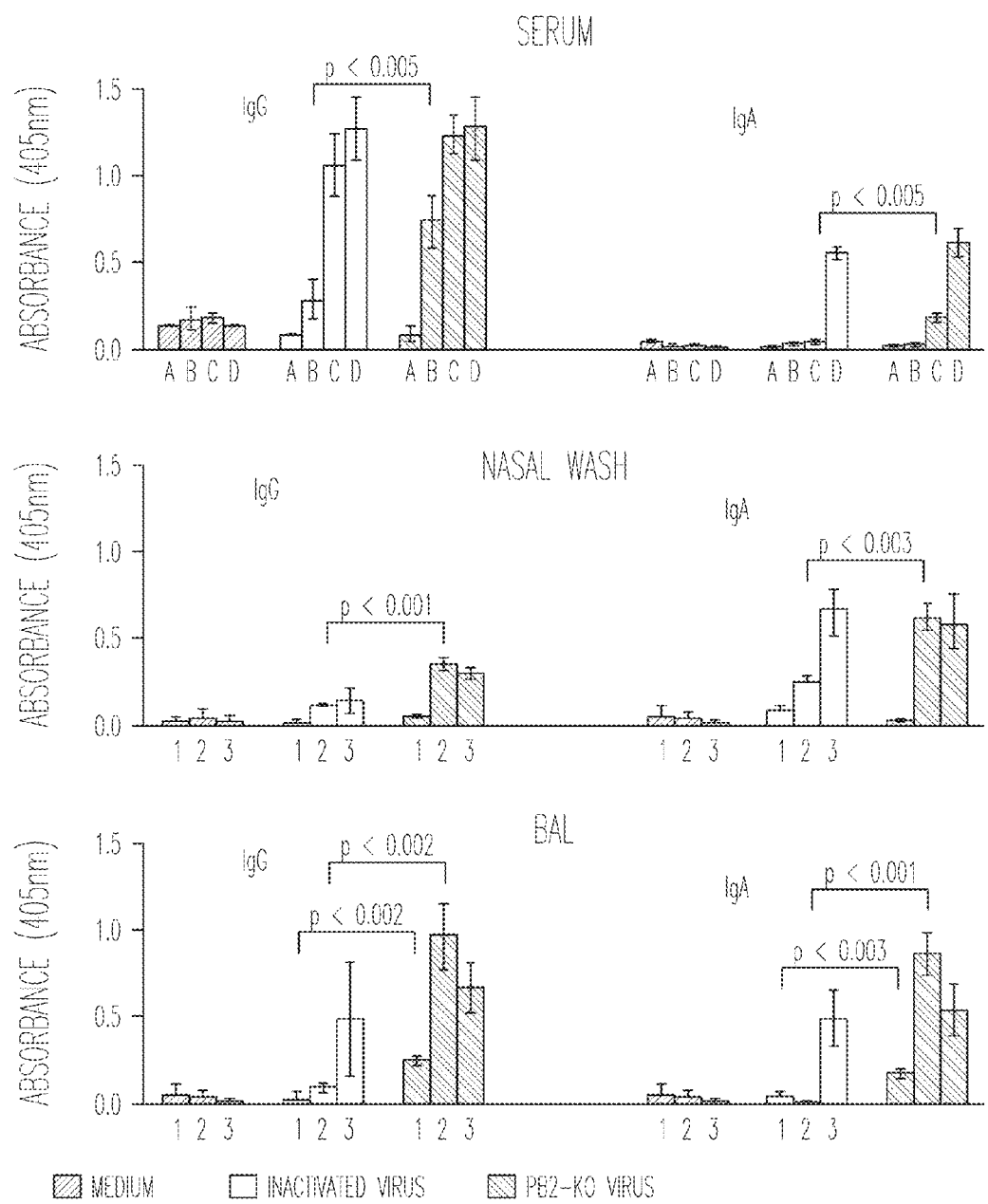
FIG. 8. Virus-specific antibody responses in immunized mice. Purified PR8 virus was used as an antigen to analyze IgG and IgA antibody titers in the sera, nasal washes, and BAL fluids (top, middle, and bottom, respectively) of mice mock immunized with medium or immunized with the formalin-inactivated virus or with the PB2-KO virus. Sera (top panels) were obtained at different time points, i.e., prevaccination (bars A), before the second vaccination (bars B), before the third vaccination (bars C), and before challenge (bars D). Nasal washes and BAL fluids (middle and bottom panels, respectively) were obtained 1 day before challenge from mice given 1 vaccination (bars 1), 2 vaccinations (bars 2), or 3 vaccinations (bars 3). Values are expressed as the mean absorbance ±standard deviation (SD) (n=3). Statistical significance between samples obtained from mice immunized with inactivated virus and PB2-KO virus is indicated.

The level of antibody responses elicited by the PB2-KO virus was examined in mice that were intranasally inoculated with the PB2-KO virus once, twice, or three times at 2-week intervals. For comparison, mice were also mock immunized with medium or immunized with formalin-inactivated PR8 virus at a dose equivalent to $10^6$ PFU of the PB2-KO virus. Sera were collected at various time points to determine the presence of different levels of antibodies over time. Also, at 3 weeks after the final inoculation, the levels of IgG and IgA antibodies against PR8 in the sera, nasal washes, and BAL fluid samples were examined by using an ELISA (FIG. 8). Neither the IgG nor the IgA response in any sample was appreciable in mice inoculated with medium. In contrast, mice immunized with the formalin-inactivated PR8 and PB2-KO viruses exhibited a time-dependent increase in serum IgG and IgA levels. After three immunizations, similar antibody levels were detected in both inactivated virus- and PB2-KO virus-immunized mice. Interestingly, when mice were immunized once or twice, significantly higher serum IgG or IgA titers, respectively, were observed in PB2-KO virus-immunized mice than in mice immunized with the formalin-inactivated virus (FIG. 8, top panel). In nasal washes of mice inoculated with PB2-KO virus twice and in BAL fluids of mice inoculated once and twice, IgG and IgA levels were significantly higher than those in mice inoculated with the formalin-inactivated virus (FIG. 8, middle and bottom panels, respectively). Thus, PB2-KO virus efficiently induced IgG and IgA antibody responses in this murine model. Sera obtained from mice mock immunized with medium had no neutralizing antibodies, whereas those from PB2-KO-treated mice had neutralizing antibody titers of 1:16, which was approximately 2-fold higher than that in mice treated with inactivated virus (data not shown). Neutralizing activities were not detected in any nasal wash sample or BAL fluid (data not shown).

Vaccine Efficacy of the PB2-KO Virus.

To assess the vaccine efficacy of the PB2-KO virus, mice were challenged with 0.5 or 5 $MLD_{50}$ of PR8 virus. The former challenge dose was tested to mimic natural infections, in which individuals are usually infected with a relatively low virus dose (certainly not a lethal dose).

(i) Body Weight Changes and Survival of Immunized Mice after Challenge.

Figure 7:
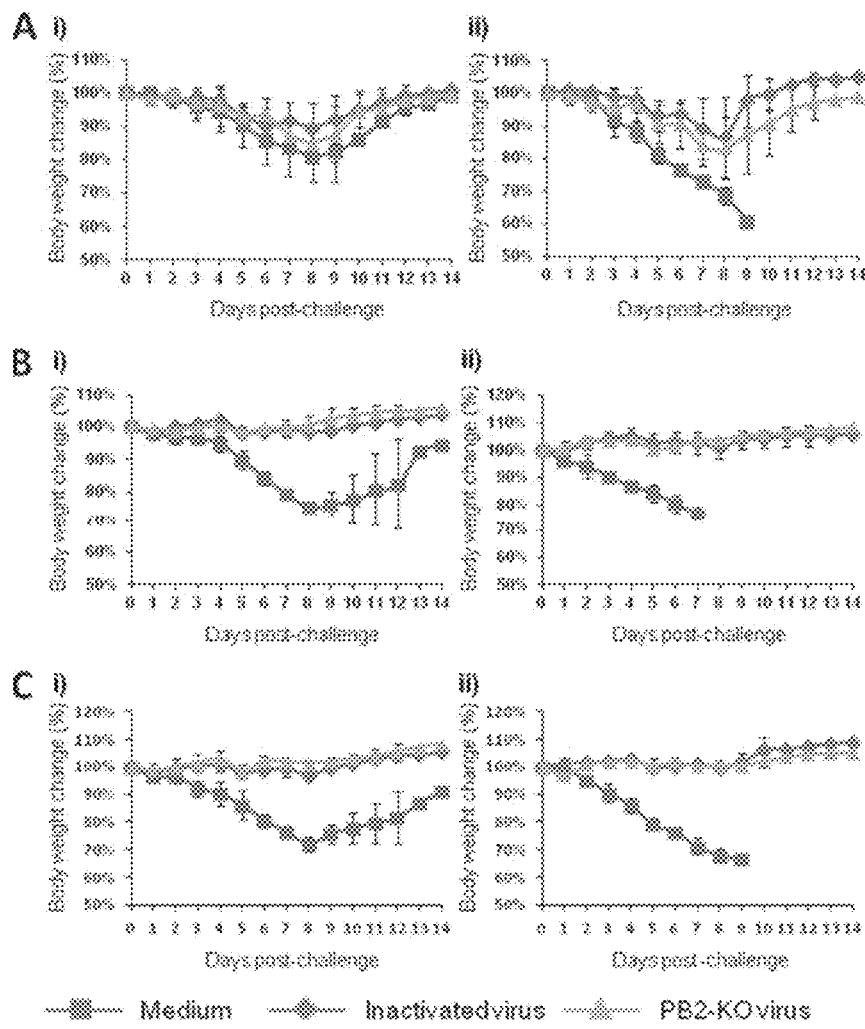
FIG. 7. Body weight change after challenge in mice. Mice immunized with the indicated agents once (A), twice (B), or three times (C) were challenged with 0.5 (i) or 5 (ii) $MLD_{50}$ of PR8 virus. Values are expressed as mean changes in body weight ±SD (n=3).

To assess the vaccine efficacy of the PB2-KO virus, body weight changes and survival of mice immunized with the PB2-KO virus were examined after they were challenged with the PR8 virus. Mice mock immunized with medium and challenged with 0.5 $MLD_{50}$ of PR8 experienced substantial body weight loss, which they subsequently recovered (FIG. 7, left panels). On the other hand, all mice mock immunized with medium and challenged with 5 $MLD_{50}$ of PR8 showed substantial body weight loss and died at approximately 1 week postinfection (FIG. 2A-FIG. 2I, right panels). Mice immunized once with the formalin-inactivated or PB2-KO virus experienced weight loss (15%) after each challenge dose (FIG. 7A). It is noteworthy that 100% of mice immunized once with the PB2-KO virus survived, whereas one out of three mice immunized once with the formalin-inactivated virus died on day 8 postinfection after being challenged with 5 $MLD_{50}$ of the PR8 virus (data not shown). All mice immunized twice and three times with the inactivated and PB2-KO viruses survived without any appreciable body weight loss (FIGS. 7B and C).

(ii) Virus Replication in Lungs and Nasal Turbinates.

Figure 9A:
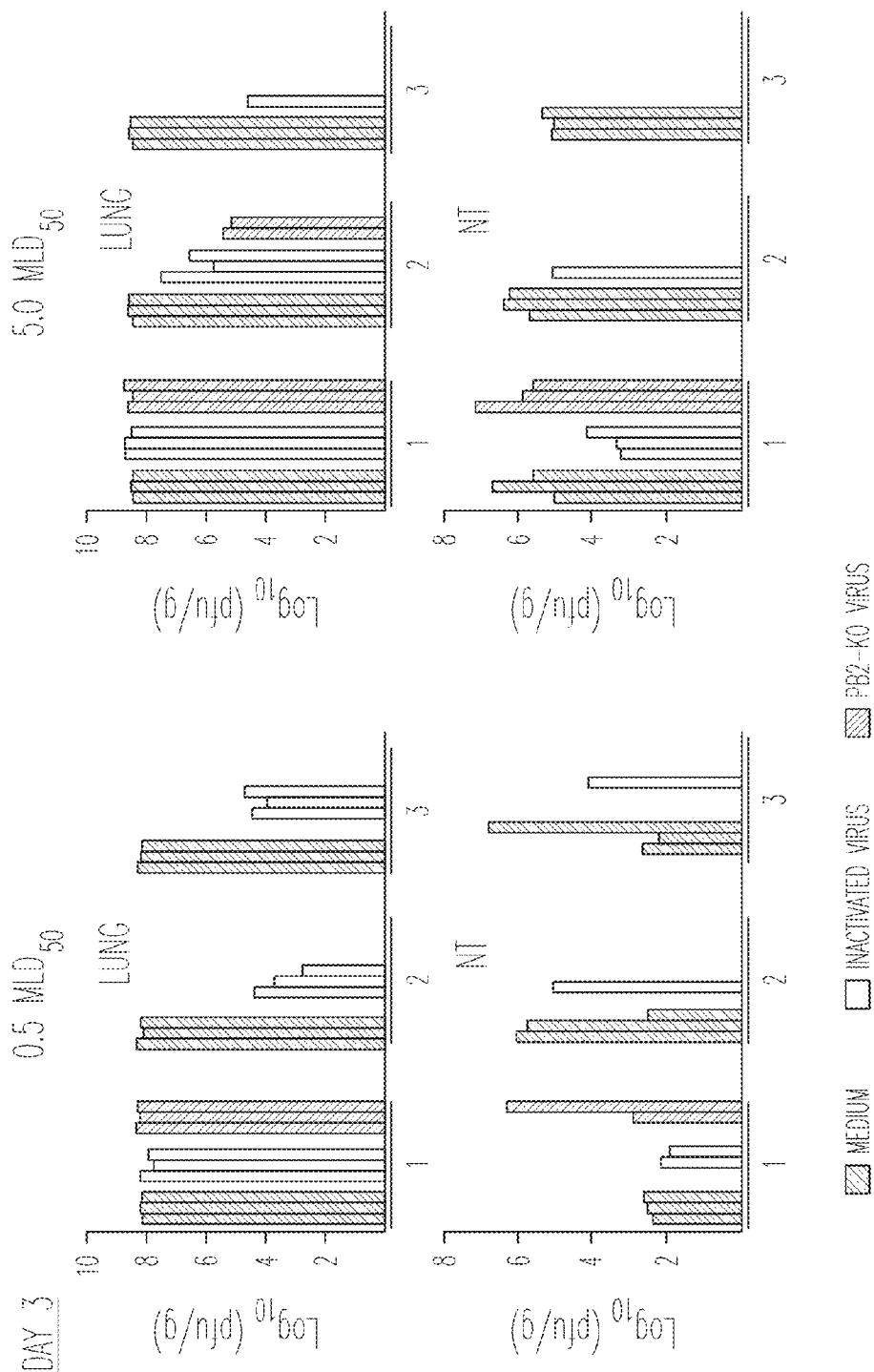
FIGS. 9A and 9B. Virus titers in the lungs and nasal turbinates (NT) of immunized mice after challenge. The numbers on the x axis indicate the number of vaccinations. Three BALB/c mice per group were intranasally infected with the indicated doses of PR8 virus (50 μL per mouse) and sacrificed on days 3 and 6 postinfection for virus titration. Bars indicate the virus titer in each organ of each mouse. The absence of bars indicates that virus titers were below the detection limit of 5 PFU/mL/organ.
Figure 9B:
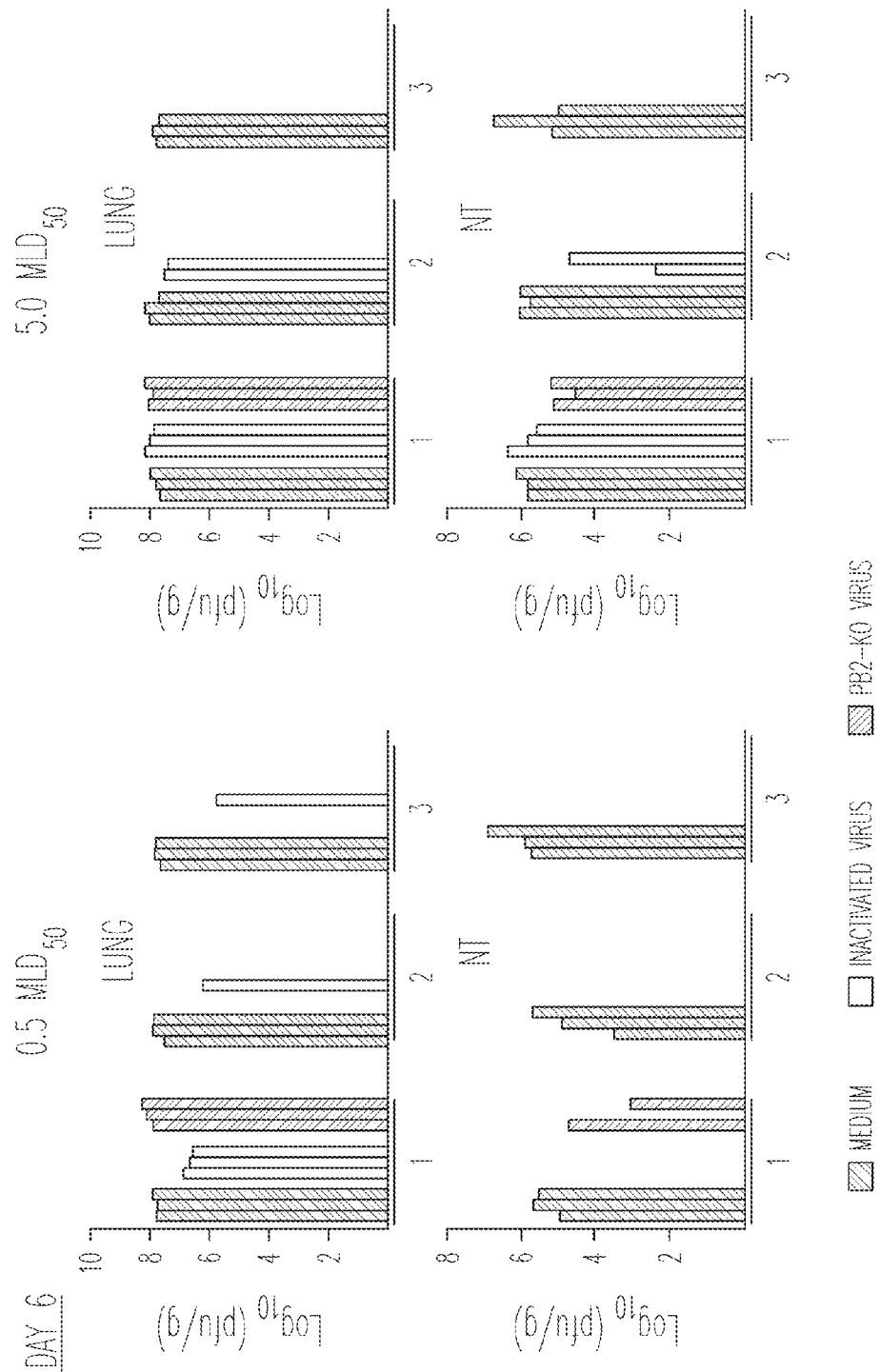

To evaluate virus replication in the lungs and nasal turbinates of mice immunized with the PB2-KO virus, both organs were collected on days 3 and 6 post-challenge with the PR8 virus. FIG. 9 shows the extent of virus replication in these organs. The PR8 virus replicated to a high titer in the lungs and nasal turbinates of all mock-immunized mice. Although the potency of the PB2-KO vaccine was similar to that of the formalin-inactivated vaccine in mice immunized once, in mice that received two or three vaccinations, the PB2-KO vaccine was more efficacious than the formalin-inactivated vaccine, with virus titers in both organs being considerably lower in mice immunized with the former than in those immunized with the latter. Taken together, these results indicate that the PB2-KO virus has better potency as an influenza vaccine than the formalin-inactivated virus.

Detection of Antibodies Against GFP in Mice Inoculated with the PB2-KO Virus.

Finally, it was determined whether the PB2-KO virus could induce antibodies against GFP, because the PB2-KO virus used here possesses the GFP gene in its PB2-coding region and GFP was expressed in PB2-KO virus-infected culture cells (data not shown). The detection of an anti-GFP antibody in the sera of mice inoculated with the PB2-KO virus would suggest the potential for this system as a platform for the development of an influenza virus-based multivalent vaccine. Therefore, sera was collected from mice on day 3 postchallenge and tested them in an IFA. GFP was not detected with sera from mock-immunized mice or from those immunized with the inactivated vaccine (FIG. 10); however, sera from mice immunized with the PB2-KO virus, as well as a commercial anti-GFP antibody (which served as a positive control), detected GFP expression. These results indicate that an antibody against GFP was induced in mice immunized with the PB2-KO virus, suggesting the potential application of the PB2-KO virus as a multivalent vaccine.

Discussion

Here, it was demonstrated that a replication-incompetent PB2-KO virus elicits virus-specific protective antibody responses and that this virus also induces antibodies against the reporter protein encoded in the coding region of its PB2 segment. In particular, the PB2-KO vaccine protected mice from lethal challenge with H1N1 PR8 virus, suggesting the potential of this vaccine against influenza A infection. The ability to detect antibody against GFP in sera of mice inoculated with PB2-KO virus suggested that if the reporter gene, or GFP in this case, were to be replaced with the antigenic region of another pathogen, mice inoculated with the recombinant virus will express antibodies against this secondary pathogen; in turn suggesting its potential as a multivalent vaccine. Therefore, replication-incompetent PB2-KO virus can serve as a platform for an influenza vaccine as well as for a multivalent vaccine if the PB2-coding region is replaced with the antigenic portion of another pathogen.

Inactivated and live-attenuated vaccines including gene knock-out viruses have been reported to successfully immunize mice against lethal influenza infections. The M2-KO virus lacking transmembrane and cytoplasmic tail domains efficiently replicates in M2-expression cells and demonstrates potential as a live attenuated vaccine (Watanabe et al., 2009). The HA-KO was also shown to undergo multiple replication cycles in cells that constitutively express the HA protein (Martinez-Sobrido et al., 2010); however, large quantities of viruses yielding sufficient HA protein in high titers seem to be required for protective efficacy. The stable incorporation and maintenance of the reporter gene has not been studied in the M2-KO or HA-KO systems. Previously, it was demonstrated that replication-incompetent virus-like particles (VLPs) efficiently elicit mucosal and systemic immune responses in a murine model. VLPs that lack NS2 protect mice against various lethal doses of influenza viruses (Watanabe et al., 2002). However, the absence of a cell line that constitutively expresses NS2 precludes the efficient production of sufficient VLPs to elicit protective efficacy.

In contrast to the M2-KO, HA-KO and/or VLPs described above, PB2-KO virus could be prepared in a cell line that expressed PB2, yielded high titers, and stably incorporated and maintained a GFP gene during virus replication (Ozawa et al., 2011). These data clearly establish the feasibility of using this system for efficient vaccine production Safety is of utmost importance when the potential use of viruses as vaccines is concerned. Both live attenuated and most inactivated influenza vaccines are currently propagated in embryonated chicken eggs, although cell-based vaccines have been licensed in Europe. Since a prerequisite for successful egg-based vaccine propagation is the selection of variants adapted to embryonated chicken eggs at the time of implementation, the virus in the vaccine may be slightly different from the circulating viruses in terms of antigenicity (Fulvini et al., 2011; Hardy et al., 1995; Robertson, 1993). Because of the propensity of egg proteins in these vaccines to induce allergies, parenterally administered inactivated vaccines produced in eggs are associated with adverse or anaphylactic reactions in some individuals (Halperin et al., 2002). An added complication is the possible depletion of chicken stocks in the event of an outbreak of a highly pathogenic avian influenza pandemic, which could compromise mass vaccine production (Hampson, 2008).

In contrast, cell-based alternatives offer several advantages over conventional egg-based vaccine propagation. Manufacturing capacity can be readily scaled up in proportion to demand. In addition, unlike for viruses grown in eggs, the antigenicity of viruses grown in cells matches that in animals and humans (Katz et al., 1990; Robertson et al., 1991).

A cell line was established that stably expresses PB2 and PB2-KO virus efficiently replicated in this cell line (i.e., at a level comparable to that for wild-type virus) (Ozawa et al., 2011). In cells that do not express PB2 in trans, replication-incompetent PB2-KO virus only undergoes a single cycle of replication and will not result in the formation of infectious particles; thus PB2-KO virus induces a protective antibody response without allowing the replication of infectious virus. Therefore, a cell-based PB2-KO vaccine eliminates various obstacles to vaccine preparation and delivery.

Furthermore, knocking out the PB2 gene renders the PR8 influenza virus replication incompetent with no evidence of recombination between the recombinant PB2 vRNA and the PB2 protein mRNA even upon multiple replication cycles.

A formalin-inactivated vaccine efficiently protected mice from challenges with lethal doses of the PR8 virus by eliciting immune responses (FIGS. 7-9). However, even though the outcomes in terms of survival and body weight loss were similar for mice immunized with the formalin-inactivated vaccine and those immunized with the PB2-KO vaccine (FIG. 7), the virus titers in the lungs and nasal turbinates of the mice immunized with the former vaccine were higher than in those in mice immunized with the latter (FIG. 9). This finding likely reflects differences in the levels of immune responses (FIG. 8). It is also plausible that cytotoxic T lymphocyte (CTL) responses were activated by the PB2-KO virus but not by the formalin-inactivated virus, since inactivated antigens are thought not to induce CTL responses, although CTL responses were not examined in this study.

By definition, a multi-valent or poly-valent vaccine refers to a vaccine designed to elicit an immune response to more than one infectious agent or to several different antigenic determinants of a single agent. Based on the fact that other reporter genes and the HA and NA genes of different virus strains can be accommodated by the PB2-KO virus, the design and manufacturing of a multi-valent vaccine is made feasible. As a result, it is conceivable that the PB2-KO vaccine may confer protection against several different antigenic strains of influenza, or subtypes of influenza and/or other pathogens. An added advantage includes the possibility of mucosal delivery of vaccine precluding the use of needles for subcutaneous injection of vaccine and so forth.

In conclusion, given that the PB2-KO virus elicited effective immune responses, induced antibodies against the product of a reporter gene encoded in its PB2 segment, is easily propagated, and can be safely administered as a vaccine, the PB2-KO virus represents a credible, safe, and efficacious vaccine candidate.

Example IV

Figure 10:
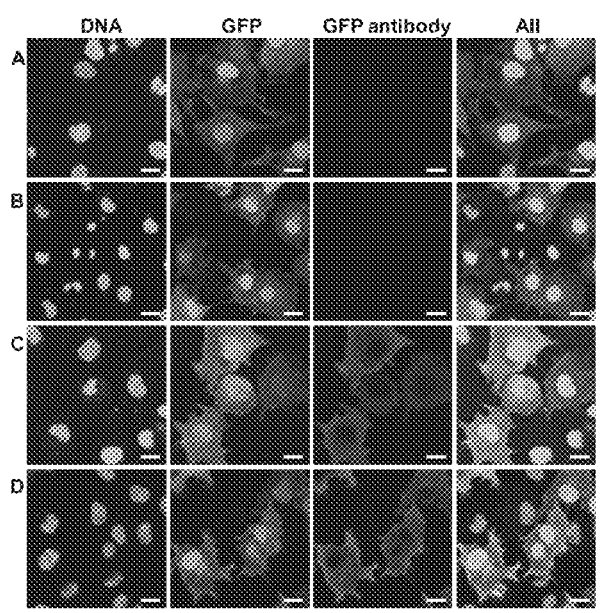
FIG. 10. Detection of antibodies against GFP in the sera of mice immunized with the PB2-KO virus. Confluent 293 cells that transiently express GFP were treated with sera (1/20 dilution) obtained from mice inoculated with medium (A), the formalin-inactivated virus (B), or the PB2-KO virus (C) or were treated with a commercial anti-GFP antibody (D). DNA (first column) was stained with Hoechst 33342. GFP (second column) represents cells transfected with a plasmid for the expression of GFP. GFP antibody (third column) represents the presence of the GFP antibody in the samples. These three images were merged (fourth column). Scale bars, 20 μm.

*Streptococcus pneumoniae* is a respiratory pathogen that causes secondary bacterial infection following influenza virus infection, which is associated with elevated mortality in the elderly. Parainfluenza viruses, such as respiratory syncytial virus and human parainfluenza virus type 1, are respiratory pathogens that cause severe manifestations in infants. No vaccines are currently available for parainfluenza virus. The PB2-KO virus could be used as a multivalent vaccine because an antibody against the reporter gene product (GFP in this case) encoded in the coding region of the PB2 segment was induced in place of authentic PB2 (FIG. 10). If major antigens of pathogens are similarly encoded in the coding region of the PB2 segment, the PB2-KO virus could induce immune responses against those antigens as well as against influenza viral proteins, thereby protecting infants and the elderly from these serious respiratory diseases.

Figure 11:
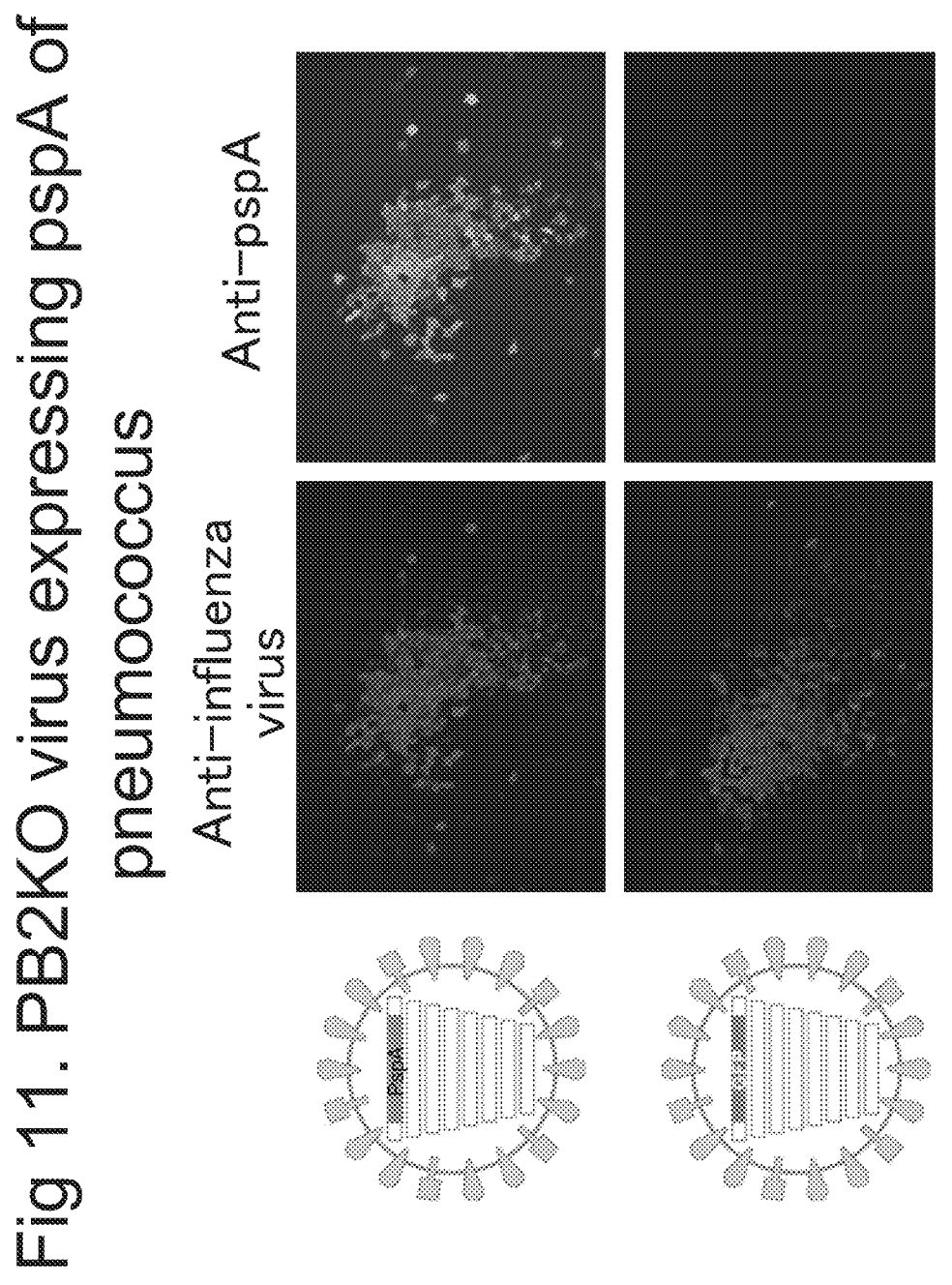
Figure 12:
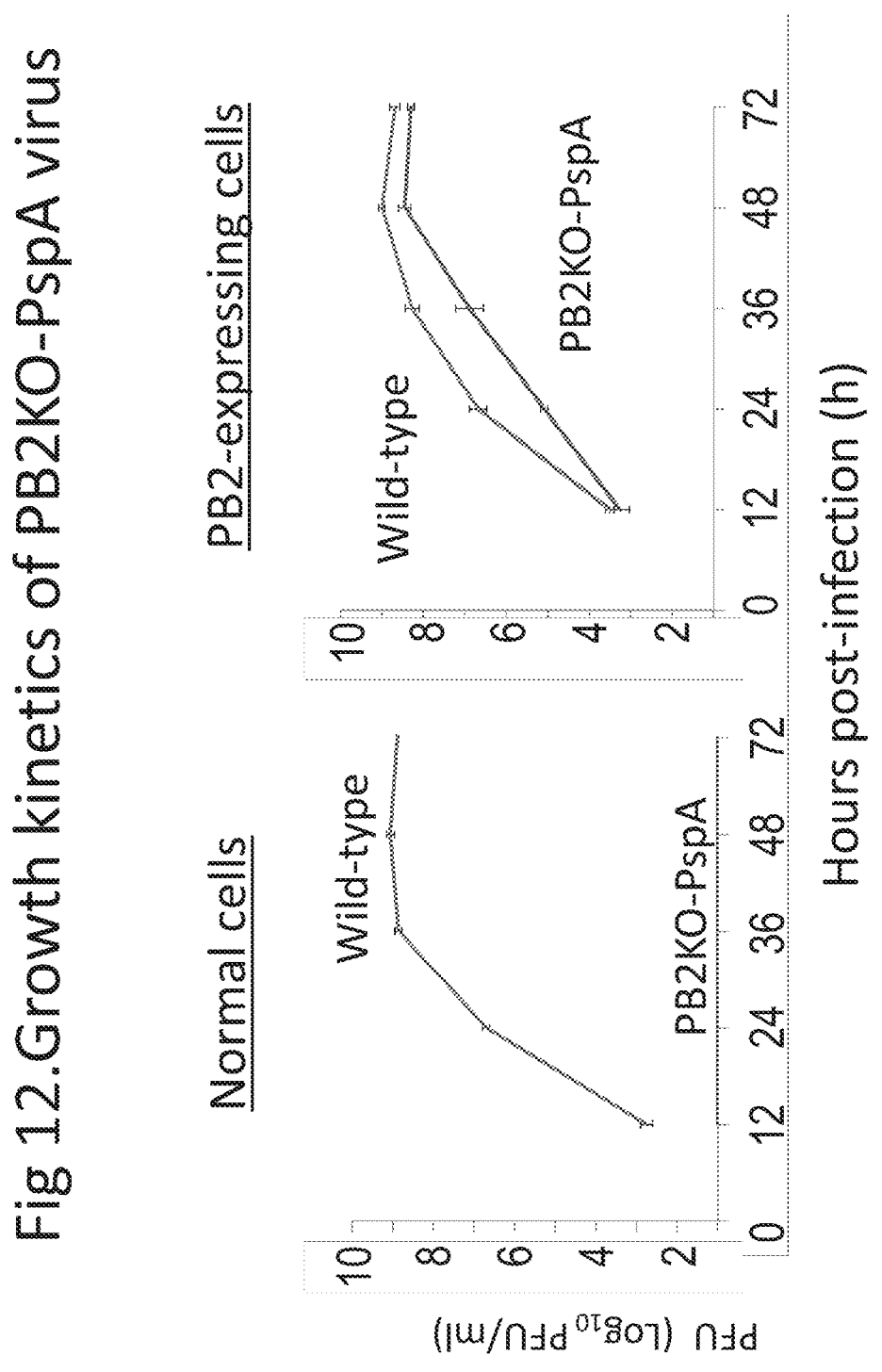

FIG. 11 shows expression of PspA of *Streptococcus pneumonia* and influenza virus antigen in cells having PB2-KO-PspA, and expression of influenza virus antigen in cells having PB2-KO-GFP. PB2-KO-PspA has growth kinetics similar to wild-type influenza virus in cells that express PB2 in trans but is unable to expand in cells that do not express PB2 in trans (FIG. 12).

Figure 13:
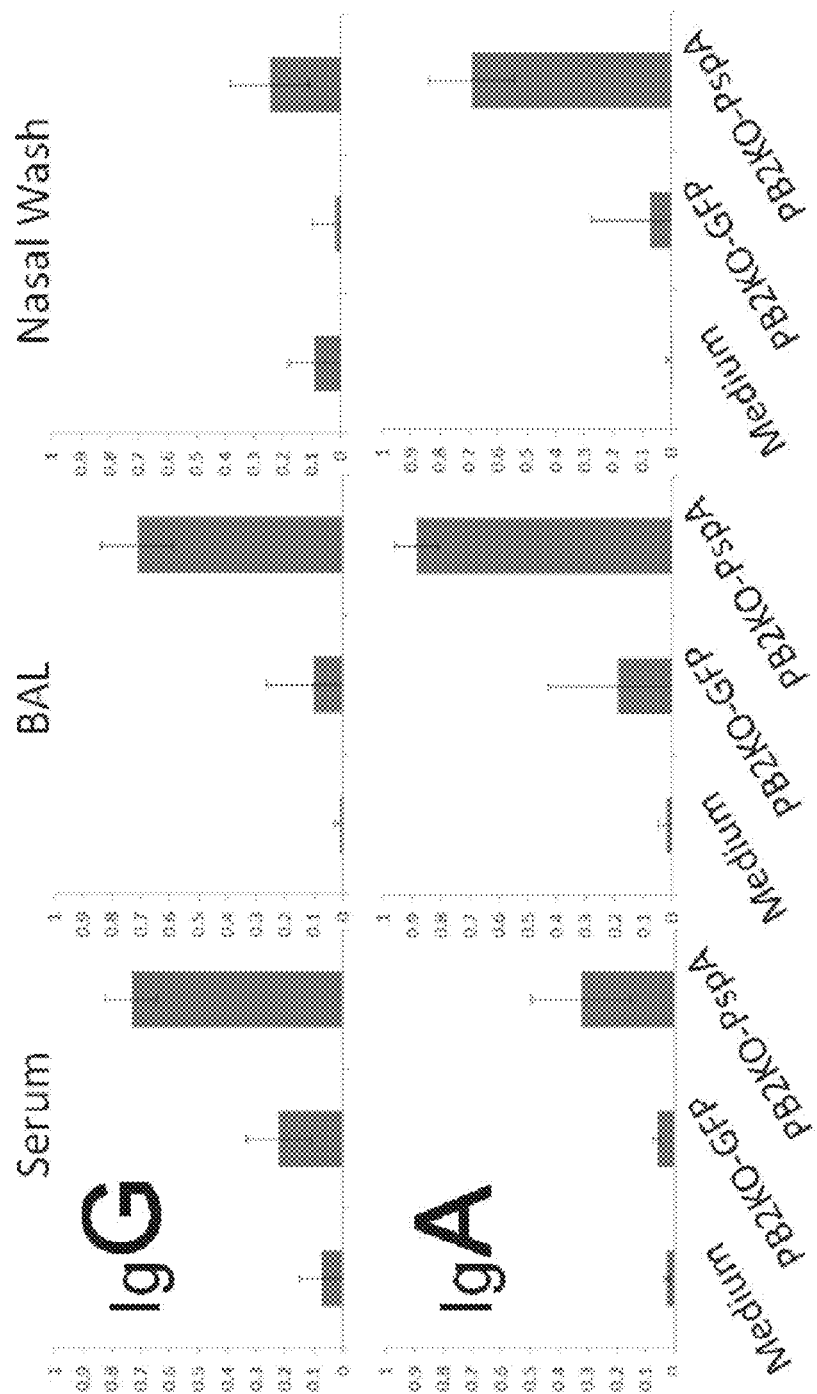
FIG. 13. Influenza antigen specific IgG and IgA in serum, BAL and nasal washes from mice immunized three times with PB2-KO-PspA or PB2-KO-GFP.
Figure 14:
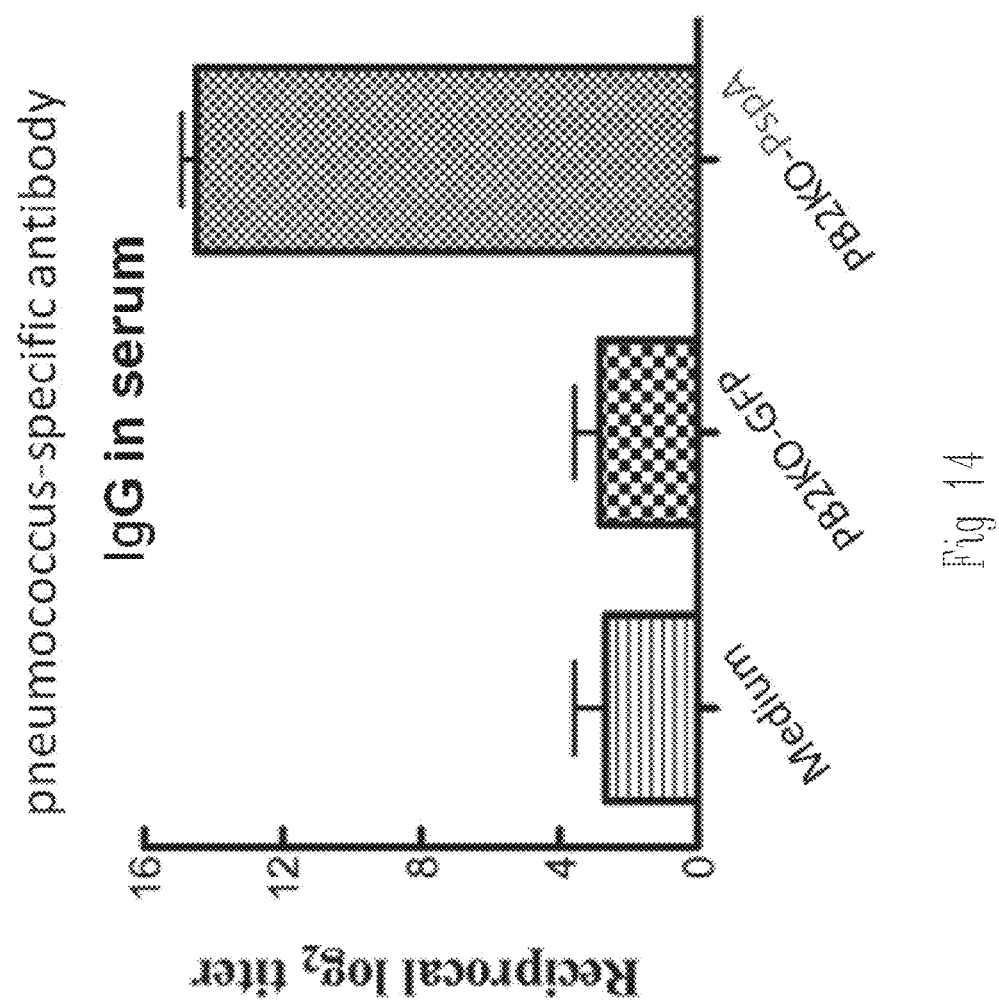
FIG. 14. PspA specific IgG in serum from mice immunized three times with PB2-KO-PspA.
Figure 15:
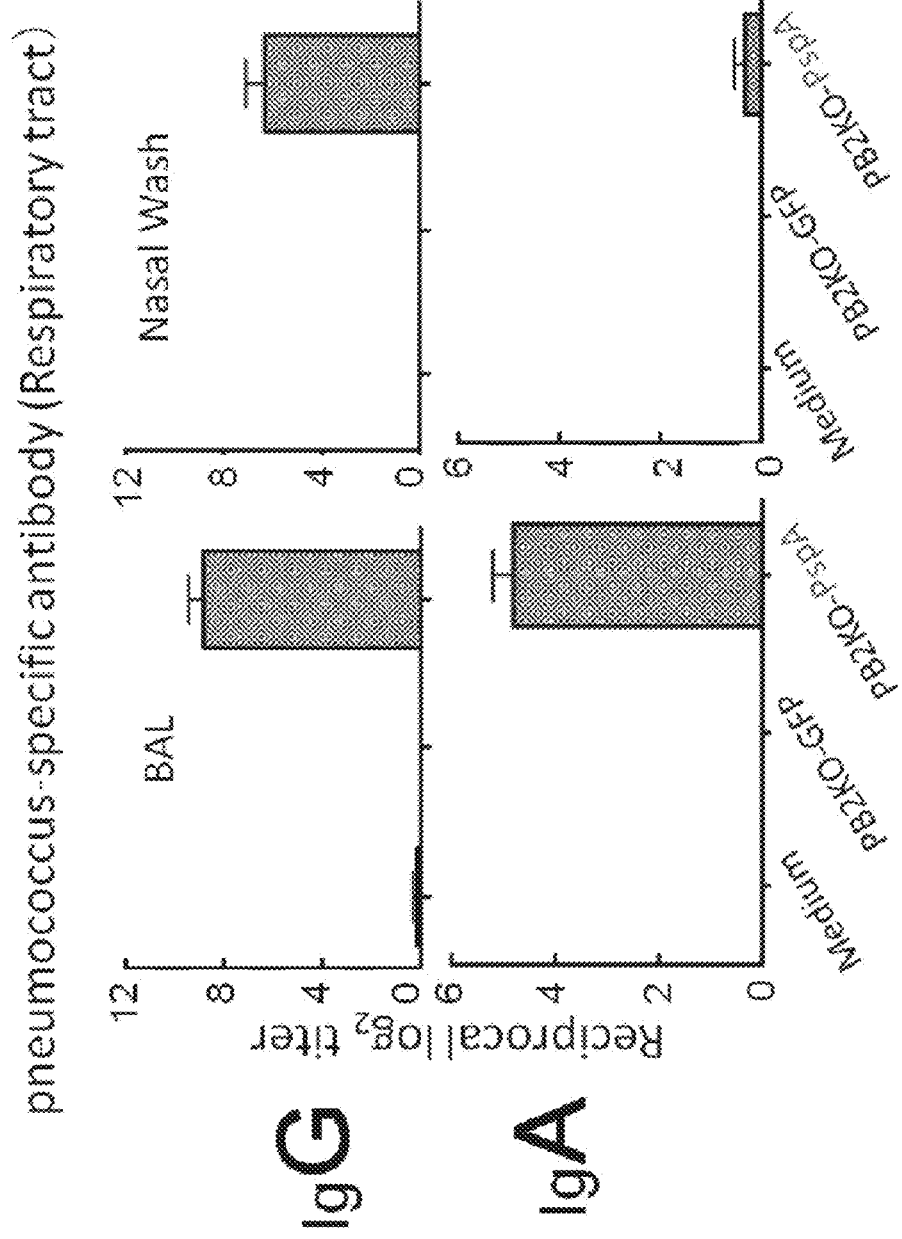
FIG. 15. PspA specific IgG and IgA in BAL and nasal washes from mice immunized three times with PB2-KO-PspA.

Mice infected with PB2-KO-PspA or PB2-KO-GFP have influenza specific IgG and IgA in sera, BAL and nasal washes (FIG. 13), and mice infected with PB2-KO-PspA, but not PB2-KO-GFP, have pneumococcal specific IgG in sera (FIG. 14), and BAL and nasal washes (FIG. 15).

Figure 16:
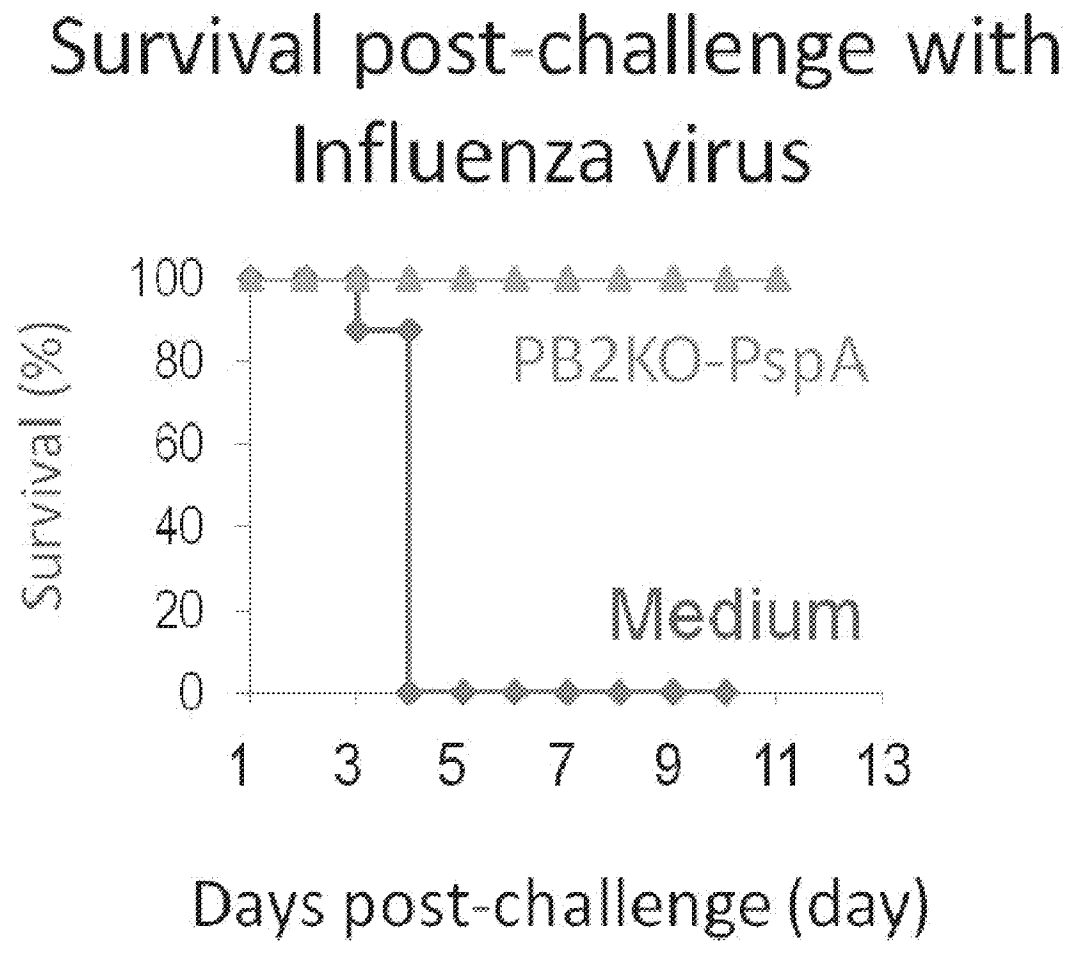
Figure 17:
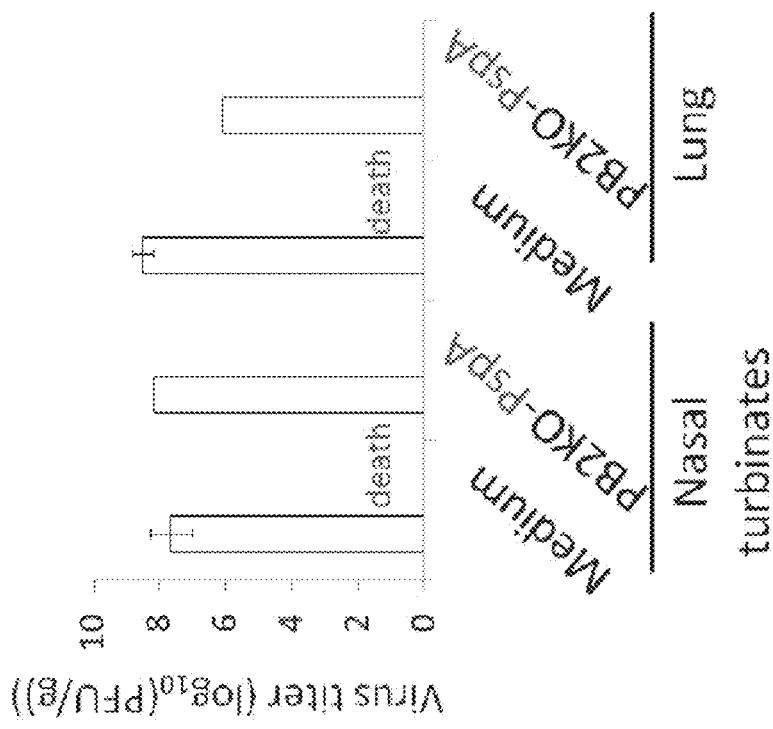
FIG. 17. Virus replication in the respiratory tract at day 3 post-challenge in mice immunized three times with PB2-KO-PspA and challenged with 10 $LD_{50}$ or 100 $LD_{50}$ of influenza virus.
Figure 18:
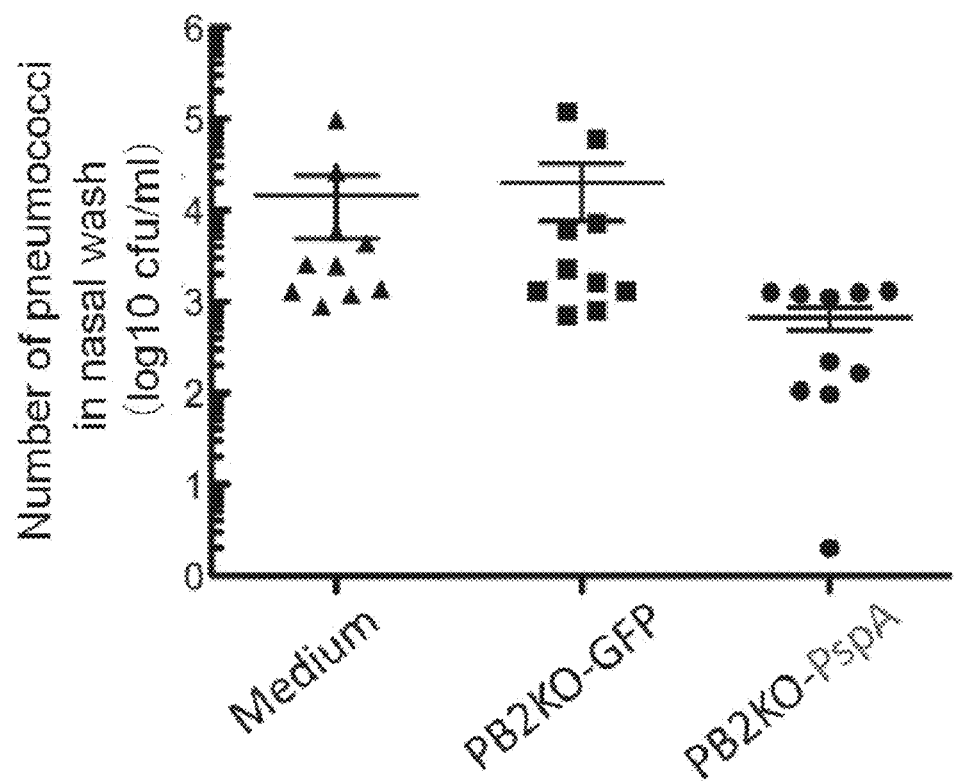
FIG. 18. Number of pneumococci in nasal washes from mice immunized three times with PB2-KO-PspA or PB2-KO-GFP and challenged with $10^2$ CFU *S. pneumoniae* (EF3030)/mouse.
Figure 19:
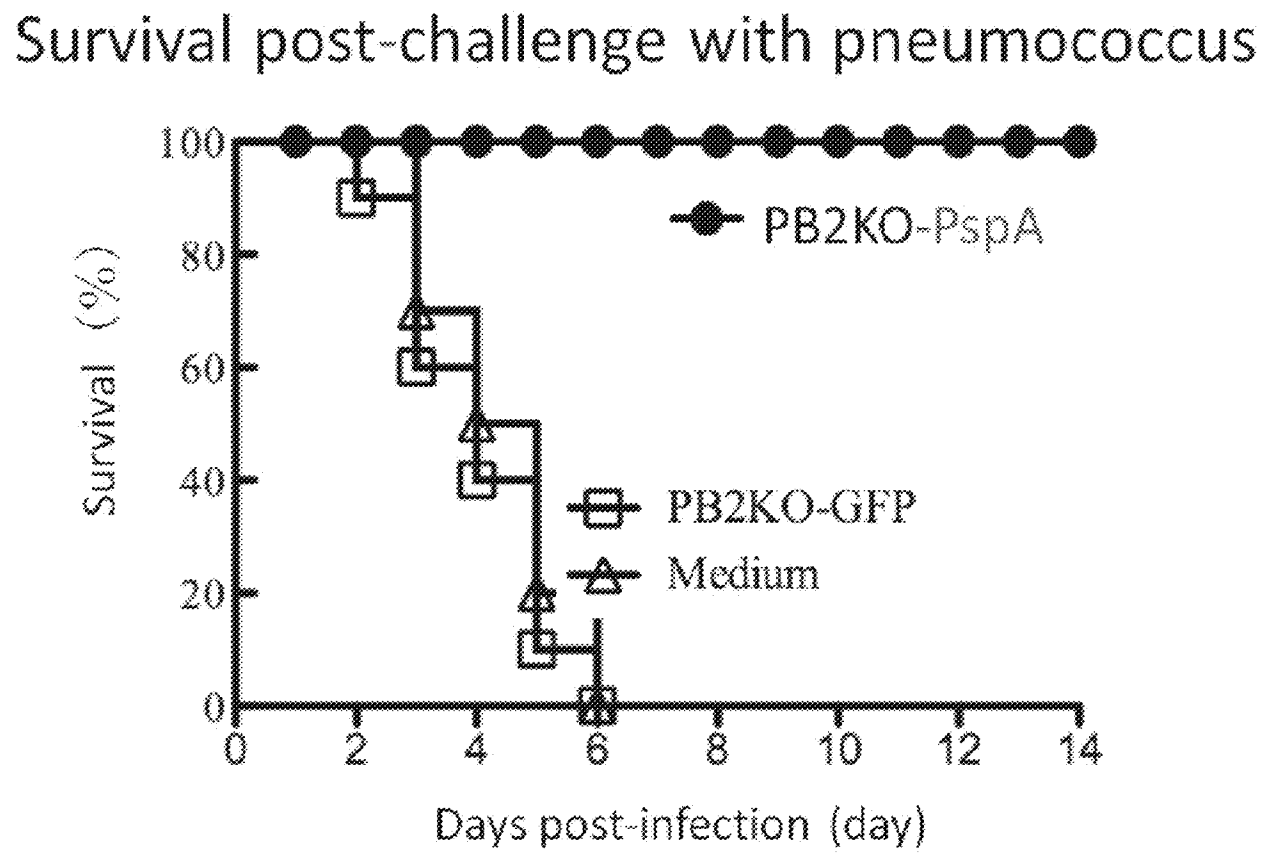

Mice immunized three times with PB2-KO-PspA survived challenge with influenza virus (FIG. 16) and *Streptococcus pneumonia* (FIG. 19). Influenza virus in the control and immunized mice could be detected in nasal turbinates and lung at day 3 post-challenge (FIG. 17). Post-challenge, bacterial load was reduced in PB2-KO-PspA, but not PB2-KO-GFP, immunized mice (FIG. 18).

REFERENCES

Cox et al., *Scand. J. Immunol.,* 59:1 (2004).
Davies et al., *Science,* 144:862 (1964).
DuBridge et al., *Mol. Cell Biol.,* 7:379 (1987).
Duhaut et al., *Virology,* 248:241 (1998).
Gruber, *Vaccine,* 20:566 (2002).
Fiore et al., *MMWR Recommend. Rep.,* 59:1 (2010).
Fulvini et al., *PLoS One,* 6:e20823 (2011)
Halperin et al., *Vaccine,* 20:1240 (2002).
Hampson, *Ann. Acad. Med. Singapore,* 37:510 (2008).
Hardy et al., *Virology,* 211:302 (1995).
Hatakeyuma et al., *J. Clin. Mirobiol.,* 43:4139 (2005).
Hatta et al., *Arch. Virol.,* 145:1947 (2000).
Hayden, *Trans. R. Soc. Lond. B. Biol. Sci.,* 356:1877 (2001).
Hoffmann et al., *J. Virol.,* 79:11014 (2005).
Horimoto et al., *Virology,* 366:23 (2007).
Hossain et al., *J. Clin. Microbiol.,* 48:2515 (2010).
Itoh et al., *Nature,* 460:1021 (2009).
Iwatsuki-Horimoto et al., *Clin. Vaccine Immunol.,* 18:860 (2011).
Jennings et al., *Cell,* 34:619 (1983).
Katz et al., *J. Virol.,* 64:1808 (1990).
Kemble et al., *Vaccine,* 21:1789 (2003).
Kida et al., *Virology,* 122:38 (1982).
Kobasa et al., *Nature,* 431:703 (2004).
Kong et al., *Proc. Natl. Acad. Sci. USA,* 103:15987 (2006).
Li et al., *J. Virol.,* 84:12075 (2010).
Li et al., *Viruses,* 3:241 (2009).
Lin et al., *Virus Res.,* 103:47 (2004).
Maassab, *Nature,* 219:645 (1968).
Manicassamy et al., *Proc. Natl. Acad. Sci. USA,* 107:11531 (2010).
Martinez-Sobrido et al., *J. Virol.,* 84:2157 (2010).
Moss et al., *J. Antimicrob. Chemother.,* 65:1086 (2010).
Muramoto et al., *J. Virol.,* 80:2318 (2006).
Murphy et al., *Viral. Immunol.,* 15:295 (2002).
Nayak et al., *J. Virol.,* 84:2408 (2010).
Neumann et al., *Proc. Natl. Acad. Sci. USA,* 96:9345 (1999).
Niwa et al., *Gene,* 108:193 (1991).
Noble et al., *Virology,* 210:9 (1995).
Odagiri et al., *Proc. Natl. Acad. Sci. USA,* 87:5988 (1990).
Ozawa et al., *J. Gen. Virol.,* 92:2879 (2011).
Palese et al., *J. Clin. Invest.,* 110:9 (2002).
Palese et al., In *Fields virology,* 5th edn, pp. 1647-1689 (2007), Edited by D. M. Knipe & P. M. Howley, Philadelphia, Pa.: Lippincott-Raven Publishers.
Reichert et al, *N. Engl. J. Mol.,* 344:889 (2001).
Rimmelzwaan et al., *Vaccine,* 29:3424 (2011).
Robertson, *Rev. Med. Virol.,* 3:97 (1993).
Robertson et al., *J. Gen. Virol.,* 72:2671 (1991).
Smith et al., *J. Gen. Virol.,* 68:2729 (1987).
Vesikari et al., *Pediatr. Infect. Dis. J.,* 25:590 (2006).
Watanabe et al., *J. Virol.,* 76:767 (2002).
Watanabe et al., *J. Virol.,* 83:5947 (2009).
Wright et al., In *Fields virology,* 5th edn, pp. 1691-1740 (2007). Edited by D. M. Knipe & P. M. Howley, Philadelphia, Pa.: Lippincott-Raven Publishers.
Yamada et al., *PloS Pathog.,* 6:e1001034 (2010).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A vaccine comprising an effective amount of an isolated stable, biologically contained multivalent influenza virus comprising: i) 8 different gene segments including a PA viral gene segment, a PB1 viral gene segment, a mutant PB2 viral gene segment, a HA viral gene segment, a NA viral gene segment, a NP viral gene segment, a M (M1 and M2) viral gene segment, and a NS (NS1 and NS2) viral gene segment, ii) 8 different gene segments including a PA viral gene segment, a PB1 viral gene segment, a mutant PB2 viral gene segment, a HA viral gene segment, a NA (NA and NB) viral gene segment, a NP viral gene segment, a M (M1 and BM2) viral gene segment and a NS (NS1 and NS2) viral gene segment, or iii) 7 different gene segments including a PA viral gene segment, a PB1 viral gene segment, a mutant PB2 viral gene segment, a HEF viral gene segment, a NP viral gene segment, a M (M1 and CM2) viral gene segment, and a NS (NS1 and NS2) viral gene segment;
wherein the mutant PB2 viral gene segment includes 5' and 3' incorporation sequences including 3' or 5' coding and non-coding incorporation sequences flanking a heterologous nucleotide sequence and does not include contiguous sequences corresponding to sequences encoding a functional PB2, and wherein the heterologous nucleotide sequence encodes a gene product that induces a prophylactic or therapeutic immune response to a pathogen.

2. The vaccine of claim 1 wherein the heterologous nucleotide sequence comprises sequences for an antigen.

3. The vaccine of claim 2 wherein the antigen is a glycoprotein.

4. The vaccine of claim 1 which comprises H1, H2, H3, H5, H7, or H9 HA.

5. A method to immunize a vertebrate, comprising: contacting the vertebrate with the vaccine of claim 1.

6. The method of claim 5 wherein the vertebrate is an avian or a mammal.

7. A method to prepare a biologically contained, multivalent 8 segment influenza A or B virus, comprising contacting a host cell with one or more vectors which include transcription cassettes for vRNA production and transcription cassettes for mRNA production, wherein the transcription cassettes for vRNA production are a transcription cassette comprising a PolI promoter operably linked to an influenza virus PA DNA in an orientation for vRNA production linked to a PolI transcription termination sequence, a transcription cassette comprising a PolI promoter operably linked to an influenza virus PB1 DNA in an orientation for vRNA production linked to a PolI transcription termination sequence, a transcription cassette comprising a PolI promoter operably linked to a mutant influenza virus PB2 DNA in an orientation for vRNA production linked to a PolI transcription termination sequence, a transcription cassette comprising a PolI promoter operably linked to an influenza virus HA DNA in an orientation for vRNA production linked to a PolI transcription termination sequence, a transcription cassette comprising a PolI promoter operably linked to an influenza virus NA DNA in an orientation for vRNA production linked to a PolI transcription termination sequence, a transcription cassette comprising a PolI promoter operably linked to an influenza virus NP DNA in an orientation for vRNA production linked to a PolI transcription termination sequence, a transcription cassette comprising a PolI promoter operably linked to an influenza virus M DNA in an orientation for vRNA production linked to a PolI transcription termination sequence, and a transcription cassette comprising a PolI promoter operably linked to an influenza virus NS (NS1 and NS2) DNA in an orientation for vRNA production linked to a PolI transcription termination sequence, wherein the mutant PB2 DNA includes 5' and 3' incorporation sequences including 3' or 5' coding and non-coding incorporation sequences flanking a heterologous nucleotide sequence and does not include contiguous sequences corresponding to sequences that encode a functional PB2, and wherein the heterologous nucleotide sequence encodes a gene product that induces an immune response to a pathogen; and wherein the transcription cassettes for mRNA production are a transcription cassette comprising a PolI promoter operably linked to a DNA coding region for influenza virus PA linked to a PolII transcription termination sequence, a transcription cassette comprising a PolI promoter operably linked to a DNA coding region for influenza virus PB1 linked to a PolI transcription termination sequence, and a transcription cassette comprising a PolI promoter operably linked to a DNA coding region for influenza virus NP linked to a PolI transcription termination sequence, wherein the genome of host cell is stably augmented with a transcription cassette comprising a PolI promoter operably linked to a DNA coding region for influenza virus PB2 linked to a PolI transcription termination sequence, and wherein the host cell does not comprise sequences corresponding to PB2 coding sequences for vRNA production of a wild-type PB2 gene segment; and isolating the biologically contained virus from the host cell.

8. A method to re are a biologically contained, multivalent 8 segment influenza A or B virus, comprising contacting a host cell with one or more vectors which include transcription cassettes for vRNA production and transcription cassettes for mRNA production, wherein the transcription cassettes for vRNA production are a transcription cassette comprising a PolI promoter operably linked to an influenza virus PA DNA in an orientation for vRNA production linked to a PolI transcription termination sequence, a transcription cassette comprising a PolI promoter operably linked to an influenza virus PB1 DNA in an orientation for vRNA production linked to a PolI transcription termination sequence, a transcription cassette comprising a PolI promoter operably linked to a mutant influenza virus PB2 DNA in an orientation for vRNA production linked to a PolI transcription termination sequence, a transcription cassette comprising a PolI promoter operably linked to an influenza virus HA DNA in an orientation for vRNA production linked to a PolI transcription termination sequence, a transcription cassette comprising a PolI promoter operably linked to an influenza virus NA DNA in an orientation for vRNA production linked to a PolI transcription termination sequence, a transcription cassette comprising a PolI promoter operably linked to an influenza virus NP DNA in an orientation for vRNA production linked to a PolI transcription termination sequence, a transcription cassette comprising a PolI promoter operably linked to an influenza virus M DNA in an orientation for vRNA production linked to a PolI transcription termination sequence, and a transcription cassette comprising a PolI promoter operably linked to an influenza virus NS (NS1 and NS2) DNA in an orientation for vRNA production linked to a PolI transcription termination sequence, wherein the mutant PB2 DNA includes 5' and 3' incorporation sequences including or 5' coding and non-coding incorporation sequences flanking a heterologous nucleotide sequence and does not include contiguous sequences corresponding to sequences that encode a functional PB2, and wherein the heterologous nucleotide sequence encodes a gene product that induces an immune response to a pathogen; and wherein the transcription cassettes for mRNA production are a transcription cassette comprising a PolI promoter operably linked to a DNA coding region for influenza virus PA linked to a PolII transcription termination sequence, a transcription cassette comprising a PolI promoter operably linked to a DNA coding region for influenza virus PB1 linked to a PolI transcription termination sequence, and a transcription cassette comprising a PolI promoter operably linked to a DNA coding region for influenza virus NP linked to a PolI transcription termination sequence, wherein the genome of host cell is stably augmented with a transcription cassette comprising a PolI promoter operably linked to a DNA coding region for influenza virus PB2 linked to a PolI transcription termination sequence, and wherein the host cell does not comprise sequences corresponding to PB2 coding sequences for vRNA production of a wild-type PB2 gene segment; and isolating the biologically contained virus from the host cell, wherein the cell is contacted with the vector for mRNA production of PB2 before the other vectors.

9. The method of claim 7 wherein the heterologous nucleotide sequence encodes an antigen.

10. The method of claim 7 wherein the HA is a type A HA.

11. The method of claim 10 wherein the HA is a H1, H2, H3, H5, H7, or H9 HA.

12. The method of claim 8 wherein the heterologous nucleotide sequence encodes an antigen.

13. The method of claim 7 wherein the biologically contained virus is a 6:2 reassortant.

14. The vaccine of claim 1 wherein the biologically contained virus is a reassortant virus.

15. The vaccine of claim 14 wherein the gene segments for HA and NA are from a different isolate that the PA, PB1, PB2, NP, NS, and M gene segments.

16. The method of claim 7 wherein the cell is a 293 cell, a 293T cell, a DF-1 cell, a A549 cell, a Vero cell or a MDCK cell.

17. The vaccine of claim 1 wherein the heterologous nucleotide sequence is flanked by about 3 to about 400 nucleotides of the 5' and/or 3' PB2 coding region adjacent to non-coding sequence.

* * * * *